(12) United States Patent
Nishide et al.

(10) Patent No.: US 11,895,910 B2
(45) Date of Patent: Feb. 6, 2024

(54) ORGANIC COMPOUND AND PHOTOELECTRIC CONVERSION ELEMENT

(71) Applicant: CANON KABUSHIKI KAISHA, Tokyo (JP)

(72) Inventors: Yosuke Nishide, Kawasaki (JP); Naoki Yamada, Inagi (JP); Hiroki Ohrui, Kawasaki (JP); Hironobu Iwawaki, Yokohama (JP); Hirokazu Miyashita, Ebina (JP); Tomona Yamaguchi, Tokyo (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 360 days.

(21) Appl. No.: 16/106,534

(22) Filed: Aug. 21, 2018

(65) Prior Publication Data
US 2019/0067590 A1 Feb. 28, 2019

(30) Foreign Application Priority Data

Aug. 23, 2017 (JP) .............................. JP2017-160492

(51) Int. Cl.
*H10K 85/60* (2023.01)
*C07D 495/04* (2006.01)
(Continued)

(52) U.S. Cl.
CPC ......... *H10K 85/636* (2023.02); *C07D 495/04* (2013.01); *H04N 25/75* (2023.01);
(Continued)

(58) Field of Classification Search
CPC ..... H01L 51/0052–0074; H01L 51/424–4253; H01L 51/42–4253;
(Continued)

(56) References Cited

U.S. PATENT DOCUMENTS 6,583,557 B2   6/2003   Hashimoto et al.
6,833,200 B2   12/2004   Senoo et al.
(Continued)

FOREIGN PATENT DOCUMENTS

JP   2014-017484 A   1/2014
JP   2015-056360 A   3/2015
(Continued)

OTHER PUBLICATIONS

Yuan, et al. "Acceptor End-Capped Oligomeric Conjugated Molecules with Broadened Absorption and Enhanced Extinction Coefficients for High-Efficiency Organic Solar Cells." Advanced Materials 28.28 (2016): 5980-5985.*

(Continued)

*Primary Examiner* — Kourtney R S Carlson
(74) *Attorney, Agent, or Firm* — VENABLE LLP

(57) ABSTRACT

Provided is an organic compound represented by the following general formula [1], the compound having an absorption peak in a long wavelength region:

(Continued)

where $Ar_1$ and $Ar_2$ each represent an aryl group having 6 or more and 18 or less carbon atoms or the like, $R_1$ and $R_2$ each represent an alkyl group or the like, $R_3$ represents a hydrogen atom or the like, $Y_1$ to $Y_3$ are each independently selected from a methine group and a nitrogen atom, $R_4$ represents a substituent represented by the general formula [1-1] or the like, and $R_5$ represents a hydrogen atom or a substituent.

21 Claims, 3 Drawing Sheets

(51) Int. Cl.
H04N 25/75 (2023.01)
H10K 85/20 (2023.01)
H10K 30/30 (2023.01)

(52) U.S. Cl.
CPC ......... H10K 85/215 (2023.02); H10K 85/633 (2023.02); H10K 85/6576 (2023.02); *H10K 30/30* (2023.02); *H10K 85/211* (2023.02); *H10K 85/615* (2023.02)

(58) Field of Classification Search
CPC ....... H10K 85/60–6576; H10K 85/215; H10K 30/30; H04N 25/75; C02D 495/04
See application file for complete search history.

(56) References Cited

U.S. PATENT DOCUMENTS

| 8,890,134 | B2 | 11/2014 | Lee et al. |
| 10,629,826 | B2 | 4/2020 | Arai et al. |
| 10,825,995 | B2 | 11/2020 | Yakushiji et al. |
| 10,947,212 | B2 * | 3/2021 | Nishide ................ C07D 405/14 |
| 2005/0025997 | A1 | 2/2005 | Senoo et al. |
| 2012/0059140 | A1 * | 3/2012 | Hayoz ................ C08G 61/124 528/8 |
| 2014/0273756 | A1 | 9/2014 | Chen et al. |
| 2016/0190188 | A1 * | 6/2016 | Murakami ........ H01L 27/14632 250/214 A |
| 2017/0040550 | A1 | 2/2017 | Yakushiji |
| 2018/0198068 | A1 * | 7/2018 | Morse ................ C07D 495/14 |
| 2019/0092743 | A1 * | 3/2019 | Nishide ................ C07D 405/12 |

FOREIGN PATENT DOCUMENTS

| JP | 2016-175868 A | 10/2016 | |
| KR | 2014-0132842 A | 11/2014 | |
| WO | WO-2014051007 A1 * | 4/2014 | ........ C09B 23/0058 |
| WO | 2015/163349 A1 | 10/2015 | |
| WO | 2017/149958 A1 | 9/2017 | |
| WO | 2018/016354 A1 | 1/2018 | |

OTHER PUBLICATIONS

Štefko, et al. "Donor-Acceptor (D-A)-Substituted Polyyne Chromophores: Modulation of Their Optoelectronic Properties by Varying the Length of the Acetylene Spacer." Chemistry—A European Journal 19.38 (2013): 12693-12704.*
Machine translation of WO-2014051007-A1.*
U.S. Appl. No. 16/243,500, filed Jan. 9, 2019, Yamada et al.
U.S. Appl. No. 16/130,029, filed Sep. 13, 2018, Yamada et al.
U.S. Appl. No. 16/163,757, filed Oct. 18, 2018, Nishide et al.
U.S. Appl. No. 16/114,686, filed Aug. 28, 2018, Miyashita et al.
U.S. Appl. No. 16/051,724, filed Aug. 1, 2018, Yamada et al.
Jae Kwan Lee et al., "Pushepull Organic Semiconductors with Planar Indenothiophene Bridges for Solution-Processed Small-Molecule Organic Solar Cells," 70 Tetrahedron 6235-6240 (Feb. 2014).
Notice of Reasons for Refusal in Japanese Application No. 2017-160492 (dated Aug. 2021).

* cited by examiner

ORGANIC COMPOUND AND PHOTOELECTRIC CONVERSION ELEMENT

BACKGROUND

Field of the Disclosure

The present disclosure relates to an organic compound, an organic electronic element and a photoelectric conversion element each using the organic compound, and an imaging device and an imaging apparatus each using the photoelectric conversion element.

Description of the Related Art

A photoelectric conversion element is an element configured to receive light from the outside and to convert its energy into electrical energy. A solid imaging device having a sensor in which a plurality of photoelectric conversion elements are arrayed in a two-dimensional manner has been widely diffused by applying the foregoing characteristic. In recent years, the development of a photoelectric conversion element including an organic compound in its photoelectric conversion layer has been advanced, but in order that the element may be put into practical use, the element is susceptible to improvement in terms of, for example, conversion efficiency and durability.

In Tetrahedron, 70 (2014), 6235-6240 (hereinafter NPL 1), there is a description of Organic Compound a-1 having an indenothienothiophene structure, and there is a description of a solar cell using the compound.

In Korean Publication No. 2014-0132842 (hereinafter PTL 1), there is a description of Organic Compound b-1 having an indenothienothiophene structure, and there is a description of a solar cell using the compound.

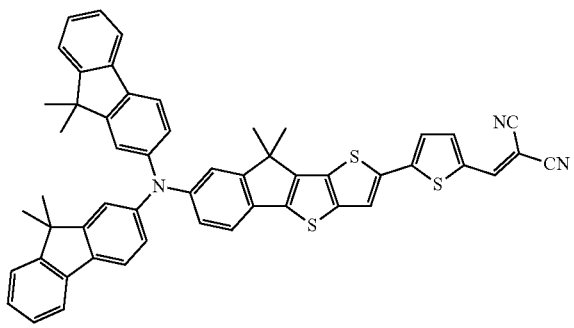

a-1

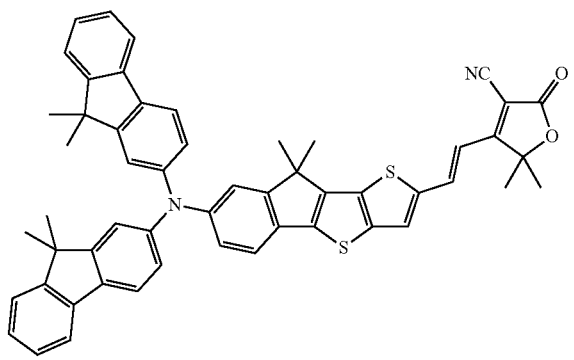

b-1

However, Organic Compounds a-1 and b-1 have been compounds having low molar extinction coefficients. Accordingly, when any one of the compounds is used in a photoelectric conversion element, the absorptivity of a photoelectric conversion film reduces, and the reduction leads to a reduction in efficiency of the element or an increase in driving voltage thereof.

SUMMARY

The present disclosure has been made to solve the problems, and an object of the present disclosure is to provide an organic compound having light absorption in a wide range of a visible light region and having a high molar extinction coefficient. Another object of the present disclosure is to provide a photoelectric conversion element that has high efficiency or a low driving voltage in a wide range of the visible light region through the use of the organic compound in the element.

In view of the foregoing, according to one embodiment of the present disclosure, there is provided an organic compound, which is represented by the following general formula [1]:

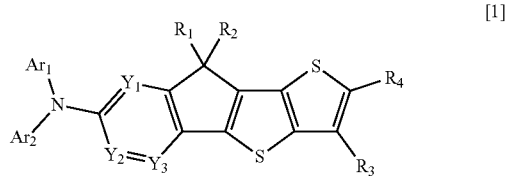

[1]

in the general formula [1], $Ar_1$ and $Ar_2$ are each independently selected from an aryl group having 6 or more and 18 or less carbon atoms, and a heteroaryl group having 3 or more and 17 or less carbon atoms, the $Ar_1$ and the $Ar_2$ may each have a halogen atom, a cyano group, an alkyl group, an alkoxy group, an aryl group, or a heteroaryl group as a substituent, the alkyl group, the alkoxy group, the aryl group, or the heteroaryl group serving as the substituent may further have a halogen atom, a cyano group, an alkyl group, or an alkoxy group as a substituent, and the $Ar_1$ and the $Ar_2$ may be bonded to each other to form a ring, $R_1$ and $R_2$ are each independently selected from a hydrogen atom, a halogen atom, a cyano group, an alkyl group, an aryl group having 6 or more and 18 or less carbon atoms, and a heteroaryl group having 3 or more and 17 or less carbon atoms, the alkyl group represented by any one of the $R_1$ and the $R_2$ may have a halogen atom as a substituent, the aryl group having 6 or more and 18 or less carbon atoms, and the heteroaryl group having 3 or more and 17 or less carbon atoms each represented by any one of the $R_1$ and the $R_2$ may each have a halogen atom, a cyano group, an alkyl group, or an alkoxy group as a substituent, and the $R_1$ and the $R_2$ may be bonded to each other to form a ring, $R_3$ is selected from a hydrogen atom, a halogen atom, a cyano group, and an alkyl group, and the alkyl group represented by the $R_3$ may have a halogen atom as a substituent, $Y_1$ to $Y_3$ are each independently selected from a methine group and a nitrogen atom, and when any one of the $Y_1$ to the $Y_3$ represents a methine group, the methine group may have a substituent and the substituent is each independently selected from a halogen atom, a cyano group, and an alkyl group, and the alkyl group serving as the substituent that the methine group has may further have a halogen atom as a substituent, and $R_4$ represents a substituent selected from the following general formulae [1-1] and [1-2], and * in each of the following general formulae [1-1] and [1-2] represents a bonding position:

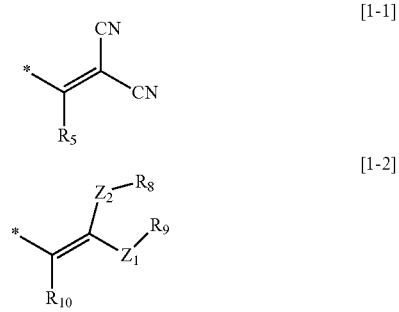

[1-1]

[1-2]

in the general formulae [1-1] and [1-2], $R_5$ and $R_8$ to $R_{10}$ are each independently selected from a hydrogen atom, a halogen atom, a cyano group, an amino group, an amide group, an alkyl group, an alkoxy group, an alkenyl group, an alkynyl group, an aryl group having 6 or more and 18 or less carbon atoms, and a heteroaryl group having 3 or more and 17 or less carbon atoms, and the $R_8$ and the $R_9$ are bonded to each other to form a ring, and the amino group, the amide group, the alkyl group, the alkoxy group, the alkenyl group, the alkynyl group, the aryl group having 6 or more and 18 or less carbon atoms, or the heteroaryl group having 3 or more and 17 or less carbon atoms represented by any one of the $R_5$ and the $R_8$ to the $R_{10}$ may have a halogen atom, a cyano group, an alkyl group having 1 or more and 8 or less carbon atoms, an alkoxy group having 1 or more and 8 or less carbon atoms, an aryl group having 6 or more and 12 or less carbon atoms, or a heteroaryl group having 4 or more and 11 or less carbon atoms as a substituent, and in the general formula [1-2], $Z_1$ and $Z_2$ are each independently selected from groups represented by the following formulae [1-3] to [1-5], and * in each of the following formulae [1-3] to [1-5] represents a bonding position.

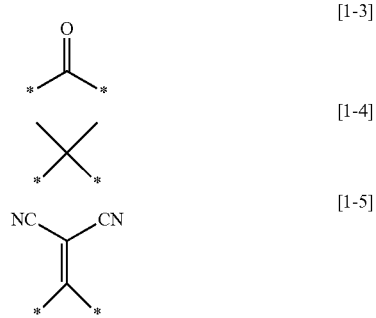

[1-3]

[1-4]

[1-5]

Further features of the present invention will become apparent from the following description of exemplary embodiments with reference to the attached drawings.

DESCRIPTION OF THE EMBODIMENTS

Figure 1:
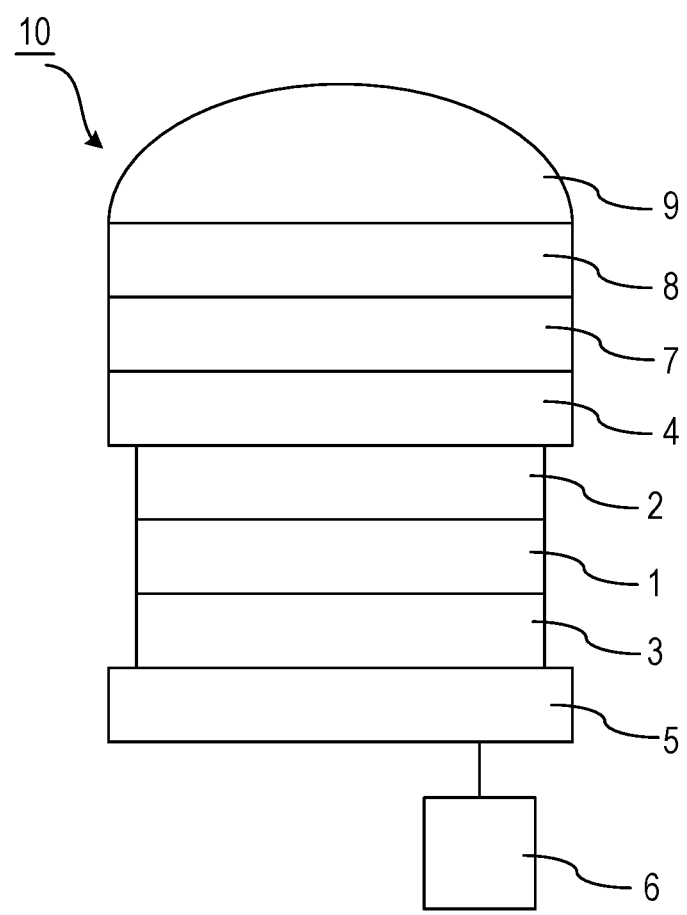
FIG. 1 is a schematic sectional view for illustrating an example of a photoelectric conversion element according to an embodiment of the present disclosure.

Preferred embodiments of the present invention will now be described in detail in accordance with the accompanying drawings.

Organic Compound According to Embodiment of the Present Disclosure

An organic compound according to an embodiment of the present disclosure is represented by the following general formula [1].

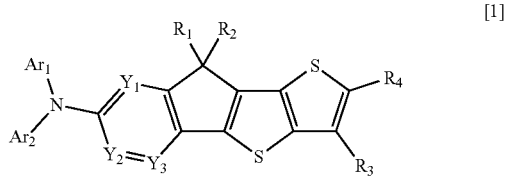

[1]

(1) $Ar_1$ and $Ar_2$

In the general formula [1], $Ar_1$ and $Ar_2$ are each independently selected from an aryl group having 6 or more and 18 or less carbon atoms, and a heteroaryl group having 3 or more and 17 or less carbon atoms.

Examples of the aryl group having 6 or more and 18 or less carbon atoms include a phenyl group, a biphenyl group, a terphenyl group, a naphthyl group, a phenanthryl group, and a fluorenyl group. Of those, a phenyl group, a biphenyl group, or a naphthyl group, which has a relatively small molecular weight, is preferred.

The heteroaryl group having 3 or more and 17 or less carbon atoms is a heteroaryl group having at least one of oxygen, nitrogen, or sulfur as a heteroatom. Specific examples thereof include a pyridyl group, a pyrazinyl group, a pyrimidinyl group, a triazinyl group, a quinolyl group, an isoquinolyl group, an oxazolyl group, a thiazolyl group, an imidazolyl group, a benzoxazolyl group, a benzothiazolyl group, a benzoimidazolyl group, a thienyl group, a furanyl group, a pyronyl group, a benzothienyl group, a benzofuranyl group, an indonyl group, a dibenzothiophenyl group, and a dibenzofuranyl group. Of those, a pyridyl group, a quinolyl group, an isoquinolyl group, or a benzothienyl group, which has a relatively small molecular weight and high stability, is preferred.

The $Ar_1$ and the $Ar_2$ may each have a halogen atom, a cyano group, an alkyl group, an alkoxy group, an aryl group, or a heteroaryl group as a substituent. The alkyl group, the alkoxy group, the aryl group, and the heteroaryl group serving as the substituents may each further have a halogen atom, a cyano group, an alkyl group, or an alkoxy group as a substituent. In the case of the aryl group or the heteroaryl group, the group preferably has the substituent.

The alkyl group is preferably an alkyl group having 1 or more and 8 or less carbon atoms, which has a relatively small molecular weight. Specific examples thereof include a methyl group, an ethyl group, a n-propyl group, an iso-propyl group, a n-butyl group, an iso-butyl group, a sec-butyl group, a tert-butyl group, a n-pentyl group, a n-hexyl group, a cyclohexyl group, a n-heptyl group, a n-octyl group, and a 2-ethylhexyl group. The alkyl group may have a halogen atom, preferably a fluorine atom as a substituent.

The alkoxy group is preferably an alkoxy group having 1 or more and 8 or less carbon atoms, which has a relatively small molecular weight. Specific examples thereof include a methoxy group, an ethoxy group, a n-propoxy group, an iso-propoxy group, a n-butoxy group, an iso-butoxy group, a sec-butoxy group, a tert-butoxy group, a n-hexyloxy group, a cyclohexyloxy group, a n-heptyloxy group, a n-octyloxy group, and a 2-ethylhexyloxy group.

Examples of the aryl group include a methylphenyl group, a dimethylphenyl group, a trimethylphenyl group, a biphenyl group, and a terphenyl group.

Examples of the heteroaryl group include a pyridyl group, a quinolyl group, an isoquinolyl group, a thienyl group, a furanyl group, a benzothienyl group, and a benzofuranyl group.

The $Ar_1$ and the $Ar_2$ may be bonded to each other to form a ring. At this time, the $Ar_1$ and the $Ar_2$ may be bonded to each other through a heteroatom, such as nitrogen, oxygen, or sulfur. The ring to be formed, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur.

(2) $R_1$ and $R_2$

In the general formula [1], $R_1$ and $R_2$ are each independently selected from a hydrogen atom, a halogen atom, a cyano group, an alkyl group, an aryl group having 6 or more and 18 or less carbon atoms, and a heteroaryl group having 3 or more and 17 or less carbon atoms. Specific examples of the alkyl group, the aryl group having 6 or more and 18 or less carbon atoms, and the heteroaryl group having 3 or more and 17 or less carbon atoms are as listed for the $Ar_1$ and the $Ar_2$. The alkyl group may have a halogen atom, preferably a fluorine atom as a substituent. The aryl group having 6 or more and 18 or less carbon atoms, and the heteroaryl group having 3 or more and 17 or less carbon atoms may each have a halogen atom, a cyano group, an alkyl group, or an alkoxy group as a substituent. Specific examples of the alkyl group and the alkoxy group are as listed for the $Ar_1$ and the $Ar_2$. In addition, the $R_1$ and the $R_2$ may be bonded to each other to form a ring. At this time, the $R_1$ and the $R_2$ may be bonded to each other through a heteroatom, such as nitrogen, oxygen, or sulfur. In addition, the ring can have, for example, a spiro structure.

(3) $R_3$

In the general formula [1], $R_3$ is each independently selected from a hydrogen atom, a halogen atom, a cyano group, and an alkyl group, and preferably represents a hydrogen atom. Specific examples of the alkyl group are as listed for the $Ar_1$ and the $Ar_2$. The alkyl group may have a halogen atom, preferably a fluorine atom as a substituent.

(4) $Y_1$ to $Y_3$

In the general formula [1], $Y_1$ to $Y_3$ are each independently selected from a methine group and a nitrogen atom.

When any one of the $Y_1$ to the $Y_3$ represents a methine group, the methine group may have a substituent and the substituent is each independently selected from a halogen atom, a cyano group, and an alkyl group. The alkyl group may have a halogen atom, preferably a fluorine atom as a substituent. All of the $Y_1$ to the $Y_3$ may represent methine groups, or at least one of the $Y_1$ to the $Y_3$ may represent a nitrogen atom.

(5) $R_4$

In the general formula [1], $R_4$ represents an electron-withdrawing substituent independently selected from the following general formulae [1-1] and [1-2]. In each of the general formulae [1-1] and [1-2], * represents a bonding position.

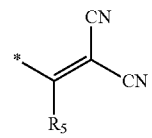

[1-1]

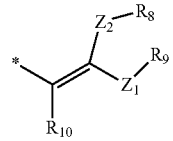

[1-2]

In the general formulae [1-1] and [1-2], $R_5$ and $R_8$ to $R_{10}$ are each independently selected from a hydrogen atom, a halogen atom, a cyano group, an amino group, an amide group, an alkyl group, an alkoxy group, an alkenyl group, an alkynyl group, an aryl group having 6 or more and 18 or less carbon atoms, and a heteroaryl group having 3 or more and 17 or less carbon atoms.

Specific examples of the alkyl group, the alkoxy group, the aryl group having 6 or more and 18 or less carbon atoms, and the heteroaryl group having 3 or more and 17 or less carbon atoms are as listed for the $Ar_1$ and the $Ar_2$.

The amino group may be, for example, an amino group in which a hydrogen atom is substituted, or any one of substituted amino groups having substituents, such as an alkyl group, an aryl group having 6 or more and 18 or less carbon atoms, and a heteroaryl group having 3 or more and 17 or less carbon atoms.

The amide group may be, for example, an amide group in which a hydrogen atom is substituted, or any one of substituted amide groups having substituents, such as an alkyl group, an aryl group having 6 or more and 18 or less carbon atoms, and a heteroaryl group having 3 or more and 17 or less carbon atoms.

The alkenyl group may be, for example, an alkenyl group in which a hydrogen atom is substituted, or any one of substituted alkenyl groups having substituents, such as a halogen atom, an alkyl group, an alkoxy group, an aryl group having 6 or more and 18 or less carbon atoms, and a heteroaryl group having 3 or more and 17 or less carbon atoms.

When the $R_5$ and the $R_8$ to the $R_{10}$ each represent any one of the amino group, the amide group, the alkyl group, the alkoxy group, the alkenyl group, the alkynyl group, the aryl group having 6 or more and 18 or less carbon atoms, or the heteroaryl group having 3 or more and 17 or less carbon atoms, the $R_5$ and the $R_8$ to the $R_{10}$ may each have a halogen atom, a cyano group, an alkyl group having 1 or more and 8 or less carbon atoms, an alkoxy group having 1 or more and 8 or less carbon atoms, an aryl group having 6 or more and 12 or less carbon atoms, or a heteroaryl group having 4 or more and 11 or less carbon atoms as a substituent.

Specific examples of the alkyl group having 1 or more and 8 or less carbon atoms, and the alkoxy group having 1 or more and 8 or less carbon atoms are as listed for the $Ar_1$ and the $Ar_2$.

Examples of the aryl group having 6 or more and 12 or less carbon atoms include a phenyl group, a naphthyl group, and a biphenyl group.

Examples of the heteroaryl group having 4 or more and 11 or less carbon atoms include a pyridyl group, a pyrazyl group, a quinolyl group, an isoquinolyl group, and a quinoxalyl group.

In addition, the $R_8$ and the $R_9$ are bonded to each other to form a ring. At this time, the $R_8$ and the $R_9$ may be bonded to each other through a heteroatom, such as nitrogen, oxygen, or sulfur. The ring formed by the bonding of the $R_8$ and the $R_9$ to each other, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur.

In the general formula [1-2], $Z_1$ and $Z_2$ are each independently selected from groups represented by the following formulae [1-3] to [1-5]. In each of the following formulae [1-3] to [1-5], * represents a bonding position. It is preferred that at least one of the $Z_1$ or the $Z_2$ represent a group represented by the formula [1-3] or the formula [1-5], and it is more preferred that both of the $Z_1$ and the $Z_2$ each represent a group represented by the formula [1-3].

[1-3]

[1-4]

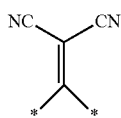

[1-5]

(6) Preferred Compound

A case in which the $R_4$ is represented by the general formula [1-2], and the $R_8$ and the $R_9$ are bonded to each other to form a ring is preferred because the lengthening of the absorption wavelength of the organic compound and an improvement in thermal stability thereof, in particular, an increase in melting point thereof are achieved, and an organic compound represented by the following general formula [2] is more preferred.

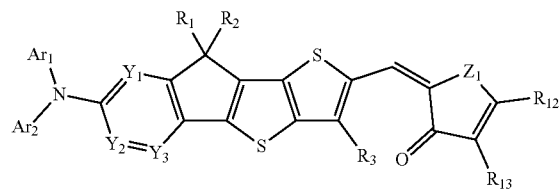

[2]

In addition, a case in which the $Z_1$ in the general formula [2] represents a carbonyl group is preferred because the thermal stability of the organic compound, in particular, the melting point thereof is high, and an organic compound represented by the following general formula [3] is more preferred.

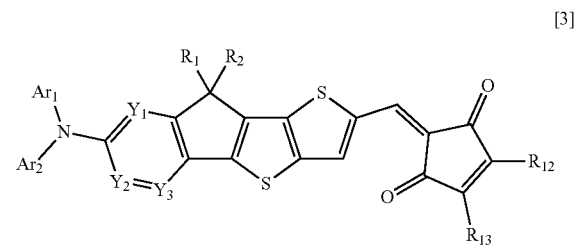

[3]

In the general formulae [2] and [3], $R_{12}$ and $R_{13}$ are each independently selected from a hydrogen atom, a halogen atom, a cyano group, an amino group, an amide group, an alkyl group, an alkoxy group, an alkenyl group, an alkynyl group, an aryl group having 6 or more and 18 or less carbon atoms, and a heteroaryl group having 3 or more and 17 or less carbon atoms. When the $R_{12}$ and the $R_{13}$ each represent any one of the amino group, the amide group, the alkyl group, the alkoxy group, the alkenyl group, the alkynyl group, the aryl group having 6 or more and 18 or less carbon atoms, or the heteroaryl group having 3 or more and 17 or less carbon atoms, the $R_{12}$ and the $R_{13}$ may each have a halogen atom, a cyano group, an alkyl group having 1 or more and 8 or less carbon atoms, an alkoxy group having 1 or more and 8 or less carbon atoms, an aryl group having 6 or more and 12 or less carbon atoms, or a heteroaryl group having 4 or more and 11 or less carbon atoms as a substituent. Specific examples of the $R_{12}$ and the $R_{13}$ are as listed for the $R_5$ and the $R_8$ to the $R_{10}$.

The $R_{12}$ and the $R_{13}$ are bonded to each other to form a ring as in the $R_8$ and the $R_9$ in the general formula [1-2]. At this time, the $R_{12}$ and the $R_{13}$ may be bonded to each other through a heteroatom, such as nitrogen, oxygen, or sulfur. The ring formed by the bonding of the $R_{12}$ and the $R_{13}$ to each other, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur. Examples of the ring formed by the bonding of the $R_{12}$ and the $R_{13}$ to each other include a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

Examples of the organic compounds represented by the general formulae [2] and [3] include compounds shown below. * represents a bonding position, and a chemical formula on the left side and any one of the chemical formulae represented by the general formulae [2-1] to [2-9] are bonded to each other at the position represented by *.

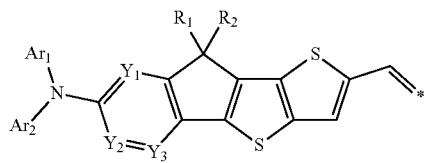

[2-1]

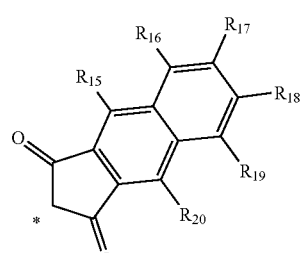

[2-2]

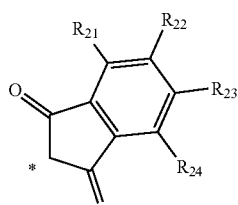

[2-3]

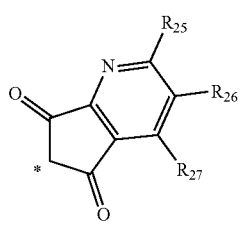

[2-4]

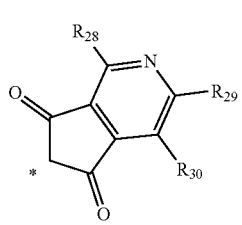

[2-5]

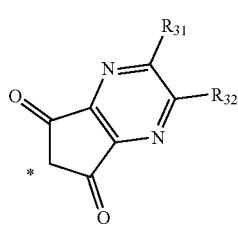

-continued

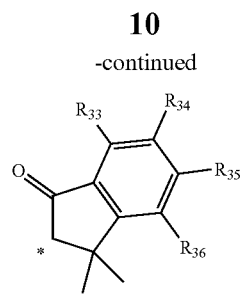

[2-6]

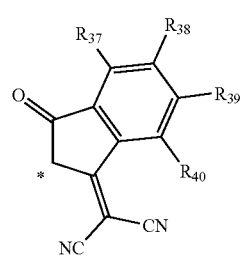

[2-7]

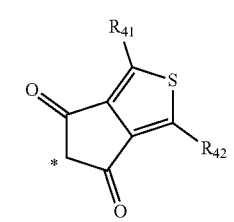

[2-8]

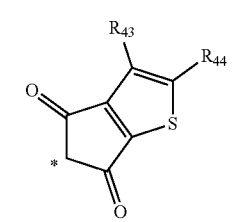

[2-9]

In the general formulae [2-1] to [2-9], $R_{15}$ to $R_{44}$ are each independently selected from a hydrogen atom, a halogen atom, a cyano group, an alkyl group having 1 or more and 8 or less carbon atoms, an alkoxy group having 1 or more and 8 or less carbon atoms, an aryl group having 6 or more and 12 or less carbon atoms, and a heteroaryl group having 4 or more and 11 or less carbon atoms. When the alkyl group having 1 or more and 8 or less carbon atoms, the alkoxy group having 1 or more and 8 or less carbon atoms, the aryl group having 6 or more and 12 or less carbon atoms, or the heteroaryl group having 4 or more and 11 or less carbon atoms has a substituent, any such group may have a substituent that the above-mentioned $Ar_1$ has.

A case in which the $R_4$ in the general formula [1] is represented by the general formula [1-1] is preferred because the molecular weight of the organic compound becomes smaller and the sublimation temperature thereof reduces, and an organic compound represented by the following general formula [4] is more preferred.

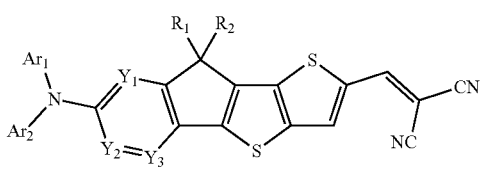

[4]

Comparison Between Exemplified Compound A1 According to Embodiment of the Present Disclosure and Comparative Compounds a-1, a-2, and b-1

Exemplified Compound A1 of the organic compound according to the embodiment of the present disclosure is represented by the following structural formula.

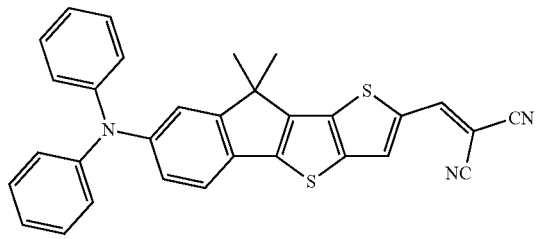

A1

Comparative Compound a-1 and Comparative Compound a-2 serving as an analog of Comparative Compound a-1 are represented by the following structural formulae.

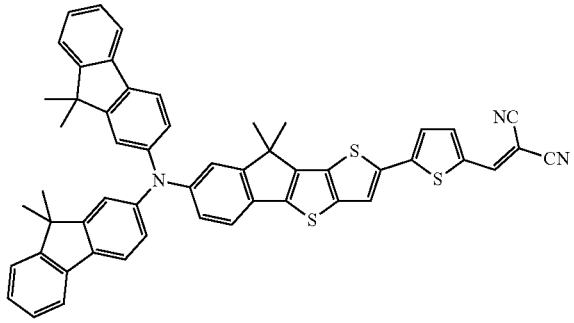

a-1

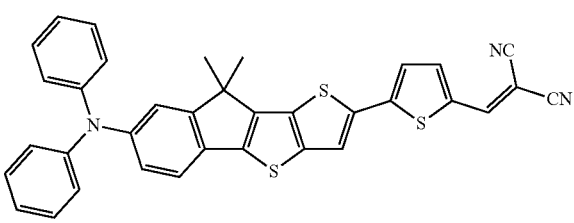

a-2

Comparative Compound b-1 is represented by the following structural formula.

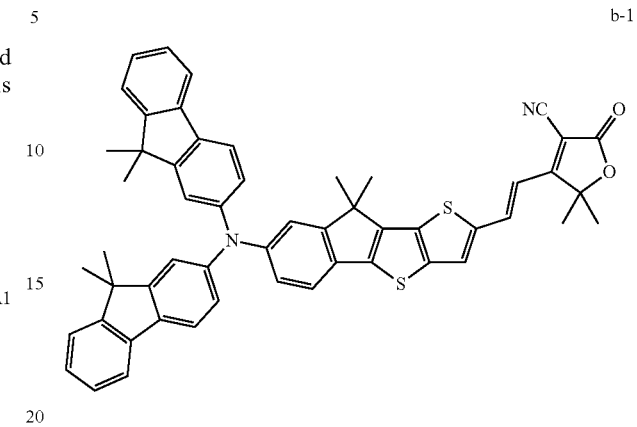

b-1

First, Exemplified Compound A1 according to the embodiment of the present disclosure, and Comparative Compounds a-1 and a-2 were compared to each other in terms of a molar extinction coefficient in a visible light absorption region. The phrase "have absorption" means that it can be confirmed that an organic compound absorbs light, and measurement noise and the like are not included in the absorbed light. The term "visible light absorption region" refers to the wavelength region of from 380 nm to 750 nm. An organic compound having light absorption in a wide range of a visible light region is preferred because the compound can be used in a photoelectric conversion element or the like.

In particular, it is preferred that an organic compound to be used in a photoelectric conversion element have absorption in a red region (of from 600 nm to 750 nm), and its sensitivity be as high as possible. The phrase "have absorption in the red region" means that when a thin film of the organic compound is formed, an end portion of the absorption spectrum of the thin film of the organic compound (the position at which the absorption spectrum rises up) is present in the red region (of 600 nm or more). When the absorption spectrum is measured in a chloroform dilute solution, the end portion of the absorption spectrum is preferably present at 580 nm or more, and is more preferably present at 600 nm or more. In addition, a maximum absorption peak wavelength when the absorption spectrum is measured in the chloroform dilute solution is preferably present at from 515 nm to 615 nm, and is more preferably present at from 535 nm to 605 nm. This is because the extent to which the compound absorbs light becomes smaller at a wavelength larger than the maximum absorption peak wavelength. Values at 550 nm are also used for comparison between the molar extinction coefficients of Exemplified Compound A1 according to the embodiment of the present disclosure and Comparative Compound a-2. The term "dilute solution" as used herein refers to a solution having a concentration of $3\times10^{-5}$ mol/l or less.

Molar extinction coefficients at maximum absorption peak wavelengths in the absorption spectra of Exemplified Compound A1 according to the embodiment of the present disclosure, and Comparative Compounds a-1 and a-2 in chlorobenzene dilute solutions ($3\times10^{-5}$ mol/l) are shown in Table 1. The molar extinction coefficient of Exemplified Compound A1 according to the embodiment of the present disclosure is higher than those of Comparative Compounds a-1 and a-2 irrespective of a substituent of an amino group. In addition, in Table 1, with regard to Exemplified Compound A1 according to the embodiment of the present disclosure and Comparative Compound a-2, molar extinction coefficients in chloroform solutions (3×10$^{-5}$ mol/l) at 550 nm were also compared to each other. Even when the comparison is performed at the same wavelength, the molar extinction coefficient of Exemplified Compound A1 according to the embodiment of the present disclosure is higher than that of Comparative Compound a-2.

disclosure is of a structure in which an arylamine moiety (—N(Ar$_1$)Ar$_2$) serving as an electron-donating group (D) and an electron-withdrawing group (A) are bonded to each other through a π-conjugated spacer skeleton in which a thienothiophene ring and an indeno group or the like are condensed with each other. The "π-conjugated spacer skeleton in which a thienothiophene ring and an indeno group or the like are condensed with each other" is hereinafter simply referred to as "π-conjugated spacer skeleton." The electron-withdrawing group (A) refers to an olefinic carbon or cyclic

TABLE 1

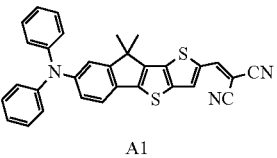 [SMILES: CC1(C)c2cc(N(c3ccccc3)c3ccccc3)ccc2-c2sc3cc(C=C(C#N)C#N)sc3c21 ; "A1"]
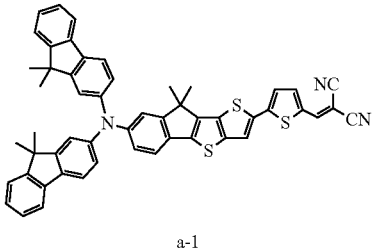 [SMILES: CC1(C)c2ccccc2-c2ccc(N(c3ccc4c(c3)C(C)(C)c3ccccc3-4)c3ccc4c(c3)C(C)(C)c3c-4sc4cc(-c5ccc(C=C(C#N)C#N)s5)sc34)cc21 ; "a-1"]
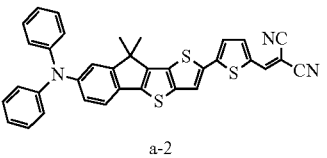 [SMILES: CC1(C)c2cc(N(c3ccccc3)c3ccccc3)ccc2-c2sc3cc(-c4ccc(C=C(C#N)C#N)s4)sc3c21 ; "a-2"]

| | A1 | a-1 | a-2 |
|---|---|---|---|
| Molar extinction coefficient at maximum absorption peak wavelength (in chlorobenzene)/ M$^{-1}$cm$^{-1}$ | 51,700 | 42,300 | 41,400 |
| Molar extinction coefficient at 550 nm (in chloroform)/ M$^{-1}$cm$^{-1}$ | 54,700 | | 37,900 |

In general, as the molar extinction coefficient of a compound becomes lower, its light absorptivity becomes lower even when the compound is in a thin film state. When the same light absorptivity as usual is to be obtained in the thin film state, the thickness of the thin film needs to be made thicker as the molar extinction coefficient becomes lower. Further, it has been known that in a photoelectric conversion element that is sandwiched between electrodes and is used by applying a voltage therebetween, when the light absorptivity of a film between the electrodes is the same as usual, as the thickness of the film becomes larger, the intensity of an electric field to be applied to the film reduces, and hence the driving voltage of the element increases. In other words, a low molar extinction coefficient leads to a reduction in efficiency or an increase in driving voltage in the photoelectric conversion element. This means that a higher molar extinction coefficient can impart a higher efficiency-improving effect or a higher driving voltage-reducing effect in the photoelectric conversion element. Therefore, when Exemplified Compound A1 according to the embodiment of the present disclosure is used in a photoelectric conversion element, the absorptivity of a film formed of the compound becomes higher than those of films formed of Comparative Compounds a-1 and a-2, and hence the element is improved in efficiency or reduced in driving voltage.

The fact that the molar extinction coefficient of the compound according to the embodiment of the present disclosure is higher than those of the comparative compounds is described together with its comparison with Comparative Compound b-1.

As represented by the general formula [1], the organic compound according to the embodiment of the present unit substituted with an electron-withdrawing group, such as a cyano group, a carbonyl group, or a halogen group, in the R$_4$.

The structural formula [5] represents a simple formula for the organic compound according to the embodiment of the present disclosure, the structural formula [6] represents a simple formula for Comparative Compound a-1, and the structural formula [7] represents a simple formula for Comparative Compound b-1. In the structural formulae [5] to [7], a portion surrounded by a dotted line represents the π-conjugated spacer skeleton, A represents the electron-withdrawing group, and D represents the electron-donating group.

As represented by the structural formula [5], the organic compound according to the embodiment of the present disclosure is free of any rotation axis between the D and the A. The absence of any rotation axis between the D and the A exhibits an improving effect on an intramolecular electronic transition probability between the D and the A. For example, when a rotation axis is present between the D and the A as represented by each of the structural formulae [6] and [7], an energy level in accordance with a rotated state is present, and hence a transition probability from the D to the A reduces. In other words, as the number of rotation axes between the D and the A becomes smaller, the transition probability becomes higher, and hence a molar extinction coefficient becomes higher. When an organic compound having a higher molar extinction coefficient is used in a photoelectric conversion layer, the absorptivity of the film (layer) becomes higher. A higher absorptivity of the film contributes to an improvement in efficiency of the element or a reduction in driving voltage thereof.

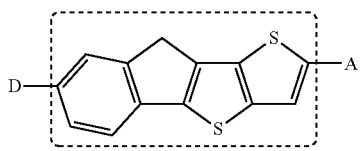

[5]

gen-carbon single bond) is as low as 352 kJ/mol, and is lower than, for example, that of C=C (a carbon-carbon double bond), that is, 607 kJ/mol. Therefore, the electron-withdrawing group unit of Exemplified Compound A1 according to the embodiment of the present disclosure is formed of a bond having high bond dissociation energy, and the electron-withdrawing group unit of Comparative Compound b-1 includes a bond having low bond dissociation energy.

TABLE 2

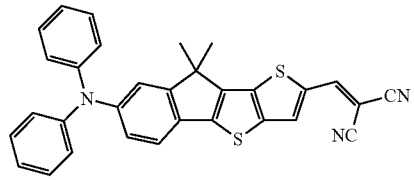

| | A1 | b-1 |
|---|---|---|
| Bond dissociation energy (kJ/mol) | C=C<br>607 | C—O<br>352 |

-continued

[6]

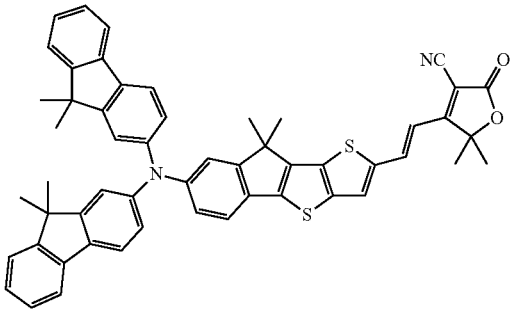

[7]

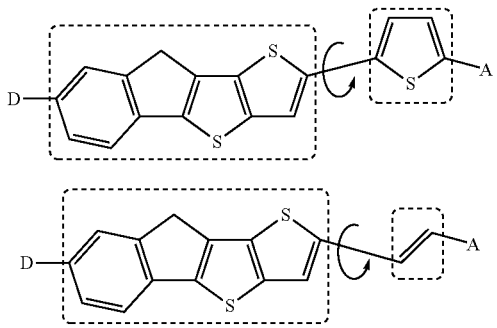

As described above, the molar extinction coefficient of Exemplified Compound A1 according to the embodiment of the present disclosure that is free of any rotation axis between the D and the A is higher than those of Comparative Compounds a-1, a-2, and b-1 each having a rotation axis between the D and the A. Therefore, when those compounds are each used in the photoelectric conversion layer of a photoelectric conversion element, Exemplified Compound A1 according to the embodiment of the present disclosure provides an improving effect on the efficiency of the element or a reducing effect on the driving voltage thereof higher than those provided by Comparative Compounds a-1, a-2, and b-1.

Further, Exemplified Compound A1 according to the embodiment of the present disclosure and Comparative Compound b-1 are compared to each other from the viewpoint of bond stability. The electron-withdrawing group unit of Comparative Compound b-1 has a cyclic ester structure. It has been known that an ester structure has high reactivity and low bond dissociation energy. As shown in Table 2, in particular, the bond dissociation energy of C—O (an oxygen-carbon single bond) is as low as 352 kJ/mol, and is lower than, for example, that of C=C (a carbon-carbon double bond), that is, 607 kJ/mol. Therefore, the electron-withdrawing group unit of Exemplified Compound A1 according to the embodiment of the present disclosure is formed of a bond having high bond dissociation energy, and the electron-withdrawing group unit of Comparative Compound b-1 includes a bond having low bond dissociation energy.

In an organic photoelectric conversion element, a process in which an organic compound responsible for photoelectric conversion receives light to generate charge from a high-energy excited state is repeatedly performed. Accordingly, when the reactivity of the organic compound responsible for the photoelectric conversion is high or the bond dissociation energy thereof is low, during the driving of the photoelectric conversion element, a bond of the compound is cleaved to reduce its light-absorbing ability, or a cleaved site serves as a charge-trapping site to reduce the efficiency of the element. In other words, the use of an organic compound having high reactivity or low bond dissociation energy in the organic photoelectric conversion element reduces the durability of the element. Therefore, Exemplified Compound A1 according to the embodiment of the present disclosure is preferred because the compound improves the durability of the element to a larger extent than Comparative Compound b-1 does.

With Regard to Properties of Organic Compound According to Embodiment of the Present Disclosure As represented by the general formula [1], the organic compound according to the embodiment of the present disclosure is of a structure in which the arylamine moiety serving as the electron-donating group (D) and the electron-withdrawing group (A) are bonded to each other through the π-conjugated spacer skeleton.

The organic compound according to the embodiment of the present disclosure has a feature in that the compound has the π-conjugated spacer skeleton and is free of any rotation axis in the π-conjugated spacer skeleton. Thus, as described above, its molar extinction coefficient increases. In addition, a π-electron or an electron related to light absorption transition is stabilized, and hence absorption is obtained at a wavelength longer than that of a compound having a rotation axis in its π-conjugated spacer skeleton. That is, the absorption sensitivity of the organic compound for red light is improved.

In addition, the organic compound has the following effect: its thermal stability is improved because the compound is free of any rotation axis between the D and the A, and hence has high planarity. The sublimation purification of the compound can be simply performed because the thermal stability is high. The sublimation purification is preferred because the sublimation purification can improve the purity of the compound. With regard to the sublimation purification, the sublimation temperature of the compound is preferably lower than its melting point. This is because when the compound is sublimated in a molten state, there is a risk that its sublimation rate significantly reduces, or part of the compound decomposes during its vapor deposition.

With Regard to Applications of Organic Compound According to Embodiment of the Present Disclosure Even when an element is produced from an organic compound having high thermal stability by using a vacuum deposition process, the element can be stably formed. In contrast, the vacuum deposition process cannot be used for a compound having low thermal stability because the compound causes thermal decomposition.

When the organic compound according to the embodiment of the present disclosure is used in a photoelectric conversion element, the organic compound according to the embodiment of the present disclosure alone can be responsible for light absorption in the entirety of the visible light region. When the number of compounds responsible for the light absorption is one, the orientation and aggregation state of the molecules of the compound can be easily controlled, and hence the occurrence of a trap level can be suppressed. In addition, when the molar extinction coefficient and light absorption sensitivity of the organic compound are high, the film thickness can be reduced, and hence the driving voltage of the element is small. In contrast, when a compound having a low molar extinction coefficient and low absorption sensitivity like the comparative compounds is used in the element, several kinds of compounds need to be mixed, or the thickness needs to be increased in order that the compound may be caused to absorb light. When the thickness is increased, the driving voltage increases and the risk that the trap level occurs becomes higher. When the trap level occurs, an increase in driving voltage due to a reduction in conversion efficiency of the element occurs. Therefore, a case in which the thickness is increased is not preferred because the driving voltage of the element is high.

When the organic compound according to the embodiment of the present disclosure is used in a photoelectric conversion element, an n-type semiconductor, such as a fullerene analog, is preferably used as an electron acceptor together with the compound. Specifically, the photoelectric conversion layer of the element preferably contains the organic compound according to the embodiment of the present disclosure, and the fullerene analog. When used together with the fullerene analog, the organic compound according to the embodiment of the present disclosure can be improved in light absorption sensitivity particularly at shorter wavelengths ranging from 380 nm to 500 nm. Thus, its panchromatic performance becomes satisfactory. The panchromatic performance refers to such an ability that the compound has high light absorption sensitivity in the entirety of the visible light region. When used in the photoelectric conversion layer together with the n-type semiconductor, such as the fullerene analog, the organic compound according to the embodiment of the present disclosure functions as an electron donor to perform satisfactory photoelectric conversion. In other words, when the layer contains both the organic compound according to the embodiment of the present disclosure and the n-type semiconductor, the layer can have an excellent photoelectric conversion characteristic in the entirety of the visible light region by virtue of the panchromatic performance and the satisfactory photoelectric conversion characteristic.

As described above, the organic compound according to the embodiment of the present disclosure is a compound that has a high molar extinction coefficient, that has light absorption in a wide range of the visible light region, and that has high thermal stability, and hence the compound can be preferably used in a photoelectric conversion element. In addition, a photoelectric conversion element including the organic compound according to the embodiment of the present disclosure can achieve a photoelectric conversion element that has high vacuum deposition process stability, that can be driven at a low voltage, and that has high efficiency in the entirety of the visible light region.

In addition, when at least one of the $Y_1$ to the $Y_3$ in the general formula [1] represents a nitrogen atom, the HOMO of the compound becomes deeper (more distant from its vacuum level), and hence the compound exhibits a larger dark current-suppressing effect when used in a photoelectric conversion element. The reason for the foregoing is described below.

The application of a voltage in the photoelectric conversion element may flow a current even when the element is not irradiated with light. Unlike the case of a solar cell, the dark current becomes a large problem in terms of the characteristics of the element. One possible cause for the occurrence of the dark current is as follows: an interaction between the HOMO of a molecule that absorbs light to be excited and the LUMO of each of an n-type semiconductor, such as a fullerene analog, which accelerates photoelectric separation, and a peripheral charge-blocking layer is caused only by the application of a dark-time voltage, and hence the dark current occurs in the photoelectric conversion layer of the element. This is because the LUMO levels of the n-type semiconductor, such as the fullerene analog, and the peripheral charge-blocking layer are deep (distant from their vacuum levels) and approach the HOMO level of the molecule that absorbs light to be excited, and as a result, charge transfer between the two molecules becomes liable to occur.

The inventors have conceived, as a method of reducing the dark current without reducing the photoelectric conversion efficiency of the element, selective deepening of the HOMO of the molecule that absorbs light to be excited for reducing the HOMO-LUMO interaction between the two molecules.

The compound according to the embodiment of the present disclosure is a molecule that absorbs light to be excited, and when at least one of the $Y_1$ to the $Y_3$ represents a nitrogen atom, the compound is of a structure in which an amino group is bonded onto a nitrogen-containing heterocycle serving as a π-electron-deficient system. The vicinity of the amino group is responsible mainly for the HOMO of the molecule, and the vicinity of an electron-withdrawing moiety represented by the $R_4$ in the general formula [1] is responsible mainly for the LUMO of the molecule. Accordingly, the HOMO level of the molecule varies depending on the properties of a substituent to which the amino group is bonded. In the embodiment of the present disclosure, in the compound in which at least one of the $Y_1$ to the $Y_3$ in the general formula [1] represents a nitrogen atom, the amino group and the nitrogen-containing heterocycle serving as a π-electron-deficient system are bonded to each other. Accordingly, electrons near the amino group that is electron-rich are stabilized, and as a result, the HOMO level deepens. In other words, only the HOMO level can be deepened without any influence on the LUMO level of the molecule.

Therefore, when the organic compound according to the embodiment of the present disclosure in which at least one of the $Y_1$ to the $Y_3$ in the general formula [1] represents a nitrogen atom is used as the photoelectric conversion layer of an organic photoelectric conversion element, the dark current can be suppressed without any reduction in photoelectric conversion efficiency of the element.

Examples of Organic Compound According to Embodiment of the Present Disclosure

Specific structural formulae of the organic compound according to the embodiment of the present disclosure are listed below. However, the present disclosure is not limited to these specific examples.

A1

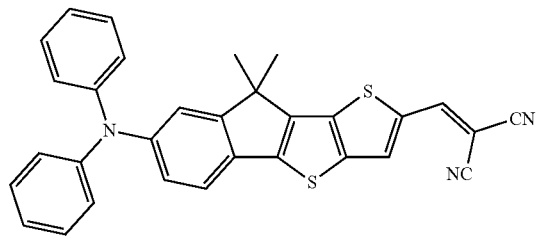

A2

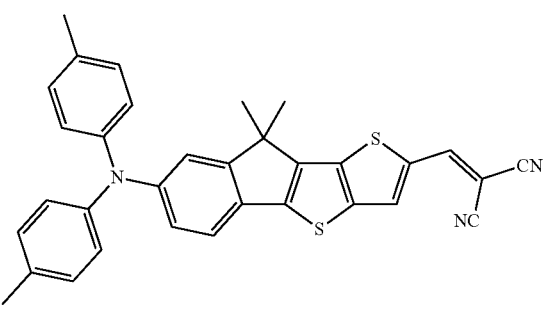

A3

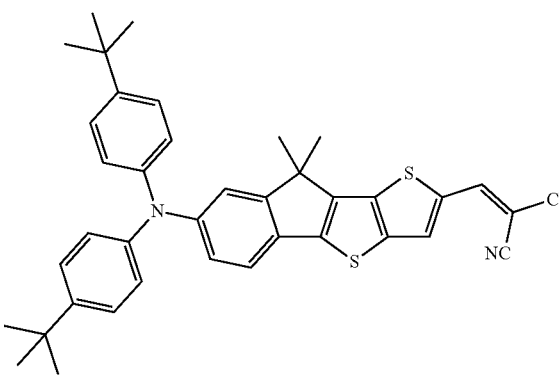

A4

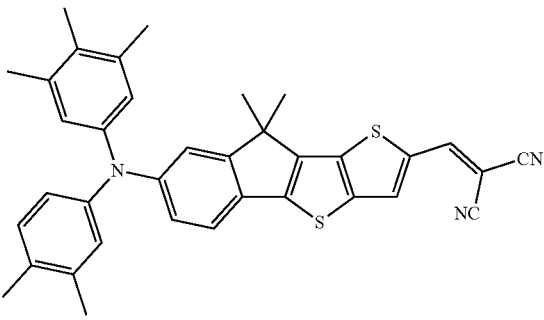

A5

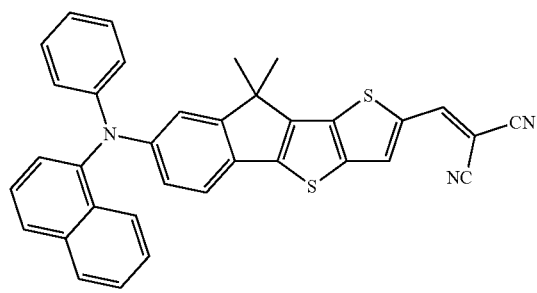

A6

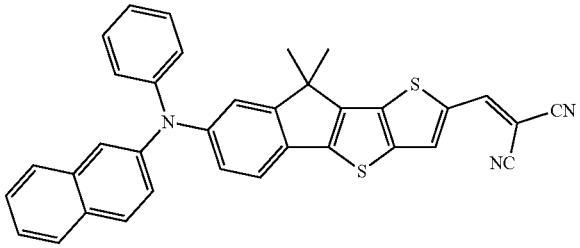

A7

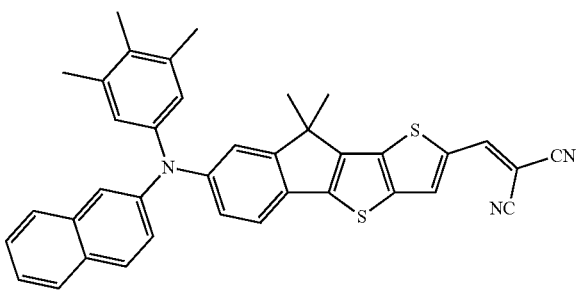

A8

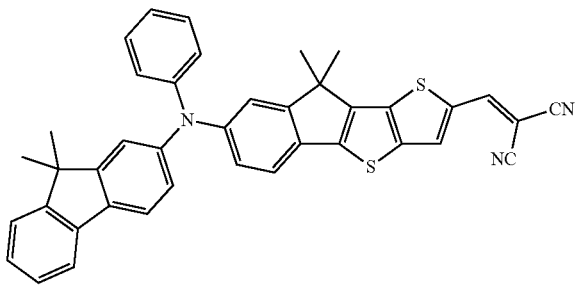

A9
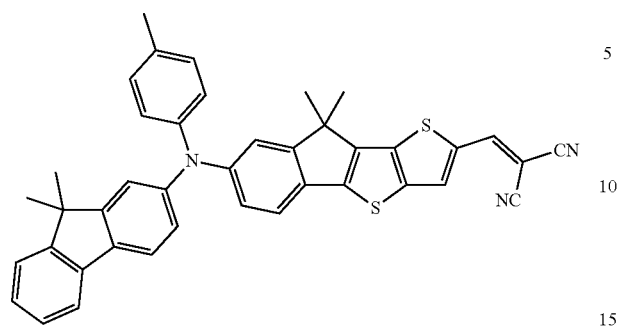
A10
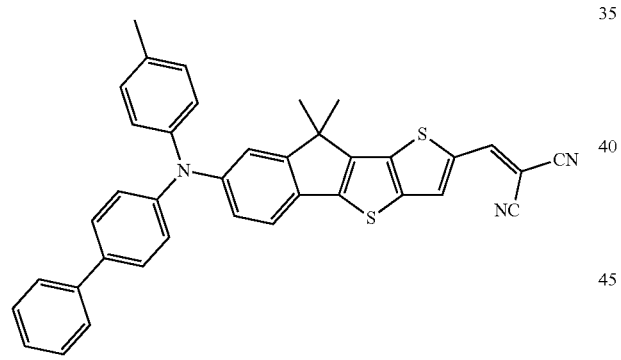
A11
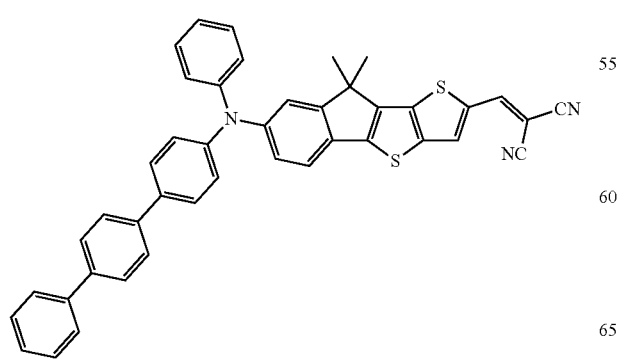
A12
A13
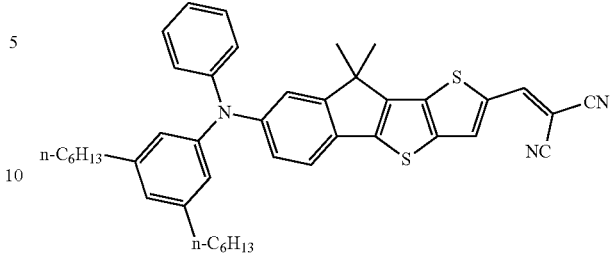
A14
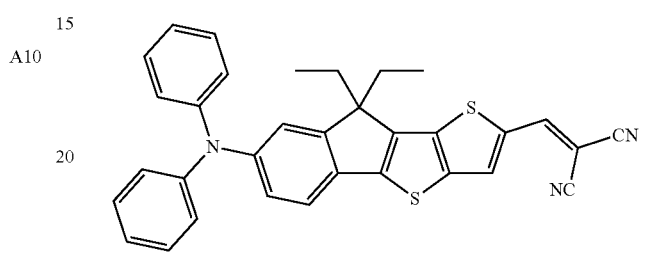
A15
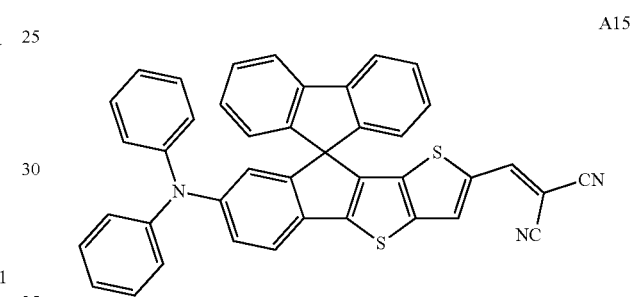
A16
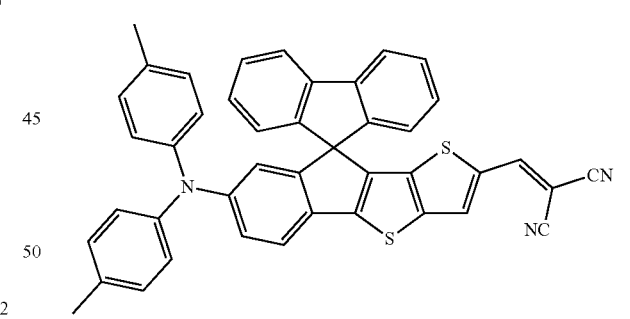
A17
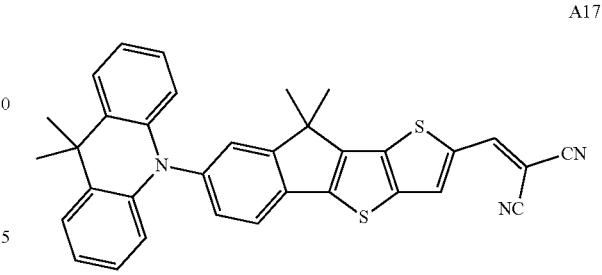

A18
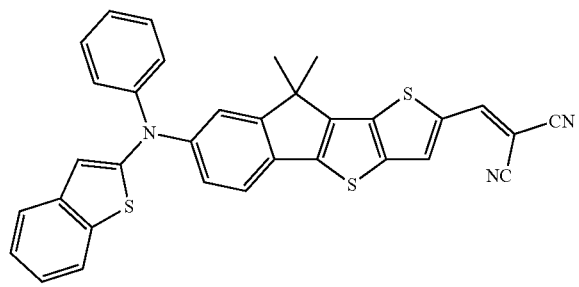
A19
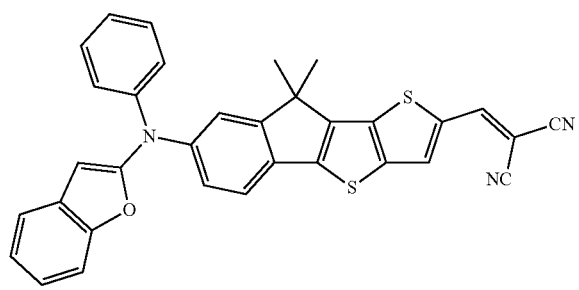
A20
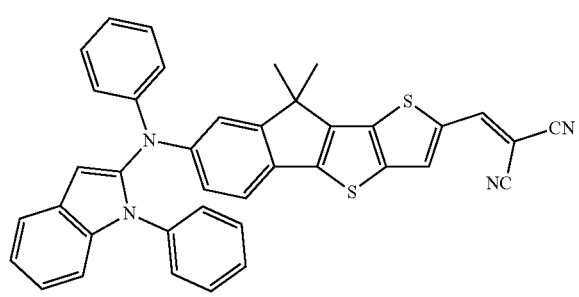
A21
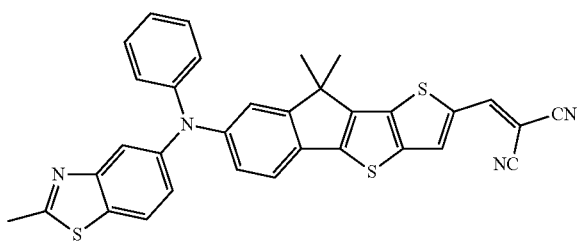
A22
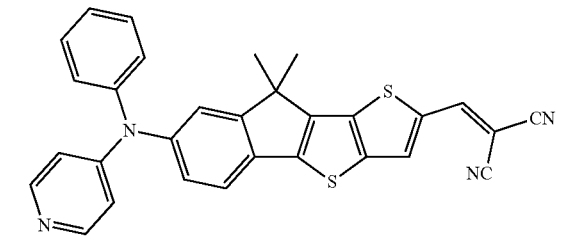
A23
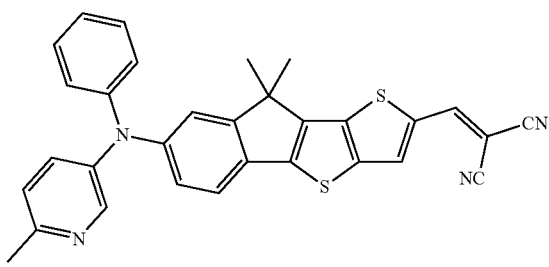
A24
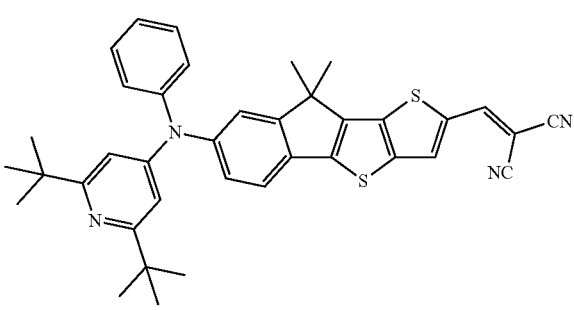
A25
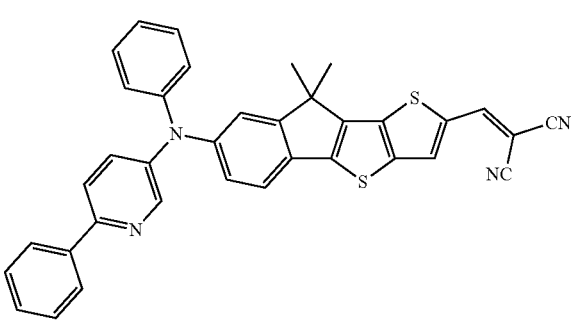
A26
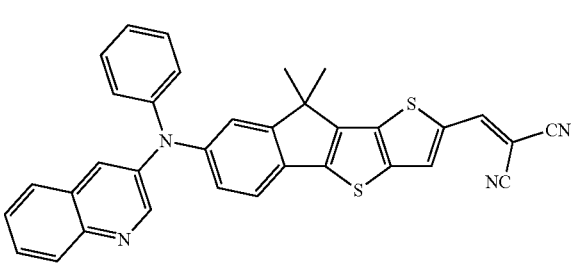
A27
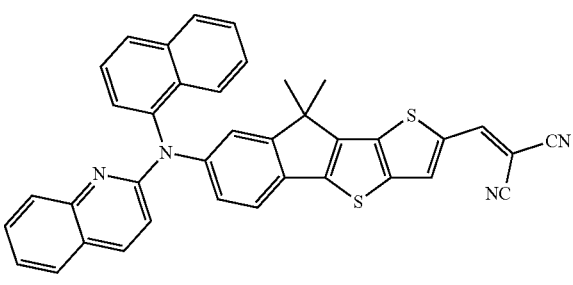

AA1
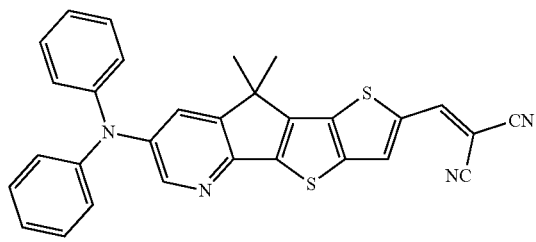
AA2
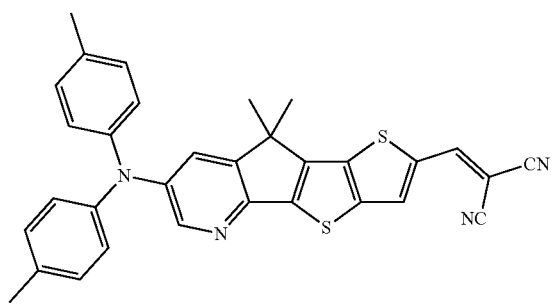
AA3
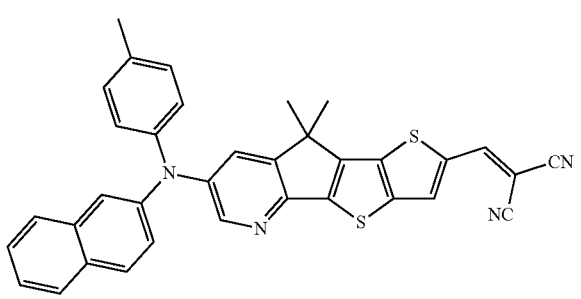
AA4
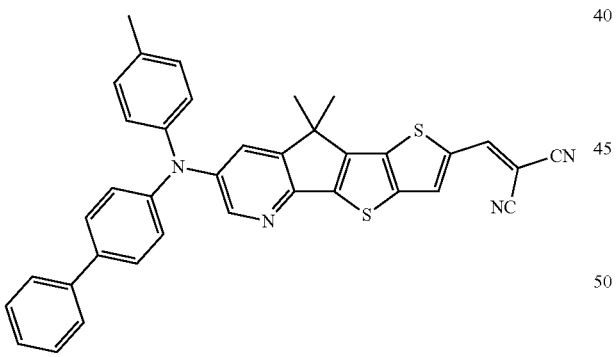
AA5
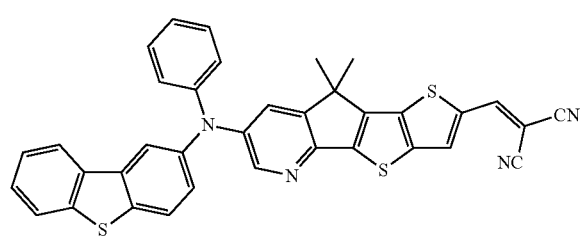
AA6
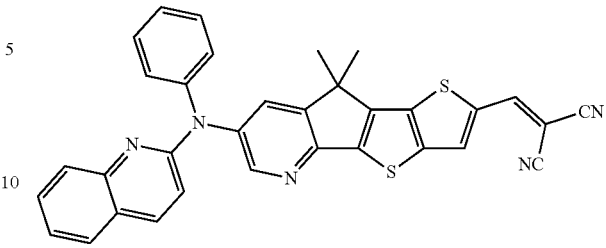
AA7
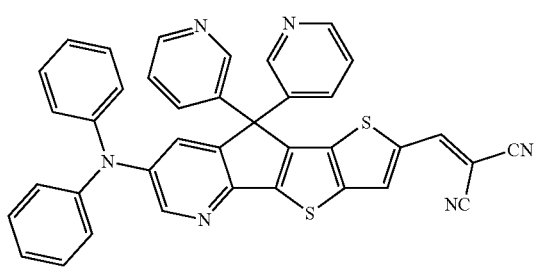
AA8
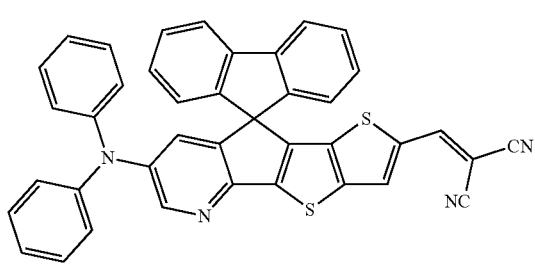
AA9
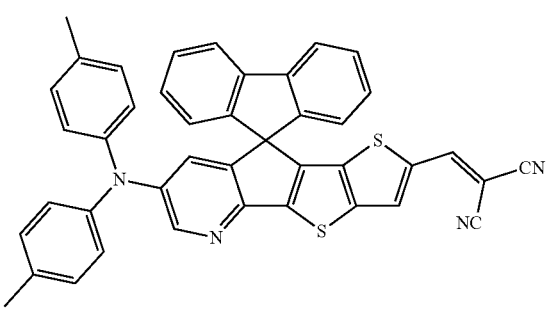
AB1
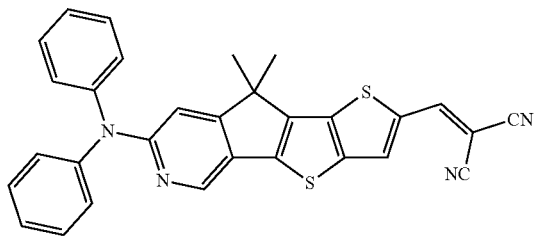

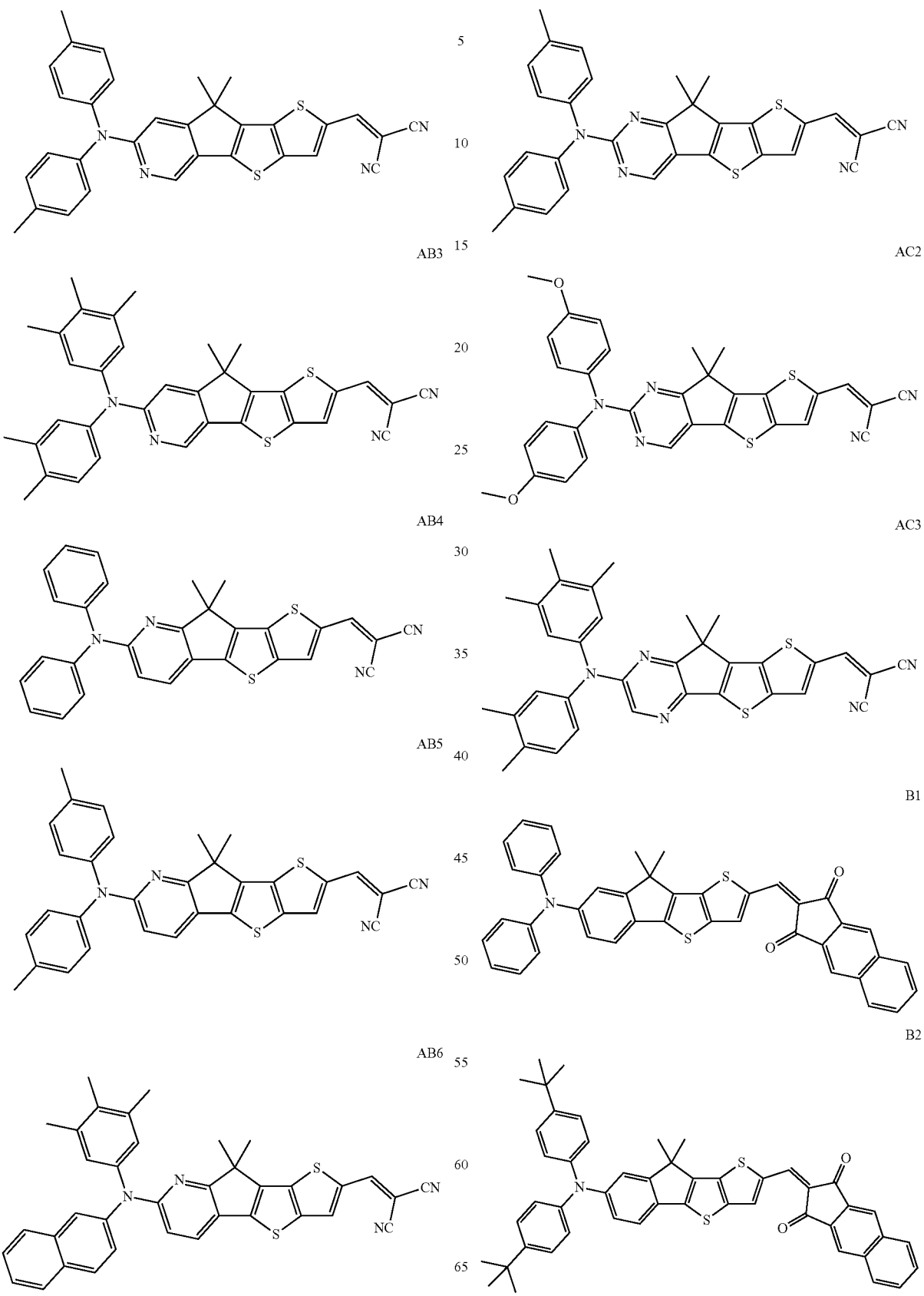

B3
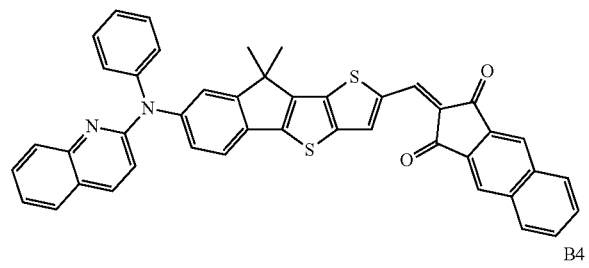
B4
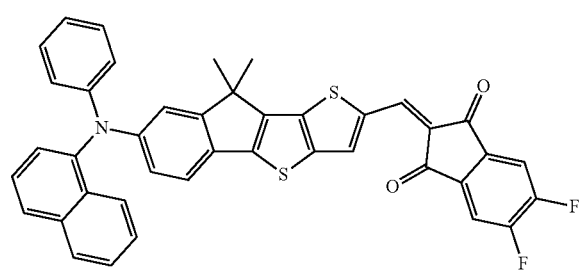
B5
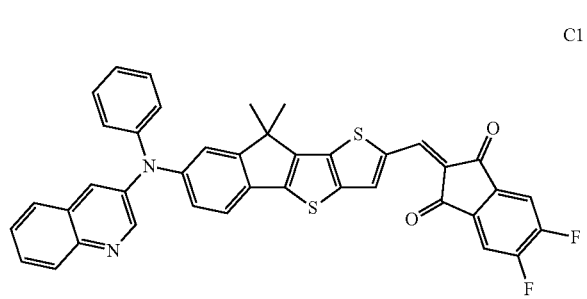
C1
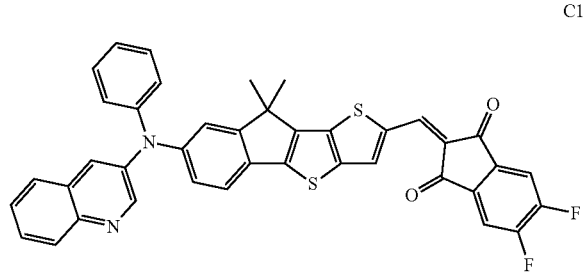
C3
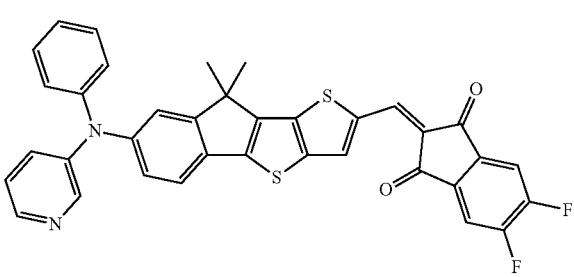
C4
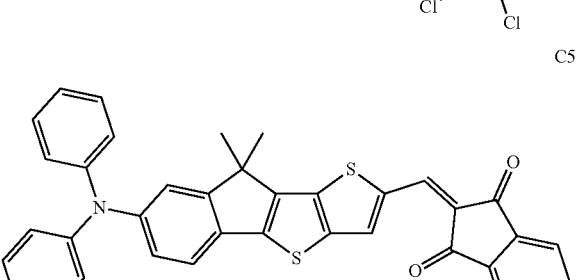
C5
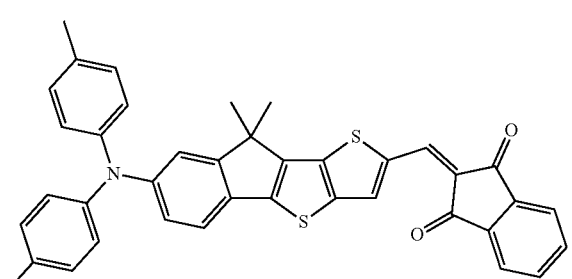
C6
C2
C7

C8
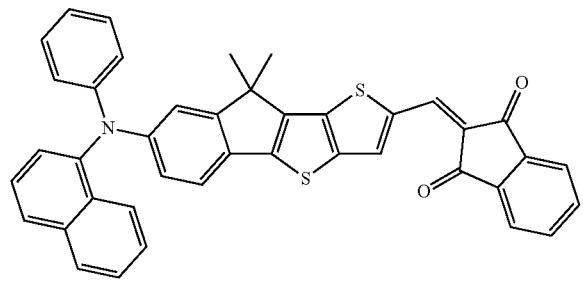
C9
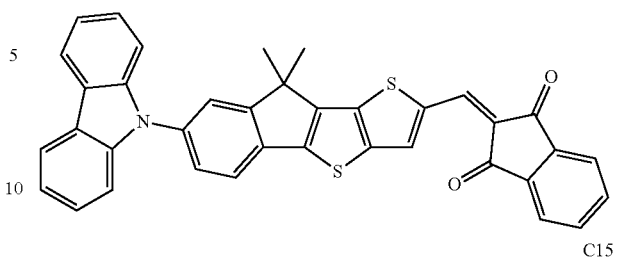
C10
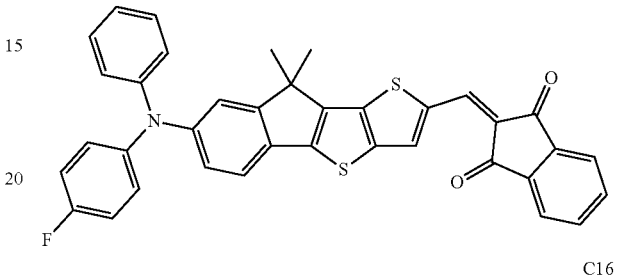
C11
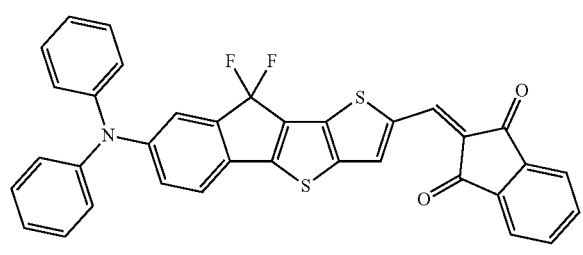
C12
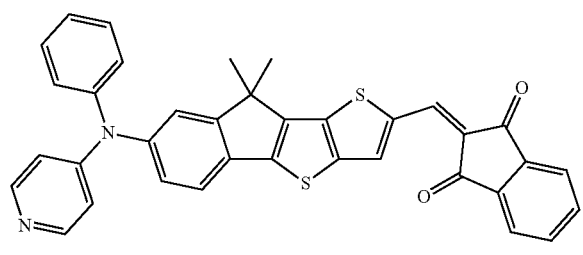
C13
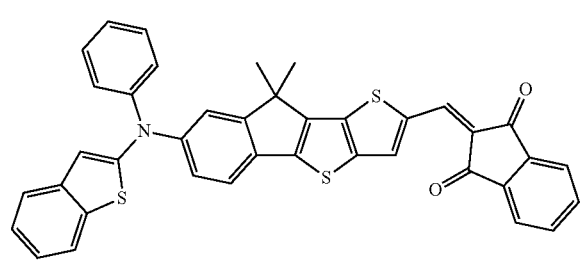
C14
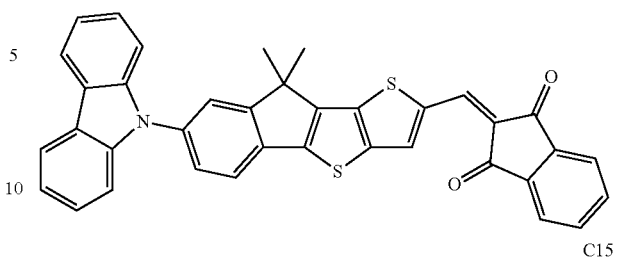
C15
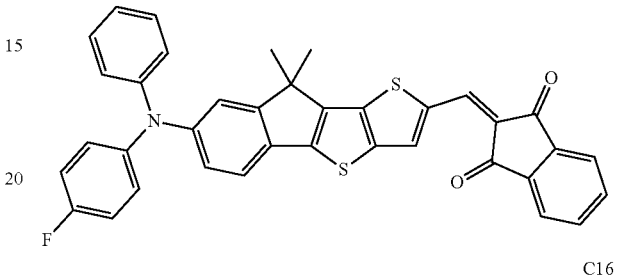
C16
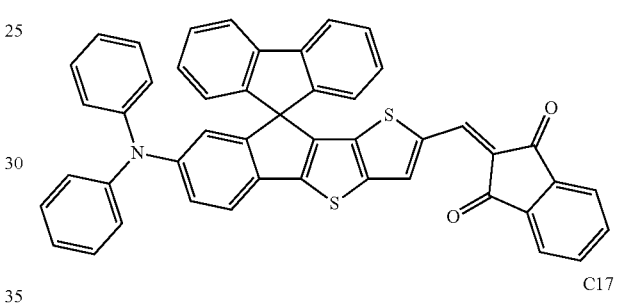
C17
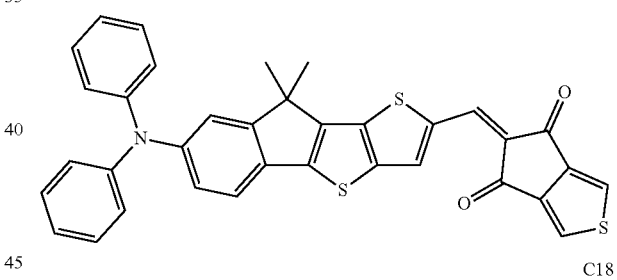
C18
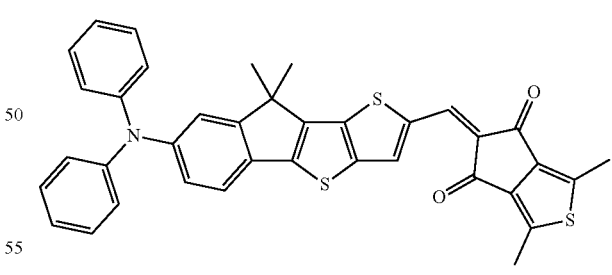
C19
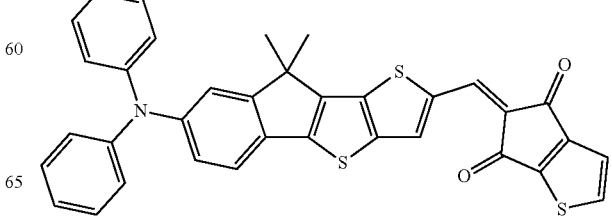

33
-continued
C20
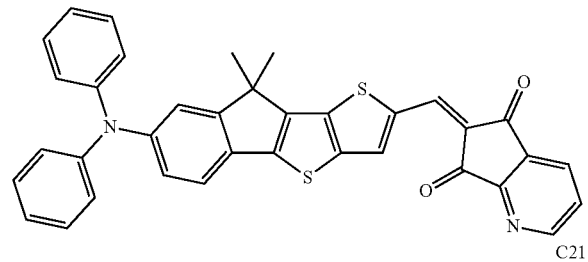
C21
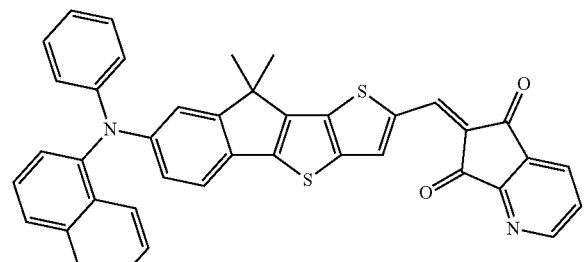
C22
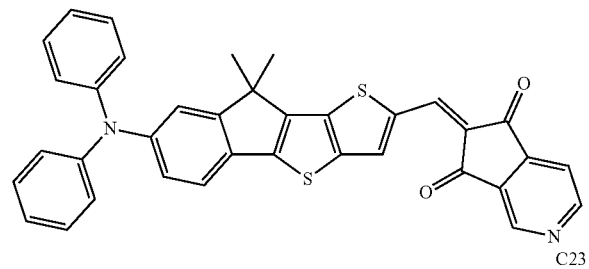
C23
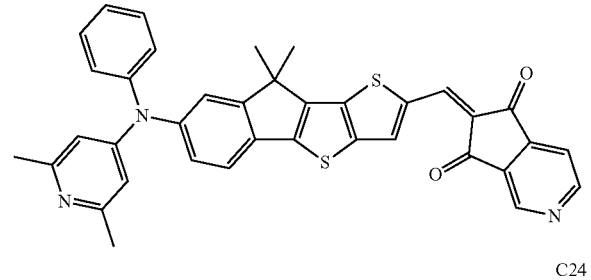
C24
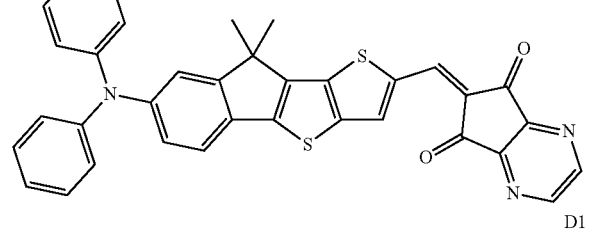
34
-continued
D2
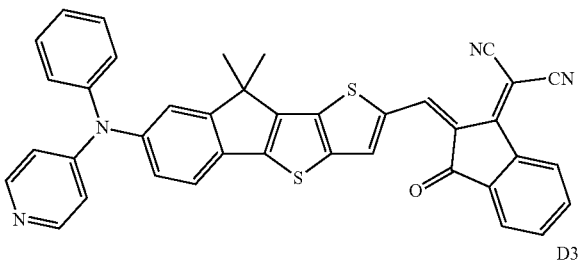
D3
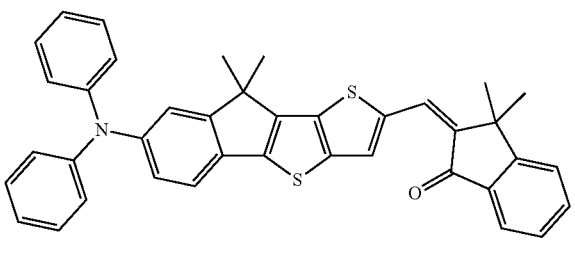
D4
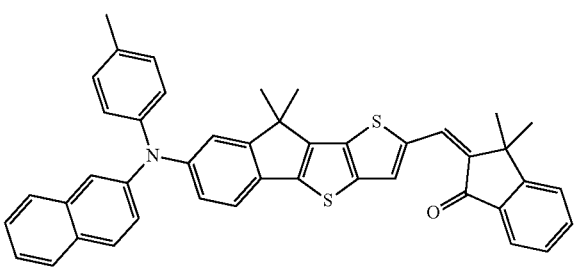
D5
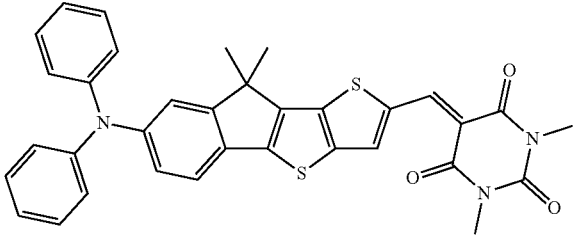
D6
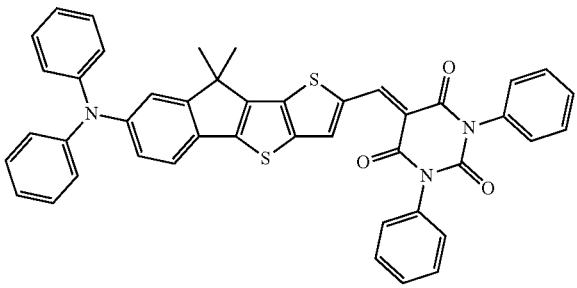

D7
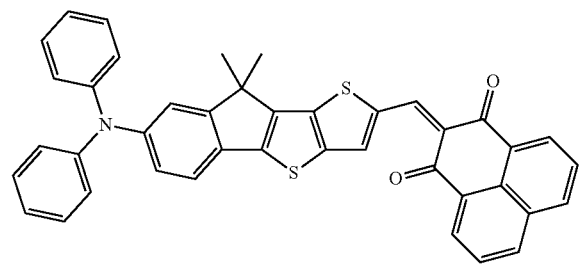
BB2
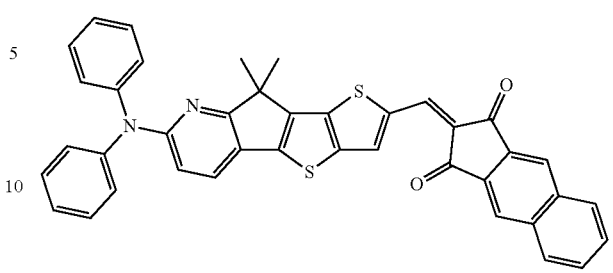
BA1
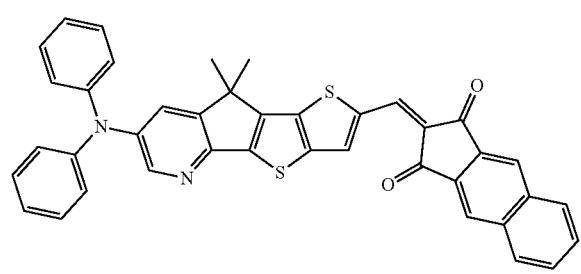
BC1
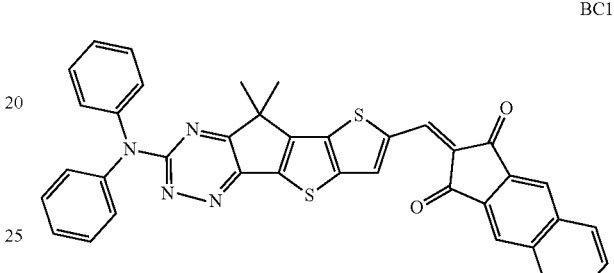
BA2
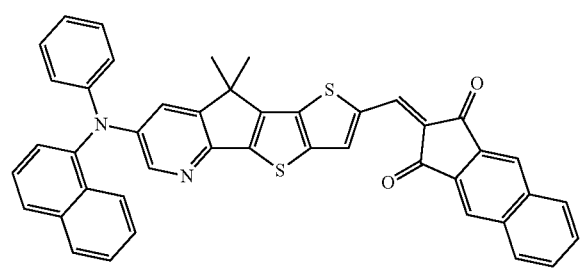
CA1
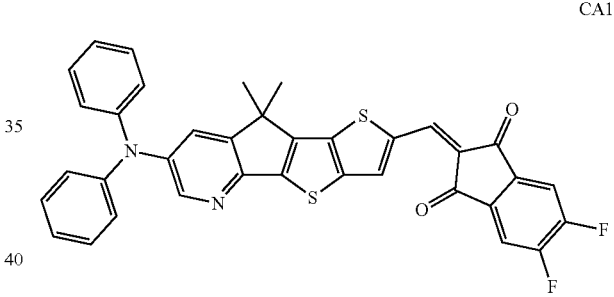
BA3
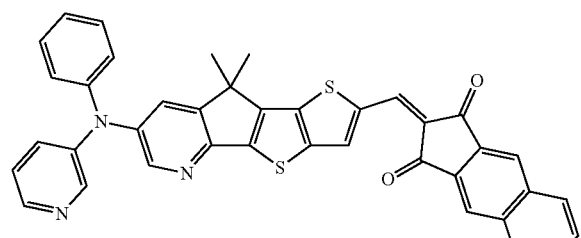
CA2
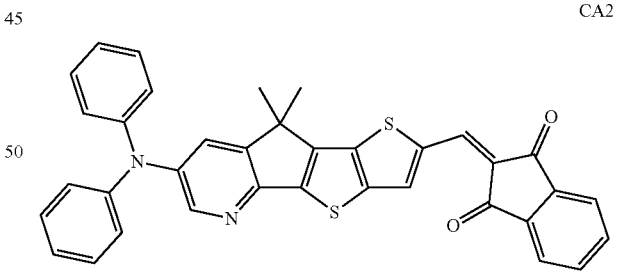
BB1
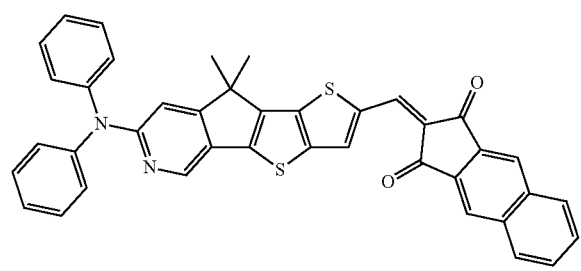
CA3
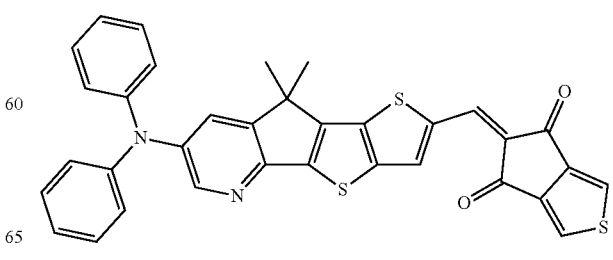

CA4
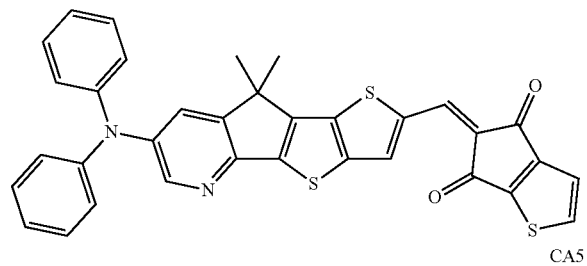
CB4
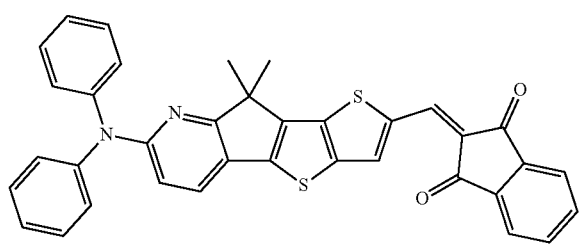
CA5
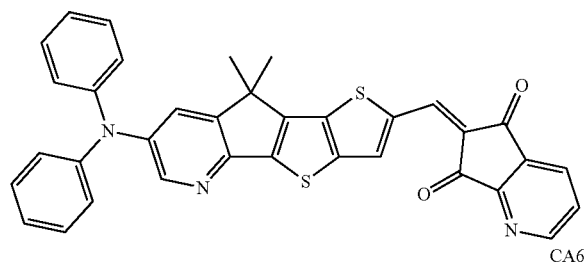
CB5
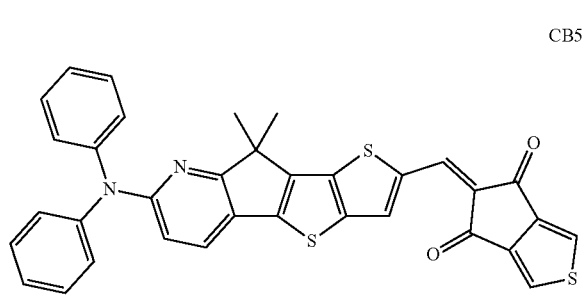
CA6
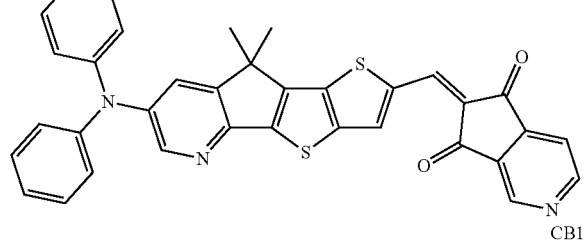
CC1
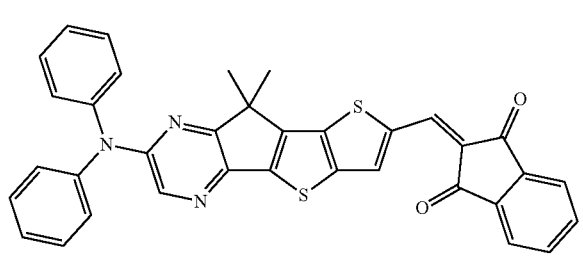
CB1
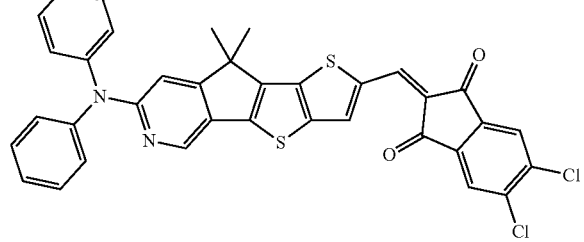
CC2
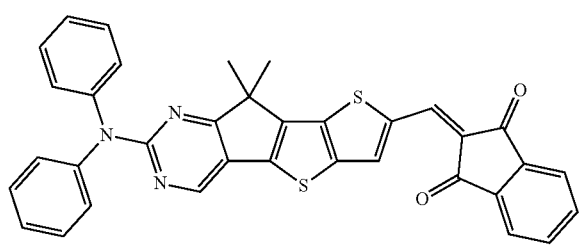
CB2
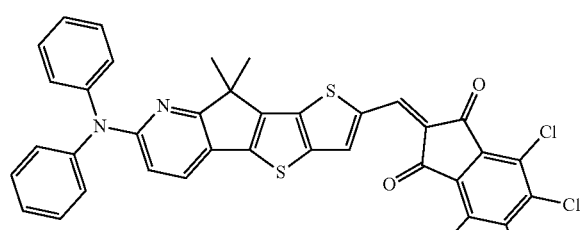
CC3
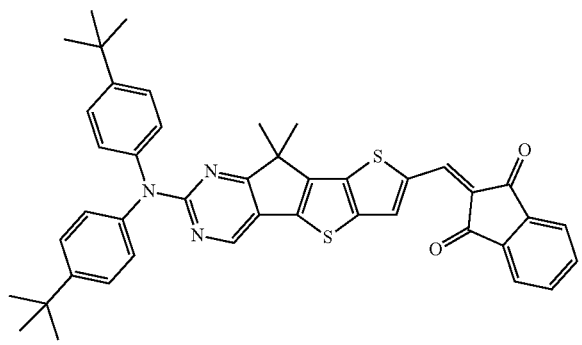
CB3
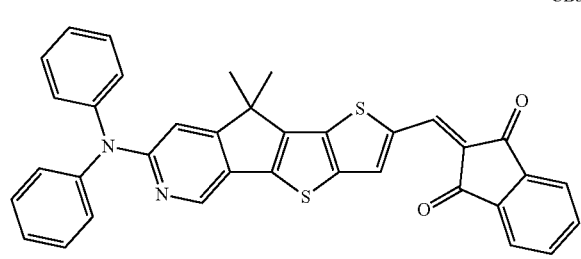

CC4

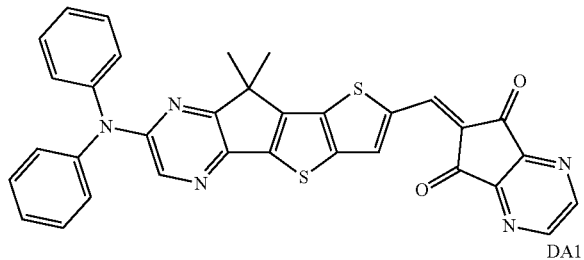

DA1

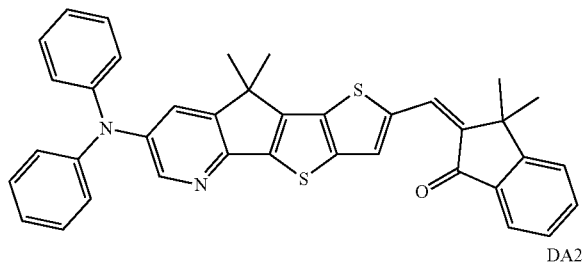

DA2

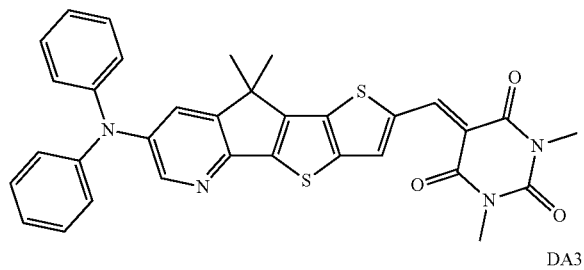

DA3

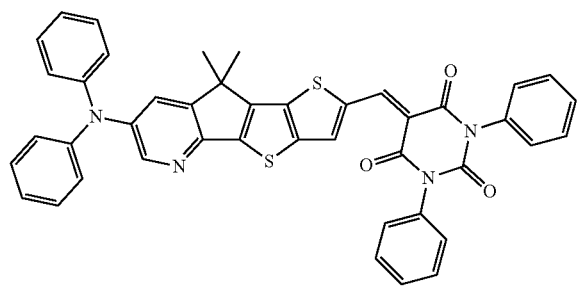

DA4

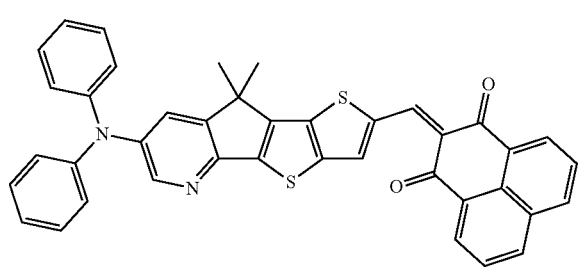

DB1

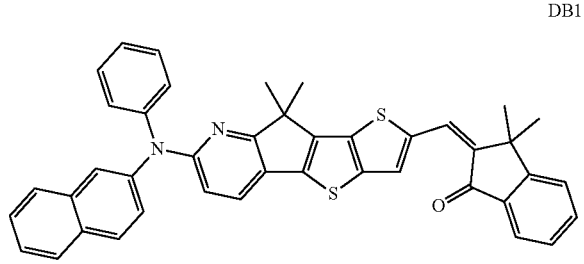

DC1

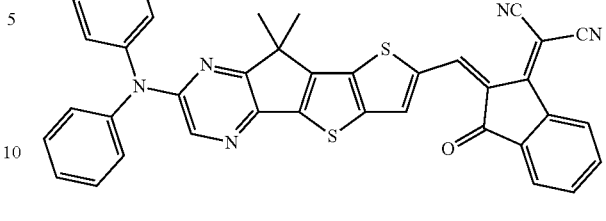

(1) Group A and Groups AA to AC

The compounds shown in the group A and the groups AA to AC are each a compound in which the $R_4$ in the general formula [1] corresponds to the general formula [1-1]. Of the compounds according to the embodiment of the present disclosure, the compounds have small molecular weights and hence can be sublimated at low temperatures.

(2) Groups B to D, Groups BA to BC, Groups CA to CC, and Groups DA to DC

The compounds shown in the groups B to D, the groups BA to BC, the groups CA to CC, and the groups DA to DC are examples of a compound in which the $R_4$ in the general formula [1] corresponds to the general formula [1-2]. Of the compounds according to the embodiment of the present disclosure, those compounds are each a compound that has high absorption sensitivity for red light and that has high photoelectric conversion efficiency in the red region. In addition, in the case of a compound in which the $R_3$ in the general formula [1] represents a hydrogen atom and the $R_4$ has carbonyl oxygen, the melting point of the compound is increased by an effect of an intramolecular hydrogen bond between the hydrogen atom represented by the $R_3$ and the carbonyl oxygen of the $R_4$. Accordingly, the Δ temperature (sublimation temperature-melting point) of the compound increases, and hence the compound has high thermal stability and high vapor deposition stability.

Of those, the compounds shown in the group B, the group C, the groups BA to BC, and the groups CA to CC are each a compound represented by the general formula [3] in which the $R_4$ has two carbonyl groups. Of the compounds according to the embodiment of the present disclosure, the compounds each have a high melting point, high thermal stability, and high vapor deposition stability because the compounds are each improved in symmetry.

The compounds shown in the group B (excluding B4 and B5) and the groups BA to BC are each a compound in which the $R_4$ in the general formula [1] has a benzoindandione derivative skeleton. Of the compounds according to the embodiment of the present disclosure, the compounds each have high absorption sensitivity in the red region.

The compounds shown in the group C and the groups CA to CC are each a compound in which the $R_4$ in the general formula [1] has an indandione derivative skeleton. Of the compounds according to the embodiment of the present disclosure, the compounds each have satisfactory absorption sensitivity in the red region and high vapor deposition stability.

(3) Groups AA to AC, Groups BA to BC, Groups CA to CC, and Groups DA to DC

The compounds shown in the groups AA to AC, the groups BA to BC, the groups CA to CC, and the groups DA to DC are each a compound having a nitrogen-containing heterocycle in its π-conjugated spacer skeleton. Those compounds are compounds having HOMO's deeper than that in the case where a π-conjugated spacer skeleton is free of any nitrogen atom by virtue of an effect of the nitrogen-containing heterocycle serving as a π-electron-deficient system. A compound having a deep HOMO is preferred because the compound exhibits a high dark current-suppressing effect when used in a photoelectric conversion element. As long as at least one of the $Y_1$ to the $Y_3$ in the general formula [1] represents a nitrogen atom, a HOMO-deepening effect is obtained irrespective of the number and positions of nitrogen atoms, and the molar extinction coefficient of a compound to be obtained is high as in the compounds shown in the group A to the group D.

The compounds shown in the group AA, the group BA, the group CA, and the group DA are each a compound in which the $Y_3$ in the general formula [1] represents a nitrogen atom, and the $Y_1$ and the $Y_2$ therein represent carbon atoms. Of the compounds according to the embodiment of the present disclosure, the compounds each have more satisfactory absorption sensitivity in the red region.

The compounds shown in the group AB, the group BB, the group CB, and the group DB are each a compound in which one of the $Y_1$ and the $Y_2$ in the general formula [1] represents a nitrogen atom. Of the compounds according to the embodiment of the present disclosure, the compounds have high molar extinction coefficients because a nitrogen atom in the π-conjugated spacer skeleton of each of the compounds is arranged next to a substitution position to which an amino group is bonded, and hence a dipole moment in a molecule of the compound becomes higher.

The compounds shown in the group AC, the group BC, the group CC, and the group DC are each a compound in which two or more of the $Y_1$ to the $Y_3$ in the general formula [1] represent nitrogen atoms. Of the compounds according to the embodiment of the present disclosure, the compounds have deep HOMO's because a heterocycle containing two or more nitrogen atoms serves as a system that is more electron-deficient than a heterocycle containing one nitrogen atom is.

Method of Synthesizing Organic Compound According to Embodiment of the Present Disclosure Next, a method of synthesizing the organic compound according to the embodiment of the present disclosure is described.

(A) Compound in which all of $Y_1$ to $Y_3$ Represent Methine Groups

A π-conjugated spacer skeleton can be synthesized in accordance with, for example, a synthesis scheme represented by the following formula [8].

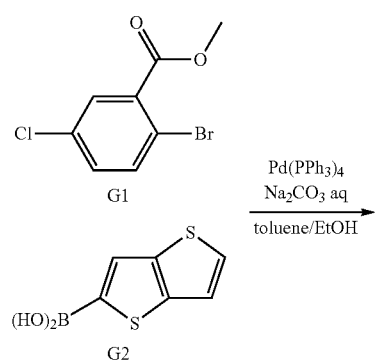

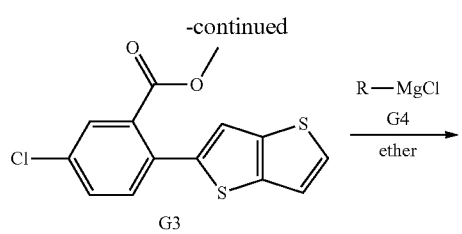

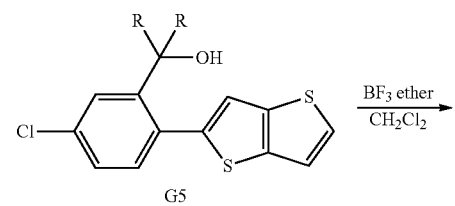

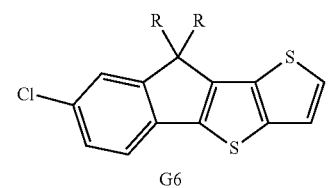

Specifically, the skeleton is synthesized by sequentially performing the following reactions (1) to (3).

(1) G3 can be synthesized by a cross-coupling reaction between a thienothiophene boron compound (G2) and G1 with a Pd catalyst.

(2) G5 can be synthesized by a nucleophilic addition reaction on the carbonyl group of the G3 with a Grignard reagent (G4). With regard to the G4, when R represents an alkyl group, the G5 can be similarly synthesized with various Grignard reagents. In the case of fluorine substitution, the G5 can be synthesized by, for example, using thionyl chloride and pyridine as reagents to be caused to react with the carbonyl group.

(3) G6 can be synthesized by the intramolecular cyclization reaction of the G5 with a Lewis acid or an acid.

When synthesis is performed by using the basic skeleton (G6) in accordance with a synthesis scheme represented by the following formula [9], the organic compound according to the embodiment of the present disclosure can be synthesized.

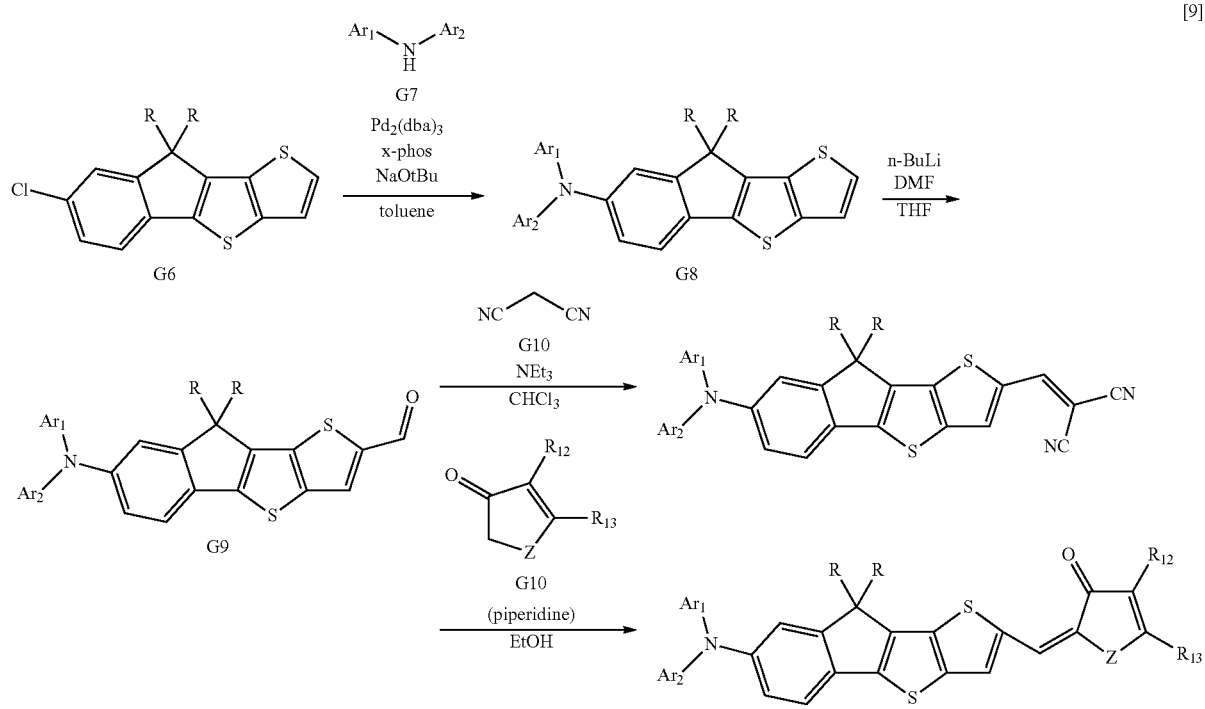

Specifically, the compound is synthesized by sequentially performing the following reactions (1) to (3).

(1) G8 can be synthesized by a cross-coupling reaction between the basic skeleton (G6) and an amine (G7) with a Pd catalyst.

(2) G9 can be synthesized by the formylation reaction of the G8 with n-butyllithium.

(3) The organic compound according to the embodiment of the present disclosure can be synthesized by Knoevenagel condensation between the G9 and G10. The organic compound according to the embodiment of the present disclosure can be similarly synthesized by changing the G10 to such a compound as represented by the following general formula [10]. $R_{53}$ to $R_{60}$ are each independently selected from a hydrogen atom, a halogen atom, an alkyl group, an aryl group, and a heteroaryl group.

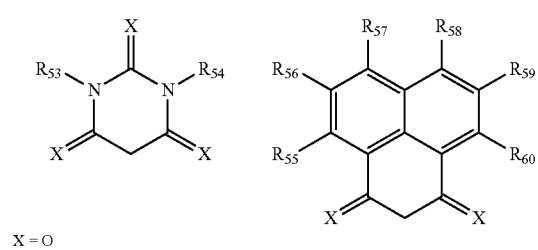

X = O

In addition, various compounds can be synthesized by changing the G6, the G7, and the G10. Specific examples thereof are shown in Tables 3 to 5.

TABLE 3

| | G6 | G7 | G10 | Exemplified Compound No. |
|---|---|---|---|---|
| 1 | (structure) | (structure) | NC–CN | A3 |
| 2 | (structure) | (structure) | NC–CN | A4 |

TABLE 3-continued
| | G6 | G7 | G10 | Exemplified Compound No. |
|---|---|---|---|---|
| 3 | 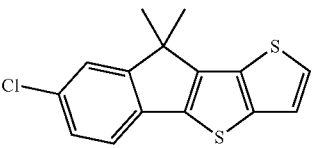 | 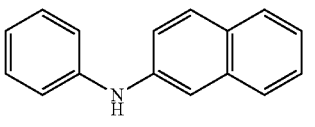 |  | A6 |
| 4 | 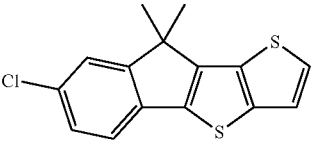 | 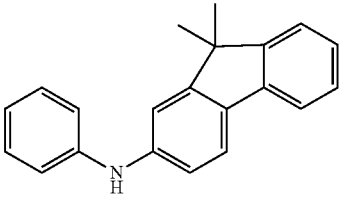 |  | A8 |
| 5 | 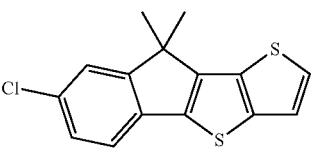 | 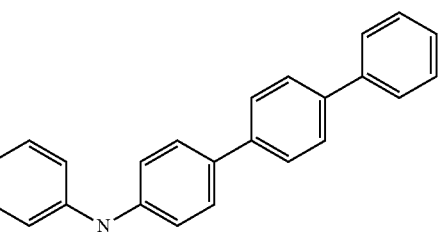 | 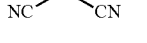 | A12 |
| 6 | 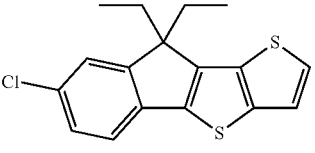 | 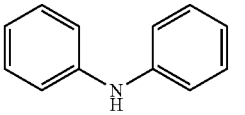 |  | A14 |
| 7 | 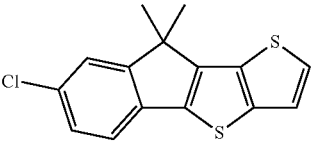 | 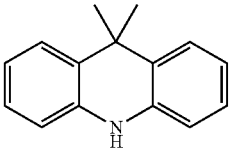 |  | A17 |
| 8 | 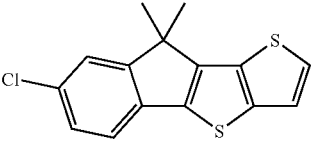 | 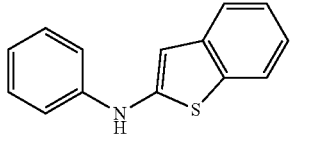 |  | A18 |
TABLE 4
| | G6 | G7 | G10 | Exemplified Compound No. |
|---|---|---|---|---|
| 9 | 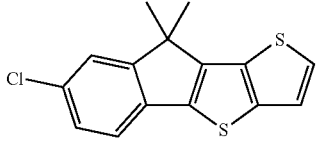 | 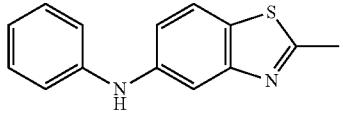 | 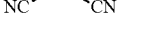 | A21 |

TABLE 4-continued
| | G6 | G7 | G10 | Exemplified Compound No. |
|---|---|---|---|---|
| 10 | 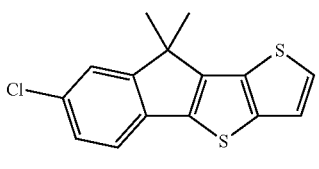 | 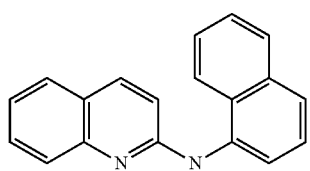 | 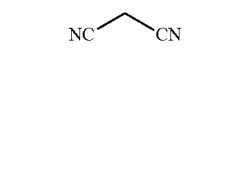 | A27 |
| 11 | 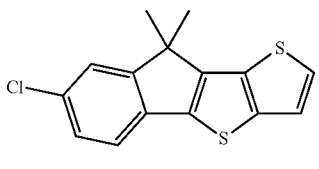 | 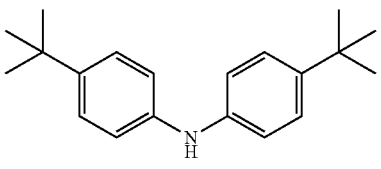 | 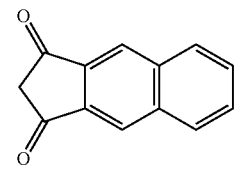 | B2 |
| 12 | 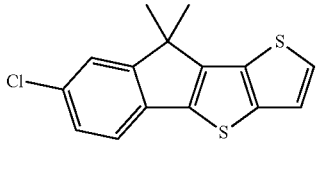 | 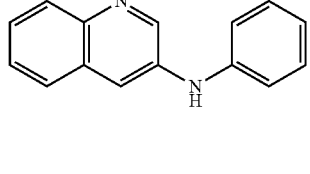 | 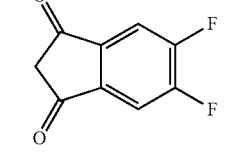 | C1 |
| 13 | 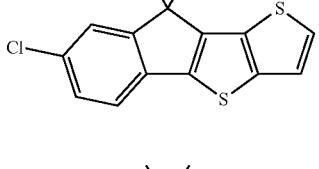 | 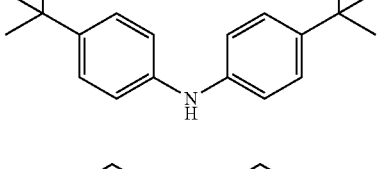 | 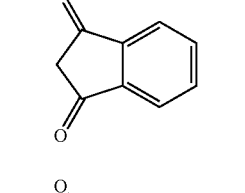 | C7 |
| 14 | 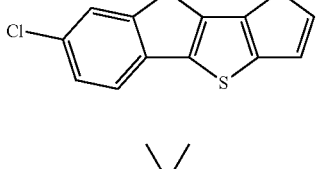 | 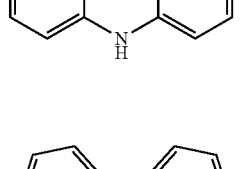 | 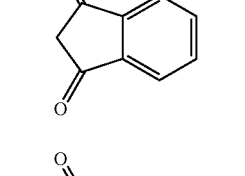 | C11 |
| 15 | 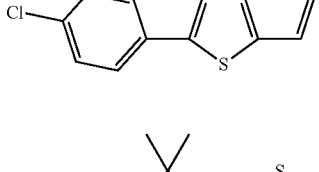 | 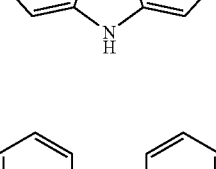 | 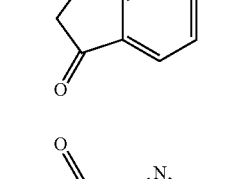 | C14 |
| 16 | 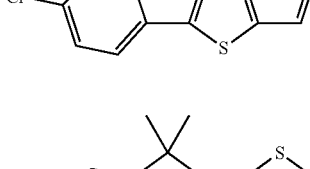 | 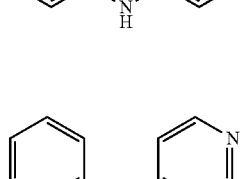 | 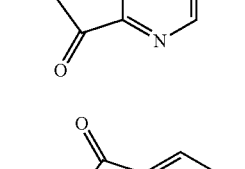 | C24 |
| 17 | 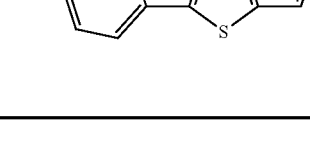 | 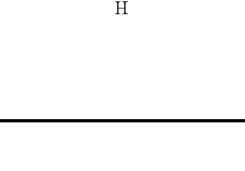 | 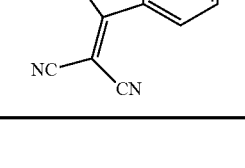 | D2 |

TABLE 5

| | F6 | F7 | F10 | Exemplified Compound No. |
|---|---|---|---|---|
| 18 | | | | D3 |
| 19 | | | | D6 |
| 20 | | | | D7 |

(B) Compound in which at Least One of $Y_1$ to $Y_3$ Represents Nitrogen Atom

A π-conjugated spacer skeleton can be synthesized in accordance with, for example, a synthesis scheme represented by the following formula [11].

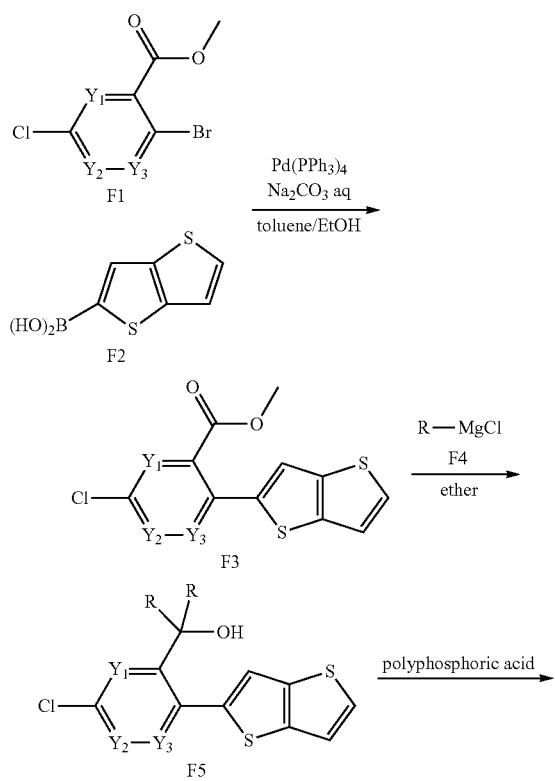

[11]

-continued

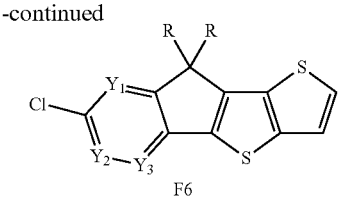

Specifically, the skeleton is synthesized by sequentially performing the following reactions (1) to (3).

(1) F3 can be synthesized by a cross-coupling reaction between a thienothiophene boron compound (F2) and F1 with a Pd catalyst. When the F1 has a pyridine ring, a pyrimidine ring, a pyrazine ring, a pyridazine ring, or a triazine ring, compounds corresponding to the respective rings can be synthesized.

(2) F5 can be synthesized by a nucleophilic addition reaction on the carbonyl group of the F3 with a Grignard reagent (F4). With regard to the F4, when R represents an alkyl group, the F5 can be similarly synthesized with various Grignard reagents. In the case of fluorine substitution, the F5 can be synthesized by, for example, using thionyl chloride and pyridine as reagents to be caused to react with the carbonyl group.

(3) F6 can be synthesized by the intramolecular cyclization reaction of the F5 with a Lewis acid or an acid.

When synthesis is performed by using the basic skeleton (F6) in accordance with a synthesis scheme represented by the following formula [12], the organic compound according to the embodiment of the present disclosure can be synthesized, and the same performance as that in the case where all of the $Y_1$ to the $Y_3$ represent methine groups can be obtained.

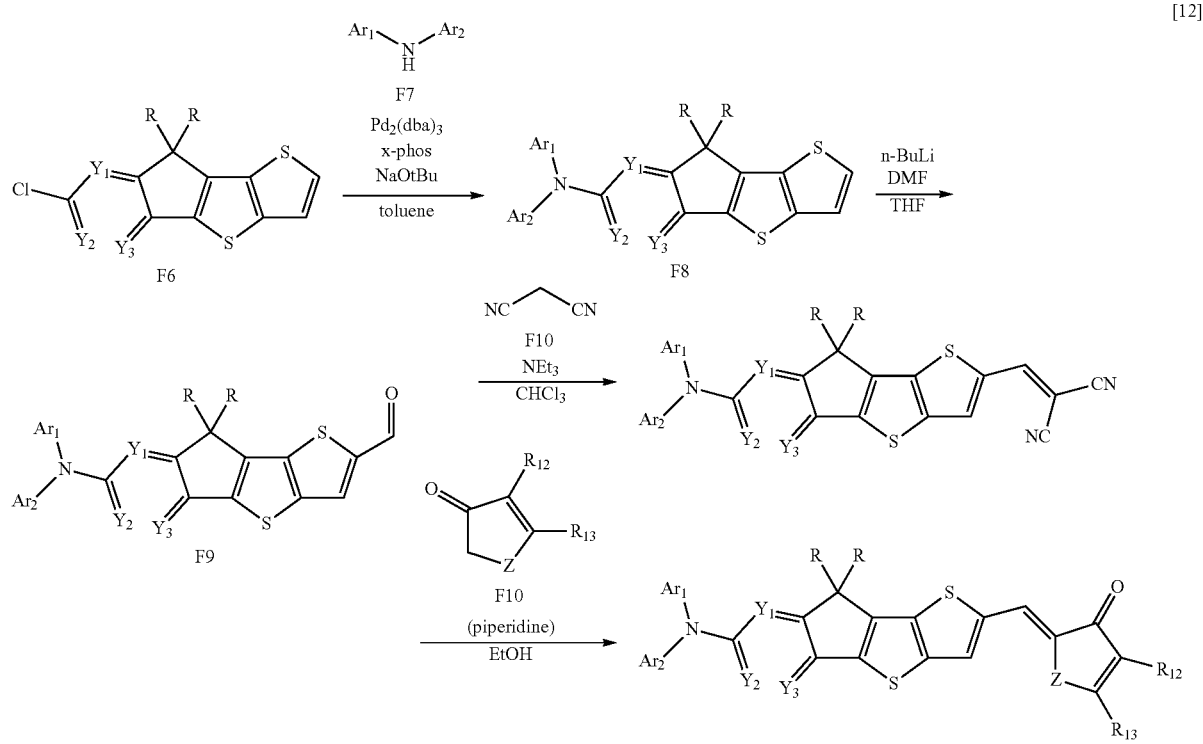

Specifically, the compound is synthesized by sequentially performing the following reactions (1) to (3).
(1) F8 can be synthesized by a cross-coupling reaction between the basic skeleton (F6) and an amine (F7) with a Pd catalyst.
(2) F9 can be synthesized by the formylation reaction of the F8 with n-butyllithium.
(3) The organic compound according to the embodiment of the present disclosure can be synthesized by Knoevenagel condensation between the F9 and F10. The organic compound according to the embodiment of the present disclosure can be similarly synthesized by changing the F10 to such a compound as represented by the general formula [10].

In addition, various compounds can be synthesized by changing the F6, the F7, and the F10. Specific examples thereof are shown in Table 6.

TABLE 6

| | F6 | F7 | F10 | Exemplified Compound No. |
|---|---|---|---|---|
| 30 | | | | AA1 |
| 32 | | | | AA5 |
| 33 | | | | AC1 |

TABLE 6-continued

| | F6 | F7 | F10 | Exemplified Compound No. |
|---|---|---|---|---|
| 34 | | | NC–CH2–CN | AC3 |
| 35 | | | | BA1 |
| 36 | | | | CC1 |
| 37 | | | | DA2 |

(C) Compound in which $R_1$ and $R_2$ Form Ring to have Spiro Structure

A π-conjugated spacer skeleton can be synthesized in accordance with, for example, a synthesis scheme represented by the following formula [13].

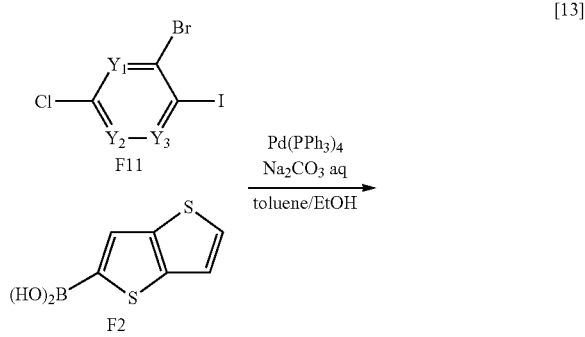

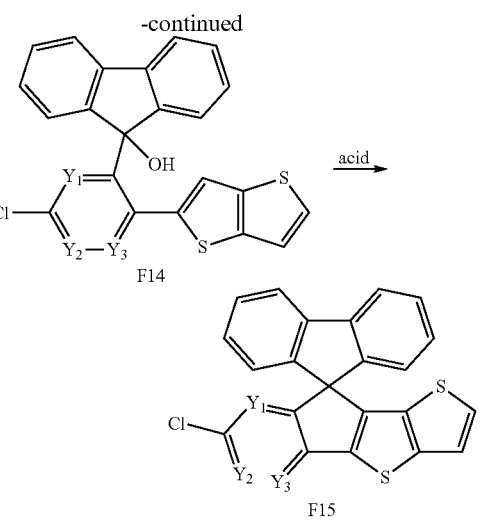

Specifically, the skeleton is synthesized by sequentially performing the following reactions (1) to (3).
(1) F12 can be synthesized by a cross-coupling reaction between the thienothiophene boron compound (F2) and F11 with a Pd catalyst. When the F11 has a benzene ring, a pyridine ring, a pyrimidine ring, a pyrazine ring, a pyridazine ring, or a triazine ring, compounds corresponding to the respective rings can be synthesized.
(2) F14 can be synthesized by the lithiation of the F12 with an alkyllithium reagent, followed by a nucleophilic addition reaction on a carbonyl compound (F13). The F13 is not limited to 9-fluorenone represented by the formula [13], and may be a 9-fluorenone derivative that has a substituent or contains a nitrogen atom.

(3) F15 can be synthesized by the intramolecular cyclization reaction of the F14 with a Lewis acid or an acid.

When synthesis is performed in accordance with one of the synthesis schemes represented by the formulae [9] and [12] in the same manner as in the foregoing except that the G6 or the F6 is changed to the basic skeleton F15, the organic compound according to the embodiment of the present disclosure can be synthesized. In addition, various compounds can be synthesized by changing the F15, the G7, the G10, the F7, and the F10. Specific examples thereof are shown in Table 7.

The organic compound layer may have: a second organic layer (second organic compound layer) 2 arranged between the first organic layer 1 and the cathode 4; and a third organic layer (third organic compound layer) 3 arranged between the first organic layer 1 and the anode 5. A protective layer 7, a wavelength-selecting portion 8, and a microlens 9 are arranged on the cathode 4. A readout circuit 6 is connected to the anode 5. The photoelectric conversion element 10 may be formed on a substrate (not shown). When the photoelectric conversion element 10 performs photoelectric conversion, a voltage may be applied between the anode 5 and the

TABLE 7

| | F15 | F7 | F10 | Exemplified Compound No. |
|---|---|---|---|---|
| 56 | 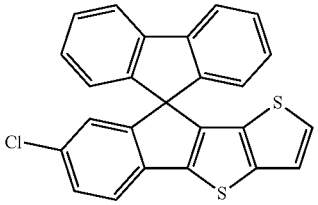 | 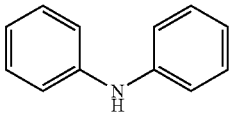 | 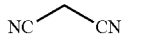 | A15 |
| 56 | 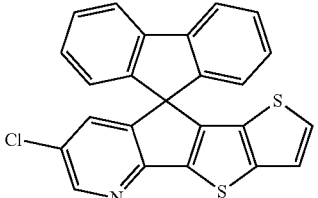 | 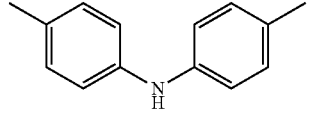 | 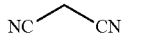 | AA9 |

Organic Electronic Element and Photoelectric Conversion Element According to Embodiments of the Present Disclosure (1) Organic Electronic Element and Photoelectric Conversion Element An organic electronic element according to an embodiment of the present disclosure includes a pair of electrodes and an organic compound layer arranged between the pair of electrodes. In addition, a photoelectric conversion element according to an embodiment of the present disclosure, which is a mode of the organic electronic element, includes an anode, a cathode, and an organic compound layer arranged between the anode and the cathode, and the organic compound layer has a first organic layer containing the organic compound according to the embodiment of the present disclosure. FIG. 1 is a schematic sectional view for illustrating an example of the photoelectric conversion element according to the embodiment of the present disclosure. In a photoelectric conversion element 10, an organic compound layer is arranged between an anode 5 and a cathode 4, and the organic compound layer has a first organic layer (first organic compound layer) 1 containing the organic compound according to the embodiment of the present disclosure. The first organic layer 1 is a layer configured to form a photoelectric conversion portion configured to convert light into charge. In view of the foregoing, the first organic layer 1 can also be referred to as "photoelectric conversion layer." When the photoelectric conversion element 10 has a plurality of layers, the plurality of layers are preferably laminated in a direction from the anode 5 to the cathode 4.

cathode 4. The voltage is preferably about 1 V or more and about 15 V or less, though the preferred voltage varies depending on the total thickness of the organic compound layer. The voltage is more preferably about 2 V or more and about 10 V or less.

(2) Substrate

The photoelectric conversion element according to the embodiment of the present disclosure may include a substrate. Examples of the substrate include a glass substrate, a flexible substrate, and a semiconductor substrate.

In addition, the photoelectric conversion element according to the embodiment of the present disclosure may include a semiconductor substrate. A constituent element for the semiconductor substrate is not limited as long as a charge-storing portion and a floating diffusion (FD) can be formed by the injection of impurities. Examples thereof include Si, GaAs, and GaP. Of those, Si is particularly preferred. The semiconductor substrate may be an N-type epitaxial layer. In that case, a P-type well, an N-type well, a P-type semiconductor region, and an N-type semiconductor region are arranged on the semiconductor substrate.

The charge-storing portion is an N-type semiconductor region or P-type semiconductor region formed on the semiconductor substrate by ion implantation, and is a region configured to store charge generated in the photoelectric conversion portion. When an electron is stored, the N-type semiconductor region may be formed on the surface of the semiconductor substrate, or a storage diode of a PN structure may be formed from the surface of the substrate. In each case, an electron can be stored in the N-type semiconductor region. Meanwhile, when a hole is stored, the P-type semiconductor region may be formed on the surface of the semiconductor substrate, or a storage diode of an NP structure may be formed from the surface of the substrate. In each case, an electron can be stored in the P-type semiconductor region.

The stored charge is transferred from the charge-storing portion to the FD. The charge transfer may be controlled by a gate electrode. The charge generated in the first organic layer 1 is stored in the charge-storing portion, and the charge stored in the charge-storing portion is transferred to the FD. After that, the charge is converted into a current by an amplification transistor (FIG. 2) to be described later. In addition, when the charge-storing portion forms a PN junction, the photoelectric conversion may be performed by light leaking from the photoelectric conversion portion. The photoelectric conversion element may include a charge-outputting portion without including the charge-storing portion. When the element includes the outputting portion, the charge generated in the first organic layer 1 is transferred from an electrode to the amplification transistor or the like without through the FD.

(3) Anode (Electron-Collecting Electrode) 5 and Cathode (Hole-Collecting Electrode) 4

The anode 5 is an electrode configured to collect an electron out of the charge generated in the first organic layer 1. The anode may be a pixel electrode in the construction of an imaging device. The anode 5 may be arranged on a side closer to a pixel circuit with respect to the cathode 4. The anode 5 can be called an electron-collecting electrode because of its function. A constituent material for the anode 5 is, for example, indium tin oxide (ITO), indium zinc oxide, $SnO_2$, antimony-doped tin oxide (ATO), ZnO, Al-doped zinc oxide (AZO), gallium-doped zinc oxide (GZO), $TiO_2$, or fluorine-doped tin oxide (FTO).

The cathode 4 is an electrode configured to collect a hole out of the charge generated in the first organic layer 1. The cathode may be a pixel electrode in the construction of the imaging device. A constituent material for the cathode 4 is, for example, a metal, a metal oxide, a metal nitride, a metal boride, an organic conductive compound, or a mixture obtained by combining two or more kinds thereof. Specific examples thereof include: conductive metal oxides, such as antimony-doped or fluorine-doped tin oxide (ATO or FTO), tin oxide, zinc oxide, indium oxide, indium tin oxide (ITO), and indium zinc oxide; metal materials, such as gold, silver, magnesium, chromium, nickel, titanium, tungsten, and aluminum; conductive compounds, such as oxides or nitrides of these metal materials (e.g., titanium nitride (TiN)); mixtures or laminates of these metals and the conductive metal oxides; inorganic conductive substances, such as copper iodide and copper sulfide; organic conductive materials, such as polyaniline, polythiophene, and polypyrrole; and laminates of these substances or materials and ITO or titanium nitride. The constituent material for the cathode 4 is particularly preferably a material selected from the group consisting of an alloy of magnesium and silver, titanium nitride, molybdenum nitride, tantalum nitride, and tungsten nitride.

The pixel electrode may be any one of the anode 5 and the cathode 4. The transparency of an electrode on a light extraction side is preferably high. The transparency is specifically 80% or more. In addition, an electrode on a light incident side can also be referred to as "upper electrode." In that case, the other electrode is referred to as "lower electrode."

A method of forming each of the above-mentioned two kinds of electrodes (the anode and the cathode) can be appropriately selected in consideration of its suitability with an electrode material to be used. Specifically, the electrodes can be formed by, for example, a printing system, a wet system, such as a coating system, a physical system, such as a vacuum deposition method, a sputtering method, or an ion plating method, or a chemical system, such as CVD or a plasma CVD method. In the case where the electrodes are formed by using ITO, the electrodes can be formed by a method such as an electron beam method, the sputtering method, a resistance heating deposition method, a chemical reaction method (e.g., a sol-gel method), or the application of a dispersed product of indium tin oxide. In addition, in such case, the surfaces of the formed electrodes (ITO electrodes) may be subjected to, for example, a UV-ozone treatment or a plasma treatment. In the case where the electrodes are formed by using TiN, various film-forming methods typified by a reactive sputtering method can be used. In addition, in such case, the formed electrodes (TiN electrodes) may be subjected to, for example, an annealing treatment, the UV-ozone treatment, or the plasma treatment.

(4) First Organic Layer (Photoelectric Conversion Layer) 1

As described above, the first organic layer 1 can also be referred to as "photoelectric conversion layer." A constituent material for the first organic layer 1 of the photoelectric conversion element according to the embodiment of the present disclosure is described. The first organic layer 1 contains the organic compound according to the embodiment of the present disclosure. It is preferred that the first organic layer 1 have a high light absorptivity and perform the charge separation of received light efficiently, that is, have high photoelectric conversion efficiency. In addition, the layer is preferably capable of immediately transporting generated charge, that is, an electron and a hole to the electrodes. In addition, in order that a reduction in quality of the layer, such as crystallization, may be suppressed, a material having a high glass transition temperature is preferred. The layer may be a mixed layer of the organic compound and the material having a high glass transition temperature from the viewpoint of an improvement in quality thereof. The first organic layer 1 may contain a plurality of kinds of organic compounds. When the first organic layer 1 has a plurality of kinds of organic compounds, the plurality of kinds of organic compounds may be mixed in one layer, or the plurality of kinds of organic compounds may be incorporated into a plurality of layers.

The first organic layer 1 is preferably a layer containing an organic p-type compound, such as a p-type organic semiconductor, or an organic n-type compound, such as an n-type organic semiconductor, and more preferably includes a bulk hetero layer (mixed layer), which is obtained by mixing the organic p-type compound and the organic n-type compound, in at least part thereof. When the first organic layer 1 has the bulk hetero layer, its photoelectric conversion efficiency (sensitivity) can be improved. When the layer has the bulk hetero layer at an optimum mixing ratio, the electron mobility and hole mobility of the first organic layer 1 can be increased, and hence the optical response speed of the photoelectric conversion element can be increased.

The first organic layer 1 preferably contains a fullerene, a fullerene analog, or a fullerene derivative as an n-type organic semiconductor. A plurality of fullerene molecules, fullerene analog molecules, or fullerene derivative molecules form an electron path. Accordingly, the electron transportability of the layer is improved, and hence the responsiveness of the photoelectric conversion element is improved. When the total amount of the photoelectric conversion layer is defined as 100%, the content of the fullerene, the fullerene analog, or the fullerene derivative is preferably 20 mass % or more and 80 mass % or less. The fullerene analog is a generic term for closed-shell cavity-shaped clusters each including only many carbon atoms, and examples thereof include fullerene C60, and fullerenes C70, C74, C76, and C78 serving as higher order fullerenes. Those materials may be used alone or in combination thereof. A material to be used as a material responsible for charge separation and electron carriage is not limited to the fullerene analog, and a plurality of other materials may be simultaneously used. A material except the fullerene is, for example, a naphthalene compound, such as NTCDI, a perylene compound, such as PTCDI, a phthalocyanine compound, such as SubPc, or a thiophene compound, such as DCV3T, the compounds being known as n-type organic semiconductors.

Examples of the fullerene analog include fullerene C60, fullerene C70, fullerene C76, fullerene C78, fullerene C80, fullerene C82, fullerene C84, fullerene C90, fullerene C96, fullerene C240, fullerene C540, mixed fullerene, and fullerene nanotubes. In addition, examples of the fullerene derivative include the following compounds.

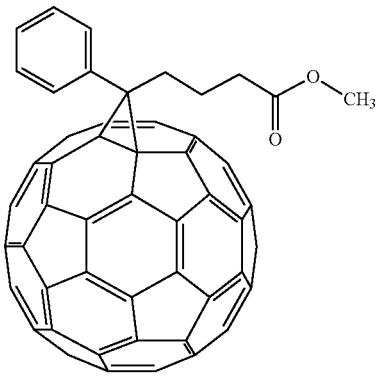

[60]PCBM

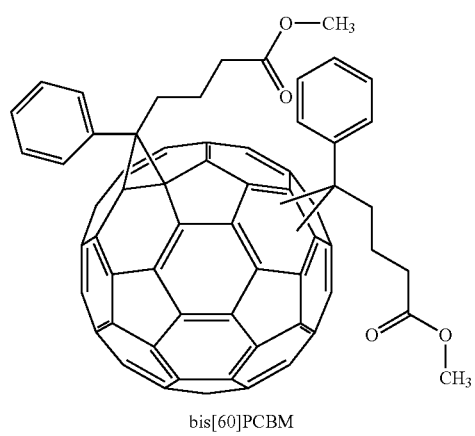

bis[60]PCBM

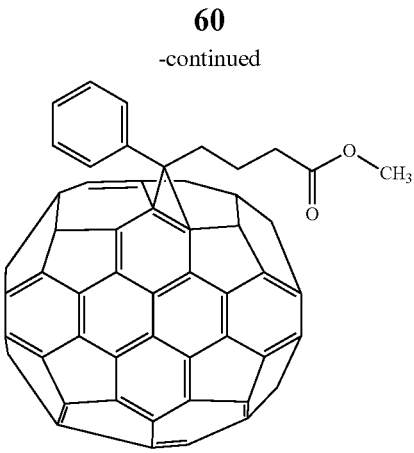

[70]PCBM

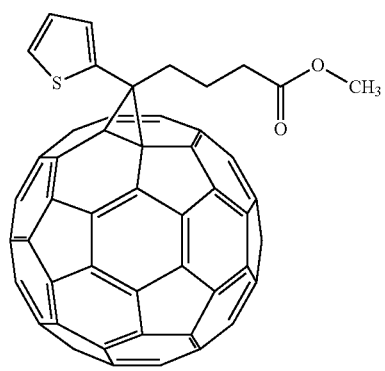

[60]ThCBM

The first organic layer 1 can contain an organic compound, such as a p-type organic semiconductor, except the organic compound according to the embodiment of the present disclosure. Examples of the p-type organic semiconductor in the photoelectric conversion element may include the following organic compounds. The compounds shown below may have substituents, such as an alkyl group, to the extent that their functions are not impaired.

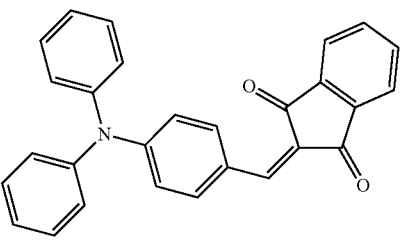

CG1

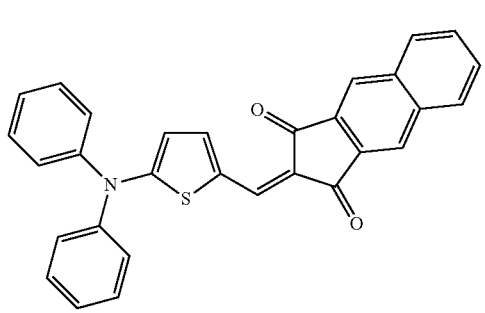

CG2

CG3
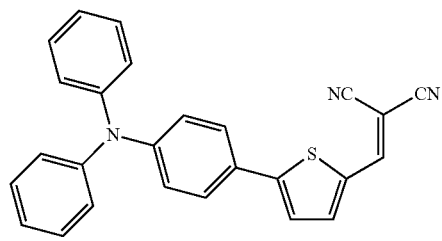
CG4
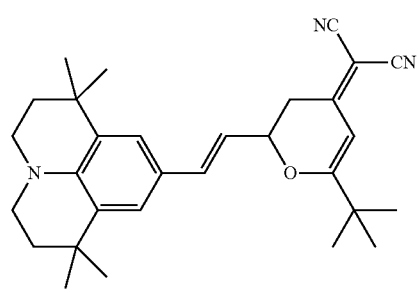
CG5
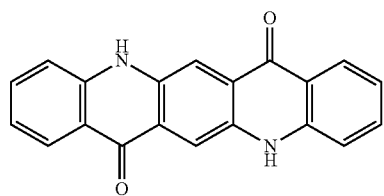
CG6
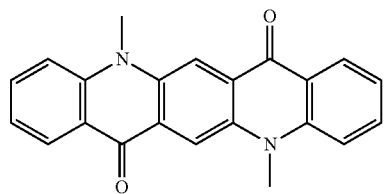
CG7
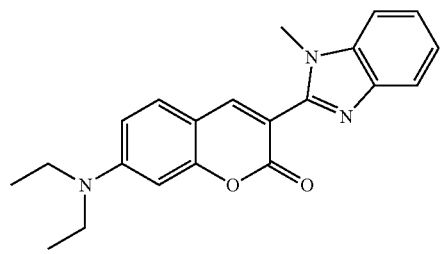
CG8
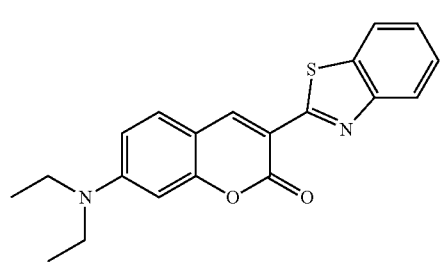
CG9
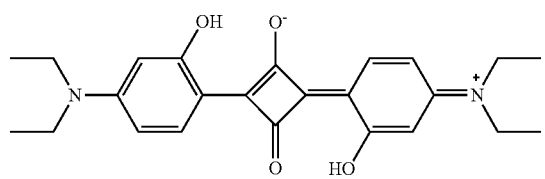
CG10
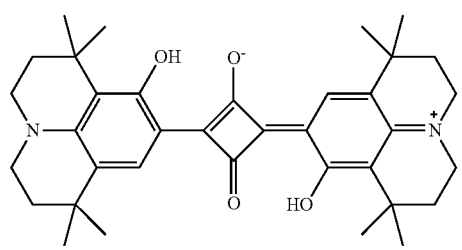
CG11
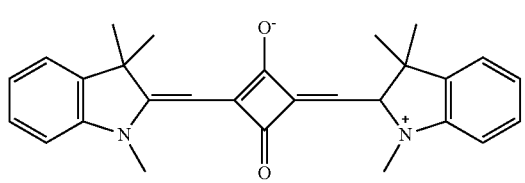
CG12
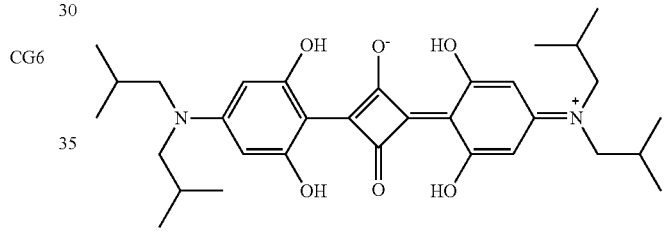
CG13
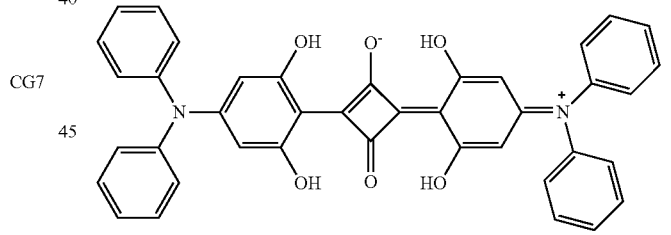
CG14
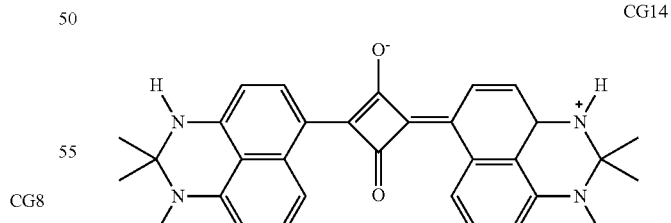
CG15
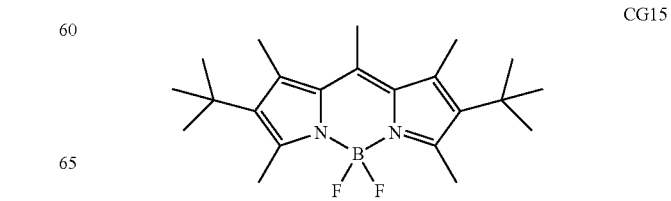

-continued
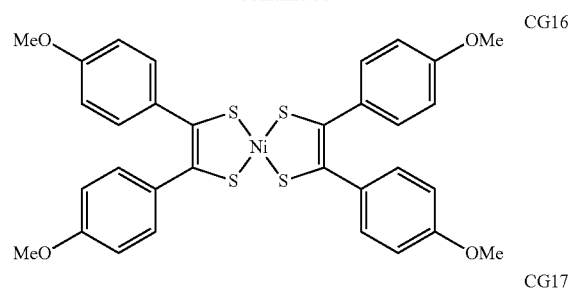
CG16
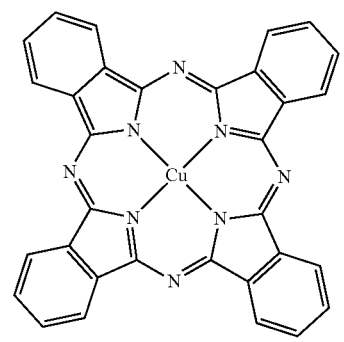
CG17
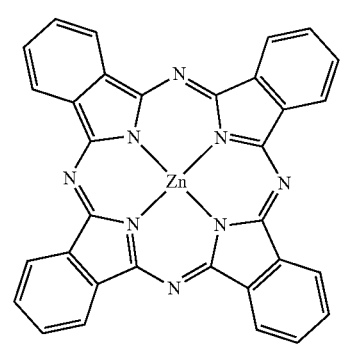
CG18
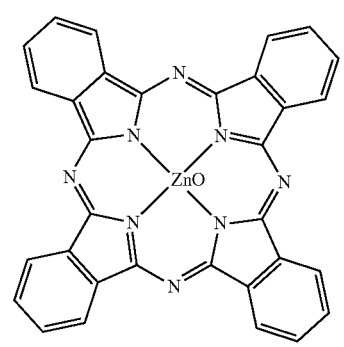
CG19
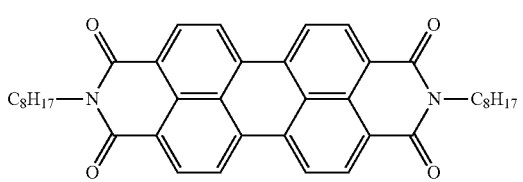
CG20
CG21
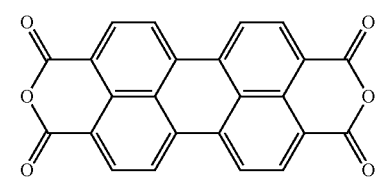
CG22
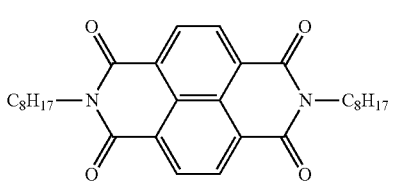
CG23
CG24
CG25
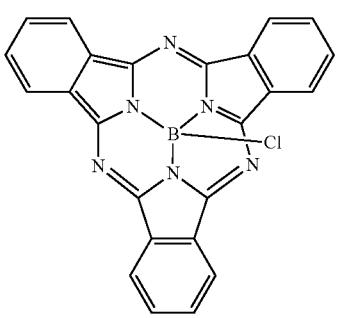
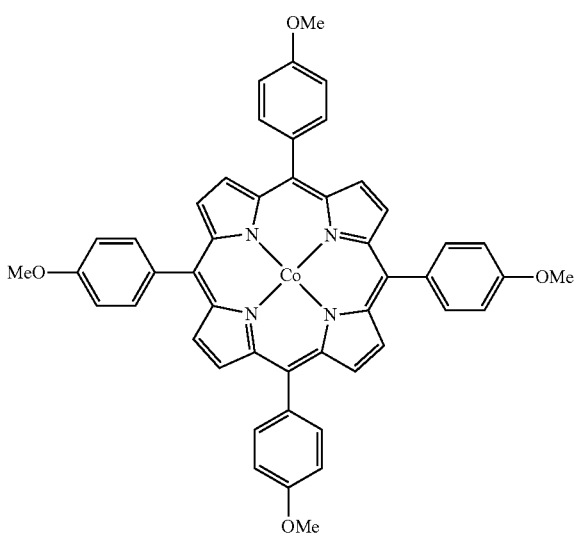
CG26

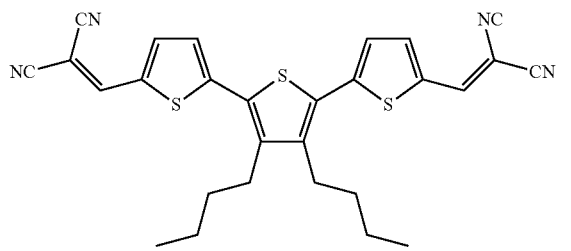

CG27

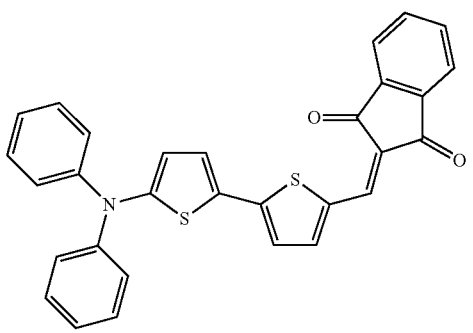

CG28

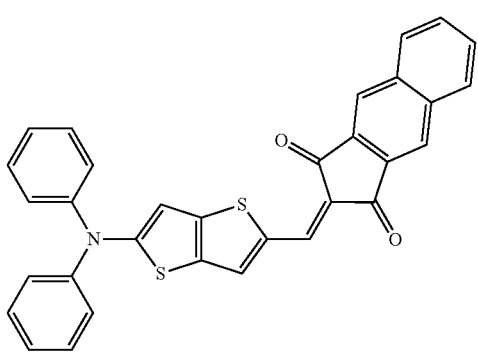

CG29

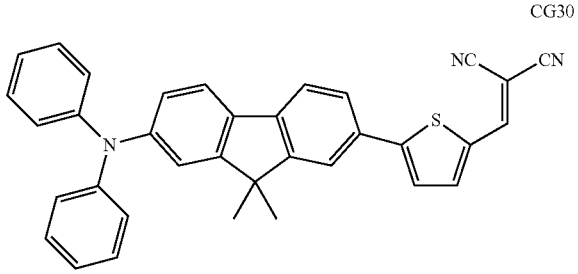

CG30

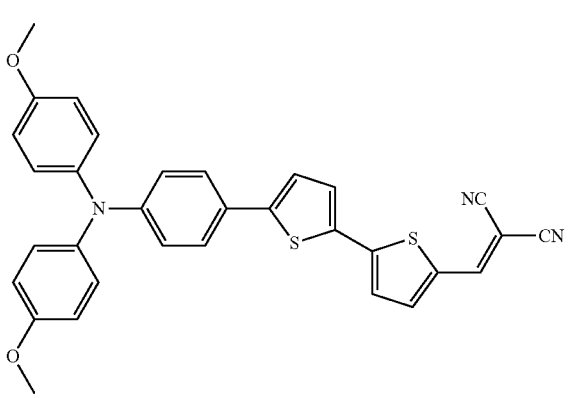

CG31

(5) Second Organic Layer (Electron-Blocking Layer) 2

The second organic layer 2 is a layer configured to suppress the flow of an electron from the cathode 4 into the first organic layer 1, and preferably has a small electron affinity (LUMO close to a vacuum level). A small electron affinity can be rephrased as a low LUMO. The second organic layer 2 can be called an electron-blocking layer because of its function. The second organic layer 2 may be a plurality of layers, or a bulk hetero layer (mixed layer) may be used as the layer. The photoelectric conversion element may include any other functional layer between the cathode 4 and the second organic layer 2.

(6) Third Organic Layer (Hole-Blocking Layer) 3

The third organic layer 3 is a layer configured to suppress the flow of a hole from the anode 5 into the first organic layer 1, and preferably has a large ionization potential (HOMO distant from the vacuum level). A large ionization potential can be rephrased as a high HOMO. The third organic layer 3 can be called a hole-blocking layer because of its function. The third organic layer 3 may be a plurality of layers, or a bulk hetero layer (mixed layer) may be used as the layer. The photoelectric conversion element may include any other functional layer between the anode 5 and the third organic layer 3.

(7) Protective Layer 7

The protective layer 7 is a layer to be formed above the electrodes, and is preferably an insulating layer. The protective layer 7 may be formed of a single material, or may include a plurality of materials. When the layer includes a plurality of materials, the layer may be obtained by laminating a plurality of layers, or may be a layer obtained by mixing the plurality of materials. A constituent material for the protective layer 7 is, for example, an organic material, such as a resin, or an inorganic material, such as silicon nitride, silicon oxide, or aluminum oxide. The layer can be formed by, for example, sputtering or an atomic layer deposition method (ALD method). Silicon nitride is also described as $SiN_X$ and silicon oxide is also as described as $SiO_X$. X is a numerical value representing an element ratio.

A planarization layer may be arranged on the protective layer 7. The layer is arranged for preventing the wavelength-selecting portion 8 from being affected by the surface state of the protective layer 7. The planarization layer can be formed by, for example, a known production method, application method, or vacuum deposition method. The layer may be produced by performing, for example, CMP as required. A constituent material for the planarization layer is, for example, an organic material, such as a resin, or an inorganic material, such as $SiN_X$, $SiO_X$, or $Al_2O_3$, and may include an organic compound or a mixture of such material and compound. Examples of a formation method for the layer may include the same methods as those for the protective layer 7.

(8) Wavelength-Selecting Portion 8

The wavelength-selecting portion 8 is arranged on the planarization layer. When the photoelectric conversion element does not include the planarization layer, the portion is arranged on the protective layer 7. The wavelength-selecting portion 8 can be arranged on the light incident side of the photoelectric conversion element. Examples of the wavelength-selecting portion 8 include a color filter, a scintillator, and a prism. The color filter is a filter configured to transmit light having a predetermined wavelength in a quantity larger than that of light having any other wavelength. For example, the element can correspond to the entirety of the visible light region by using three kinds of color filters, that is, R, G, and B color filters. When the three kinds of color filters, that is, the R, G, and B color filters are used, a Bayer array, a delta array, or the like may be used as the arrangement of the color filters. In addition, the wavelength-selecting portion may be a prism configured to separate only light having a predetermined wavelength. The position at which the wavelength-selecting portion 8 is arranged is not limited to the position illustrated in FIG. 1. The wavelength-selecting portion 8 only needs to be arranged at any position on an optical path from an object or a light source to the photoelectric conversion layer 1.

(9) Lens 9

The lens 9, such as the microlens, is an optical member for converging light from the outside in the first organic layer 1. Although a hemispherical lens is illustrated in FIG. 1, the shape of the lens is not limited thereto. The lens 9 includes, for example, quartz, silicon, or an organic resin. The shape and material of the lens are not limited as long as its light convergence is not inhibited.

(10) Other Construction

The photoelectric conversion element may include any other photoelectric conversion element on an electrode. When the other photoelectric conversion element is a photoelectric conversion element configured to perform the photoelectric conversion of light having a wavelength different from that of light to be subjected to photoelectric conversion by the foregoing element, the light having the different wavelength can be detected at an identical or substantially identical in-plane position on the substrate.

In addition, the photoelectric conversion element may be constructed as follows: the element further includes another kind of organic compound layer configured to perform the photoelectric conversion of light having a wavelength different from that of light to be subjected to photoelectric conversion by the first organic layer 1, and the first organic layer 1 and the other kind of organic compound layer are laminated. With the construction, as in the construction in which the photoelectric conversion elements are laminated, the light having the different wavelength can be detected at an identical position or a substantially identical position on the substrate.

Imaging Device According to Embodiment of the Present Disclosure and Imaging Apparatus Including the Device (1) Imaging Device The photoelectric conversion element according to the embodiment of the present disclosure can be used in an imaging device. The imaging device includes: a plurality of photoelectric conversion elements serving as light-receiving pixels; a readout circuit connected to each of the photoelectric conversion elements; and a signal processing circuit (signal processing portion) connected to the readout circuit. Information based on charge that has been read out is transmitted to the signal processing portion connected to the imaging device. Examples of the signal processing portion include a CMOS sensor and a CCD sensor. When pieces of information acquired in the respective light-receiving pixels are gathered in the signal processing portion, an image can be obtained.

The imaging device may include a plurality of photoelectric conversion elements, and the plurality of photoelectric conversion elements may have color filters different from each other in kind. The plurality of kinds of color filters are color filters configured to transmit light beams having wavelengths different from each other. Specifically, the elements may have the respective R, G, and B color filters. The plurality of photoelectric conversion elements may include a photoelectric conversion layer as a common layer. The term "common layer" means that the photoelectric conversion layer of a photoelectric conversion element and the photoelectric conversion layer of a photoelectric conversion element adjacent thereto are one and the same.

Figure 2:
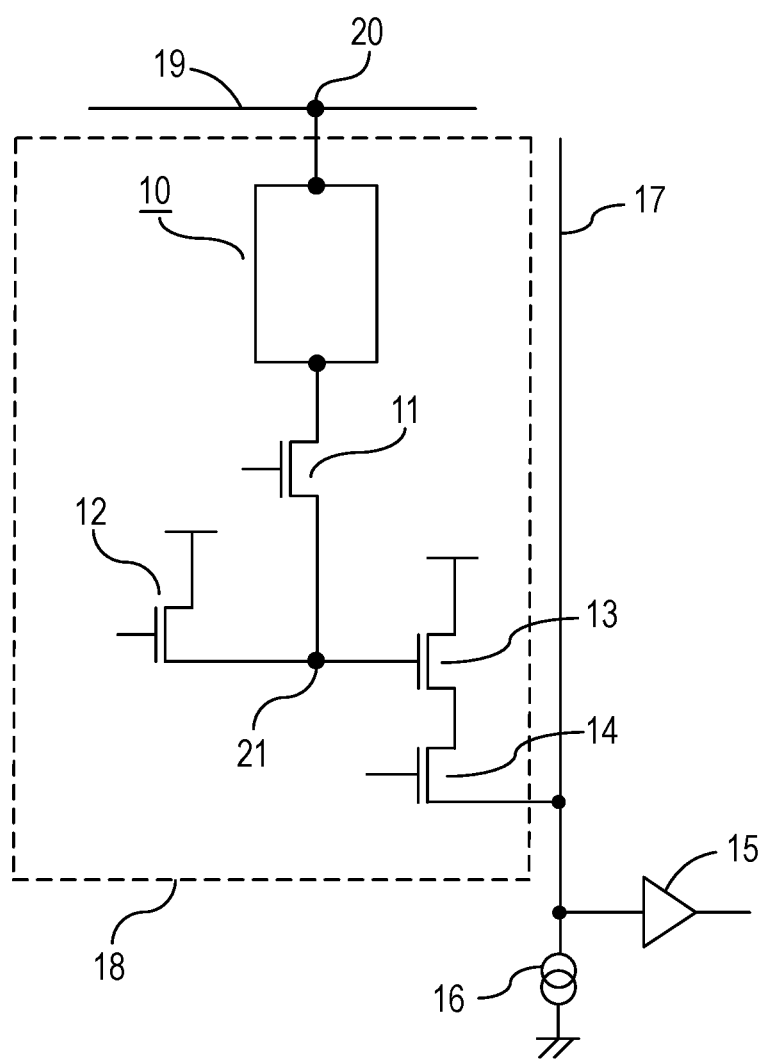
FIG. 2 is a circuit diagram of a pixel including the photoelectric conversion element according to the embodiment of the present disclosure.

FIG. 2 is a circuit diagram of a pixel including the photoelectric conversion element according to the embodiment of the present disclosure. The photoelectric conversion element 10 is connected to a common wiring 19 by a node A 20. The common wiring 19 may be connected to the ground. A pixel 18 may include the photoelectric conversion element 10 and a readout circuit for reading out a signal produced in the photoelectric conversion portion. The readout circuit may include, for example, a transfer transistor 11, an amplification transistor 13, a selection transistor 14, and a reset transistor 12. The transfer transistor 11 is electrically connected to the photoelectric conversion element 10. The amplification transistor 13 has a gate electrode electrically connected to the photoelectric conversion element 10. The selection transistor 14 is configured to select a pixel from which information is read out. The reset transistor 12 is configured to supply a reset voltage to the photoelectric conversion element 10.

Transfer by the transfer transistor 11 may be controlled by a gate voltage. The supply of the reset voltage by the reset transistor 12 may be controlled by a voltage to be applied to its gate. The selection transistor 14 is brought into a selection or non-selection state by its gate voltage. The transfer transistor 11, the reset transistor 12, and the amplification transistor 13 are connected to one another by a node B 21. The readout circuit may be free of the transfer transistor 11 depending on its construction. The reset transistor 12 is a transistor configured to supply a voltage configured to reset the potential of the node B 21. The application of a signal to the gate of the reset transistor 12 can control the supply of the voltage. The circuit may be free of the reset transistor 12 depending on the construction. The amplification transistor 13 is a transistor configured to flow a current in accordance with the potential of the node B 21. The amplification transistor 13 is connected to the selection transistor 14 configured to select the pixel 18 from which a signal is output. The selection transistor 14 is connected to a current source 16 and a column output portion 15, and the column output portion 15 is connected to the signal processing portion. The selection transistor 14 is connected to a vertical output signal line 17. The vertical output signal line 17 is connected to the current source 16 and the column output portion 15.

Figure 3:
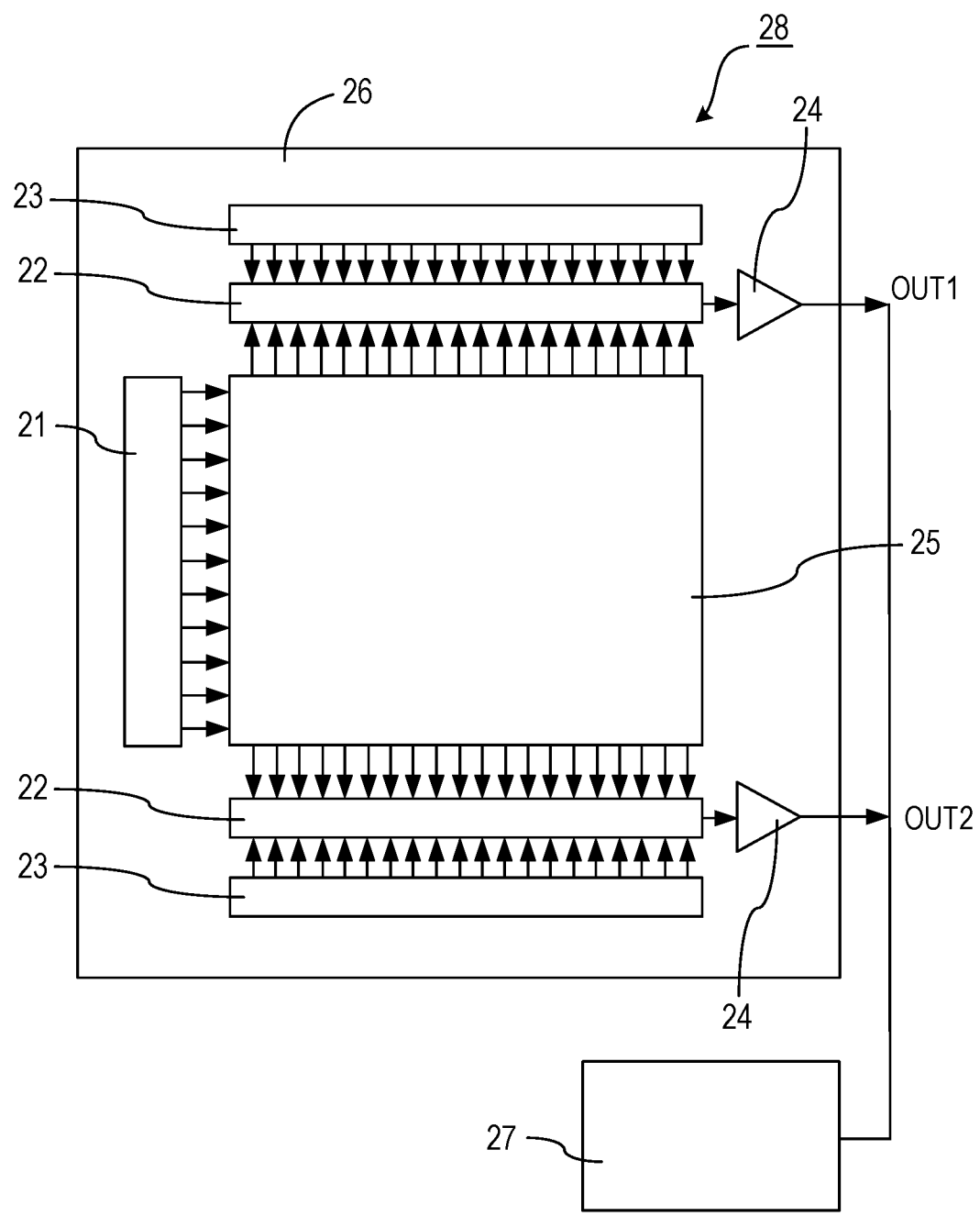
FIG. 3 is a schematic view for illustrating an imaging device according to an embodiment of the present disclosure.

FIG. 3 is a schematic view for illustrating the imaging device according to an embodiment of the present disclosure. An imaging device 28 includes an image pickup region 25 in which a plurality of pixels are arranged in a two-dimensional manner, and a peripheral region 26. The region except the image pickup region 25 is the peripheral region 26. The peripheral region 26 has a vertical scanning circuit 21, readout circuits 22, horizontal scanning circuits 23, and output amplifiers 24, and the output amplifiers 24 are connected to a signal processing portion 27. The signal processing portion 27 is a signal processing portion configured to perform signal processing based on information read out in the readout circuits 22, and examples thereof include a CCD circuit and a CMOS circuit.

Each of the readout circuits 22 includes, for example, a column amplifier, a correlated double sampling (CDS) circuit, and an addition circuit, and performs the amplification, addition, and the like of a signal read out from a pixel in a row selected by the vertical scanning circuit 21 through a vertical signal line. The column amplifier, the CDS circuit, the addition circuit, and the like are arranged in, for example, each pixel column or each plurality of pixel columns. The CDS circuit is a circuit configured to perform CDS signal processing, and performs a kTC noise reduction. The horizontal scanning circuits 23 produce signals for reading out the signals of the readout circuits 22 in order. The output amplifiers 24 amplify and output the signals of columns selected by the horizontal scanning circuits 23.

The foregoing construction is merely a construction example of the imaging device, and the embodiment of the present disclosure is not limited thereto. The readout circuits 22, the horizontal scanning circuits 23, and the output amplifiers 24 are vertically arranged one by one across the image pickup region 25 in order that two output paths may be formed. However, three or more output paths may be arranged. Signals output from the respective output amplifiers 24 are synthesized as an image signal in the signal processing portion 27.

(2) Imaging Apparatus

The imaging device according to the embodiment of the present disclosure can be used in an imaging apparatus. The imaging apparatus includes an imaging optical system having a plurality of lenses, and an imaging device configured to receive light that has passed the imaging optical system. In addition, the imaging apparatus includes an imaging device and a casing configured to store the imaging device, and the casing may have a joining portion capable of being joined to an imaging optical system. The imaging apparatus is more specifically a digital camera or a digital still camera.

In addition, the imaging apparatus may include a communicating portion configured to allow an image that has been picked up to be viewed from the outside. The communicating portion may include a receiving portion configured to receive a signal from the outside or a transmitting portion configured to transmit information to the outside. The signal received by the receiving portion is a signal configured to control at least one of the image pickup range of the imaging apparatus, the start of the image pickup thereof, or the end of the image pickup. In addition, the transmitting portion may transmit, in addition to the image that has been picked up, information, such as a warning about the image, the remaining amount of a data capacity, and the remaining amount of a power source. When the apparatus includes the receiving portion or the transmitting portion, the apparatus can be used as a network camera.

EXAMPLES

The present disclosure is described in detail below by way of Examples. The present disclosure is not limited to these Examples.

Example 1

Synthesis of Exemplified Compound A1

Exemplified Compound A1 was synthesized by the following scheme.

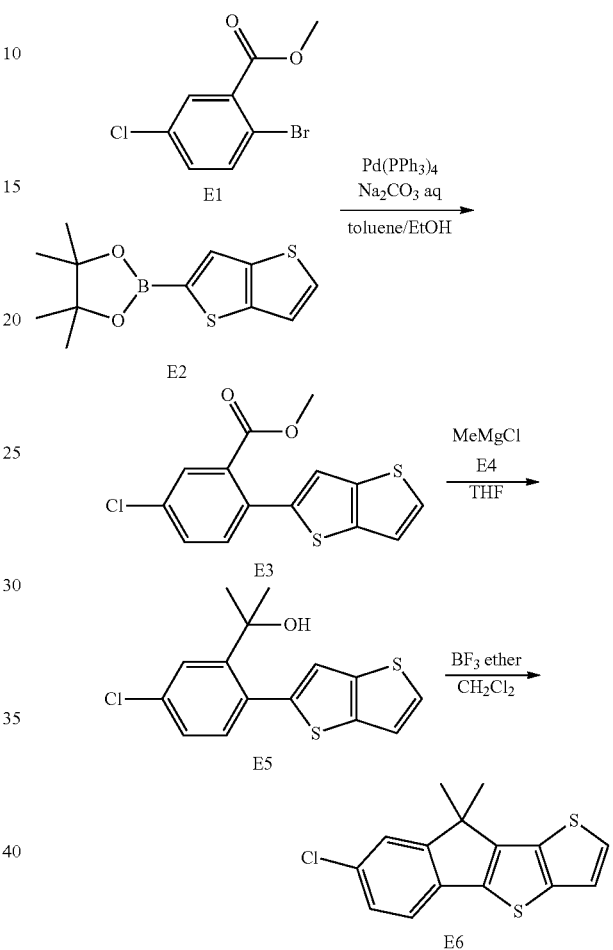

4.0 Grams (16.0 mmol) of E1 and 4.3 g (16.0 mmol) of E2 were loaded into 50 ml of toluene, 25 ml of ethanol, and 25 ml of a 20 mass % aqueous solution of sodium carbonate. Further, 0.6 g (0.5 mmol) of tetrakistriphenylphosphine palladium(0) was added to the mixture, and the whole was heated to a temperature of 90° C. and stirred for 5 hours. The resultant was cooled, and was then extracted with toluene and concentrated. The residue was purified by silica gel column chromatography (mobile phase; heptane:ethyl acetate=9:1) to provide 4.0 g of a yellow liquid E3 (yield: 81%).

4.0 Grams (13.0 mmol) of E3 was loaded into 130 ml of tetrahydrofuran. Further, 13 ml (38.9 mmol) of E4 (3.0 M tetrahydrofuran solution) was dropped into the mixture at 30° C., and the whole was heated to reflux and stirred for 5 hours. After the reaction, the resultant was cooled to 0° C., and ethanol, water, and dilute hydrochloric acid were added thereto in the stated order, followed by extraction with ethyl acetate. The extract was concentrated, and then the residue was purified by silica gel column chromatography (mobile phase; heptane:chloroform=1:1) to provide 2.0 g of a yellow liquid E5 (yield: 51%).

2.0 Grams (6.5 mmol) of E5 was loaded into 130 ml of dichloromethane. Further, 0.8 ml (6.5 mmol) of a boron trifluoride diethyl ether complex was dropped into the mixture at 0° C., and the whole was stirred as it was for 30 minutes. After the reaction, an aqueous solution of sodium hydrogen carbonate was added to the resultant, and the mixture was extracted with dichloromethane. The extract was concentrated, and then the residue was purified by silica gel column chromatography (mobile phase; heptane) to provide 1.1 g of a white solid E6 (yield: 56%).

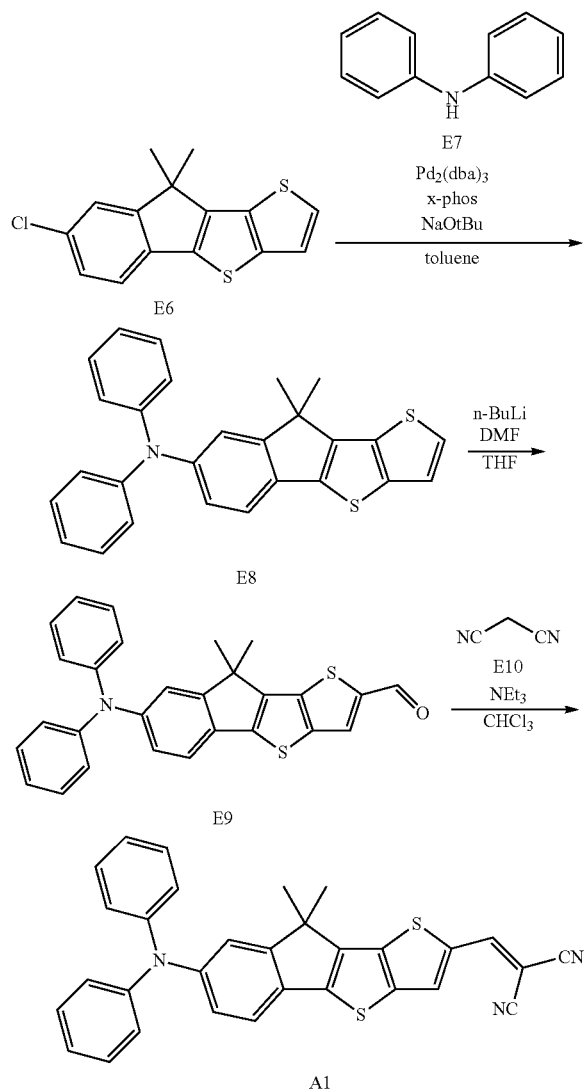

90 Milligrams (0.1 mmol) of tris(dibenzylideneacetone)dipalladium(0) and 150 mg (0.3 mmol) of x-phos were loaded into 10 ml of toluene, and the mixture was stirred at room temperature for 15 minutes. 600 Milligrams (2.1 mmol) of E6 and 450 mg (2.3 mmol) of E7 were added to the solution. Further, 400 mg (4.1 mmol) of sodium tert-butoxide was added to the mixture, and the whole was stirred at 120° C. for 2 hours. The resultant was cooled, and was then filtered with Celite and concentrated. The residue was purified by silica gel column chromatography (mobile phase; heptane:toluene=6:1) to provide 830 mg of a white solid E8 (yield: 94%).

680 Milligrams (1.6 mmol) of E8 was loaded into 20 ml of tetrahydrofuran, and the mixture was cooled to −78° C. Further, 1.5 ml (2.4 mmol) of n-butyllithium (1.6 M n-hexane solution) was dropped into the mixture at −78° C., and the whole was stirred for 2 hours while its temperature was slowly increased to 0° C. Further, the resultant was cooled to −78° C. again, and then 0.4 ml (4.8 mmol) of DMF was dropped thereinto at −78° C. The mixture was stirred for 3 hours while its temperature was slowly increased to room temperature. After the reaction, dilute hydrochloric acid was added to the resultant, and the mixture was extracted with ethyl acetate. The extract was concentrated, and then the residue was purified by silica gel column chromatography (mobile phase; heptane:chloroform=1:1) to provide 580 mg of a yellow solid E9 (yield: 81%).

380 Milligrams (0.8 mmol) of E9 was loaded into 10 ml of chloroform. Further, 170 mg (2.4 mmol) of E10 and 3 droplets of triethylamine were added to the mixture, and the whole was stirred as it was for 2 hours. After the reaction, the resultant was extracted with chloroform. The extract was concentrated, and then the residue was purified by silica gel column chromatography (mobile phase; heptane:chloroform=1:1) to provide 400 mg of a dark red solid A1 (yield: 96%). Mass spectrometry identified a peak at an m/z of 500 corresponding to the M+ of Exemplified Compound A1.

The absorption spectrum of Exemplified Compound A1 in a chloroform dilute solution was measured. As a result, the maximum absorption wavelength in a visible light region was 551 nm. Further, the molar extinction coefficient of the compound in the chloroform dilute solution ($5 \times 10^{-5}$ mol/l) was measured. As a result, the molar extinction coefficient was 54,700 $M^{-1}$ $cm^{-1}$ at a wavelength of 551 nm. In addition, the measurement was performed in the same manner as in the foregoing except that the measurement solvent was changed to a chlorobenzene dilute solution ($3 \times 10$-mol/l). As a result, the molar extinction coefficient of the compound was 51,700 $M^{-1}$ $cm^{-1}$ at a wavelength of 545 nm. A UV-visible spectrophotometer V-560 manufactured by JASCO Corporation was used as an apparatus.

Example 2

Synthesis of Exemplified Compound A2

Exemplified Compound A2 was synthesized in the same manner as in Example 1 except that E7 was changed to Compound E11 shown below. Mass spectrometry identified a peak at an m/z of 528 corresponding to the M+ of Exemplified Compound A2.

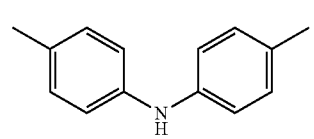

E11

Example 3

Synthesis of Exemplified Compound A7

Exemplified Compound A7 was synthesized in the same manner as in Example 1 except that E7 was changed to Compound E12 shown below. Mass spectrometry identified a peak at an m/z of 592 corresponding to the M⁺ of Exemplified Compound A7.

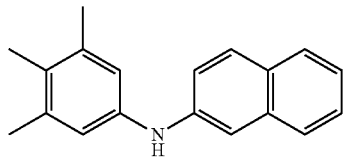

E12

Example 4

Synthesis of Exemplified Compound A10

Exemplified Compound A10 was synthesized in the same manner as in Example 1 except that E7 was changed to Compound E13 shown below. Mass spectrometry identified a peak at an m/z of 652 corresponding to the M⁺ of Exemplified Compound A10.

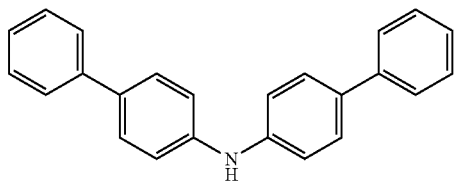

E13

Example 5

Synthesis of Exemplified Compound A23

Exemplified Compound A23 was synthesized in the same manner as in Example 1 except that E7 was changed to Compound E14 shown below. Mass spectrometry identified a peak at an m/z of 515 corresponding to the M⁺ of Exemplified Compound A23.

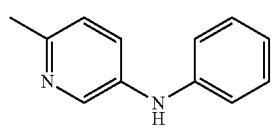

E14

Example 6

Synthesis of Exemplified Compound B1

Exemplified Compound B1 was synthesized in the same manner as in Example 1 except that: E10 was changed to Compound E15; and the following scheme was adopted.

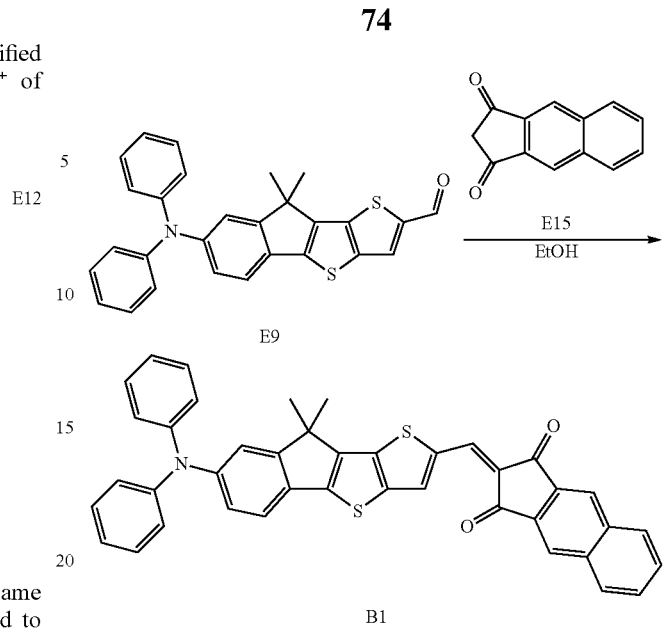

200 Milligrams (0.4 mmol) of E9 was loaded into 30 ml of ethanol. Further, 80 mg (1.3 mmol) of E15 was added to the mixture, and the whole was stirred under heating at 90° C. for 3 hours. After the reaction, the resultant was filtered, and the residue was purified by silica gel column chromatography (mobile phase; chloroform) to provide 170 mg of a black solid B1 (yield: 65%). Mass spectrometry identified a peak at an m/z of 630 corresponding to the M⁺ of Exemplified Compound B1.

Example 7

Synthesis of Exemplified Compound B4

Exemplified Compound B4 was synthesized in the same manner as in Example 1 except that: E10 was changed to Compound E16; and the following scheme was adopted.

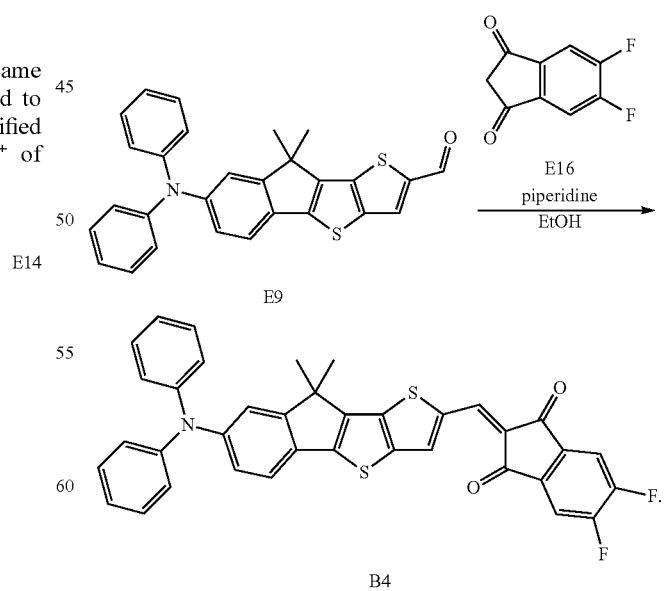

200 Milligrams (0.4 mmol) of E9 was loaded into 30 ml of ethanol. Further, 80 mg (0.4 mmol) of E16 and 0.1 ml of piperidine were added to the mixture, and the whole was stirred under heating at 90° C. for 2 hours. After the reaction, the resultant was filtered, and the residue was purified by silica gel column chromatography (mobile phase; chloroform) to provide 190 mg of a black solid B4 (yield: 75%). Mass spectrometry identified a peak at an m/z of 616 corresponding to the M⁺ of Exemplified Compound B4.

Example 8

Synthesis of Exemplified Compound C5

Exemplified Compound C5 was synthesized in the same manner as in Example 7 except that E16 was changed to Compound E17 shown below. Mass spectrometry identified a peak at an m/z of 580 corresponding to the M⁺ of Exemplified Compound C5.

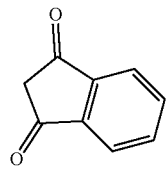

E17

Example 9

Synthesis of Exemplified Compound C12

Exemplified Compound C12 was synthesized in the same manner as in Example 7 except that: E16 was changed to E17; and E7 was changed to Compound E18 shown below. Mass spectrometry identified a peak at an m/z of 631 corresponding to the M⁺ of Exemplified Compound C12.

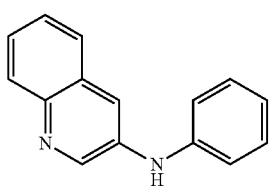

E18

Example 10

Synthesis of Exemplified Compound C17

Exemplified Compound C17 was synthesized in the same manner as in Example 7 except that E16 was changed to Compound E19 shown below. Mass spectrometry identified a peak at an m/z of 586 corresponding to the M⁺ of Exemplified Compound C17.

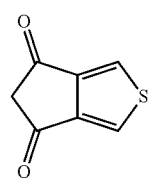

E19

Example 11

Synthesis of Exemplified Compound C21

Exemplified Compound C21 was synthesized in the same manner as in Example 7 except that: E7 was changed to Compound E20 shown below; and E16 was changed to Compound E21 shown below. Mass spectrometry identified a peak at an m/z of 631 corresponding to the M⁺ of Exemplified Compound C21.

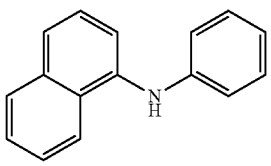

E20

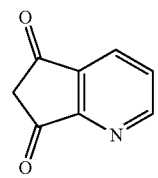

E21

Example 12

Synthesis of Exemplified Compound AA2

Exemplified Compound AA2 was synthesized in the same manner as in Example 2 except that E1 was changed to Compound E22 shown below. Mass spectrometry identified a peak at an m/z of 529 corresponding to the M⁺ of Exemplified Compound AA2.

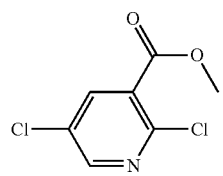

E22

Example 13

Synthesis of Exemplified Compound AB3

Exemplified Compound AB3 was synthesized in the same manner as in Example 1 except that: E7 was changed to Compound E23 shown below; and E1 was changed to Compound E24 shown below. Mass spectrometry identified a peak at an m/z of 571 corresponding to the M⁺ of Exemplified Compound AB3.

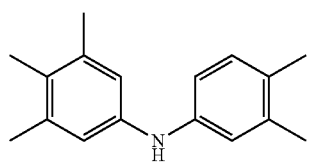

E23

E24

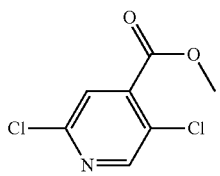

Example 14

Synthesis of Exemplified Compound AB5

Exemplified Compound AB5 was synthesized in the same manner as in Example 2 except that E1 was changed to Compound E25 shown below. Mass spectrometry identified a peak at an m/z of 529 corresponding to the M⁺ of Exemplified Compound AB5.

E25

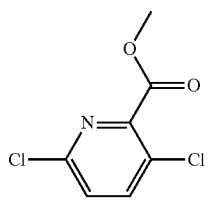

Example 15

Synthesis of Exemplified Compound CA2

Exemplified Compound CA2 was synthesized in the same manner as in Example 7 except that: E1 was changed to Compound E22 shown below; and E16 was changed to Compound E17 shown below. Mass spectrometry identified a peak at an m/z of 581 corresponding to the M⁺ of Exemplified Compound CA2.

E22

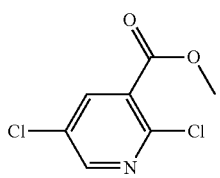

E17

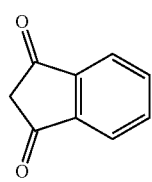

Comparative Example 1

Synthesis of Comparative Compound a-2

Comparative Compound a-2 was synthesized in the same manner as in Example 1 except that E9 was changed to E26.

E26

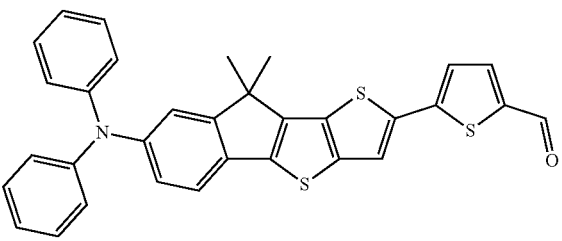

Mass spectrometry identified a peak at an m/z of 582 corresponding to the M⁺ of Comparative Compound a-2.

The absorption spectrum of Comparative Compound a-2 in a chloroform dilute solution was measured in the same manner as in Example 1. As a result, the maximum absorption wavelength in the visible light region was 579 nm. Further, the molar extinction coefficient of the compound in the chloroform dilute solution was measured. As a result, the molar extinction coefficient was 43,800 $M^{-1}$ $cm^{-1}$ at a wavelength of 579 nm. In addition, the measurement was performed in the same manner as in the foregoing except that the measurement solvent was changed to a chlorobenzene dilute solution. As a result, the molar extinction coefficient of the compound was 41,400 $M^{-1}$ $cm^{-1}$ at a wavelength of 573 nm.

Examples 16 to 42, and Comparative Examples 2 and 3

A photoelectric conversion element in which the hole-collecting electrode (cathode) 4, the electron-blocking layer (second organic layer) 2, the photoelectric conversion layer (first organic layer) 1, the hole-blocking layer (third organic layer) 3, and the electron-collecting electrode (anode) 5 were sequentially formed on a substrate was produced. First, an IZO film was formed on a Si substrate and subjected to desired patterning processing to form an IZO electrode (the hole-collecting electrode 4). At this time, the thickness of the IZO electrode was set to 100 nm. The substrate on which the IZO electrode had been formed as described above was used as an IZO substrate in the following process. Organic compound layers (the electron-blocking layer 2, the photoelectric conversion layer 1, and the hole-blocking layer 3) and an electrode layer (the electron-collecting electrode 5) shown in Table 8 were continuously formed on the IZO substrate. At this time, the electrode area of the opposing electrode (the electron-collecting electrode 5) was set to 3 $mm^2$.

TABLE 8

| | Material | Thickness (nm) |
|---|---|---|
| Electron-blocking layer | Z1 | 50 |
| Photoelectric conversion layer | Z2 (light-absorbing material) Z3 (photoelectric conversion-inducing material) (Z2:Z3 = 30:70 (mass ratio)) | 200 |

TABLE 8-continued

| | Material | Thickness (nm) |
|---|---|---|
| Hole-blocking layer | Fullerene C60 | 10 |
| Electron-collecting electrode | IZO | 30 |

Any one of Compounds Y1 to Y3 shown below was used as a material Z1 for the electron-blocking layer 2.

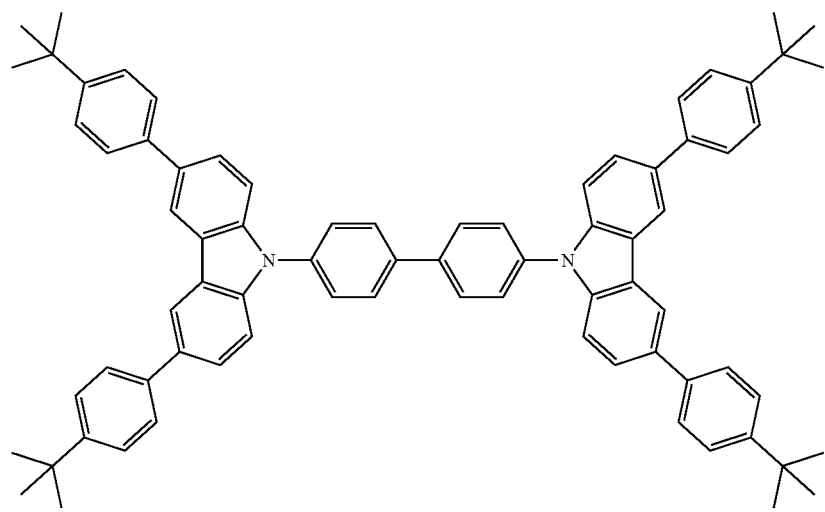

Y1

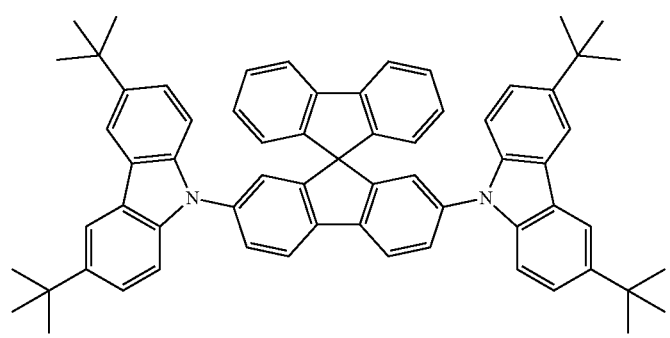

Y2

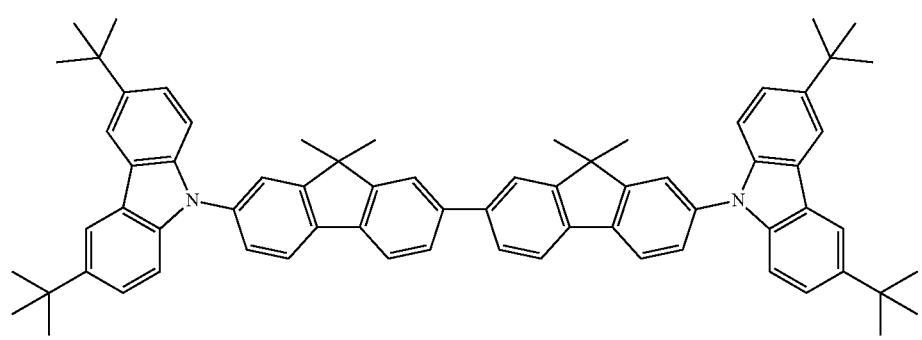

Y3

Fullerene C60 (C60), fullerene C70 (C70), or DCV3T was used as a photoelectric conversion-inducing material Z3 for the photoelectric conversion layer 1.

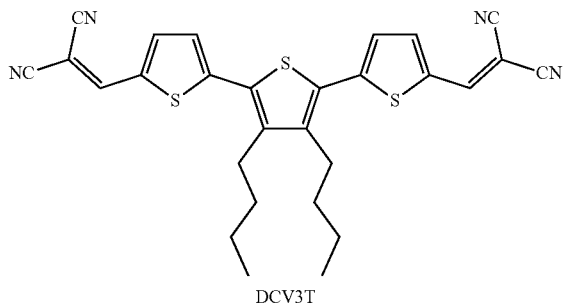

DCV3T

The materials Z1 to Z3 used in the respective examples are shown in Table 9.

TABLE 9

| | Z1 | Z2 | Z3 | External quantum efficiency | Absorptivity |
|---|---|---|---|---|---|
| Example 16 | Y1 | Exemplified Compound A1 | C60 | o | o |
| Example 17 | Y2 | Exemplified Compound A1 | C60 | o | o |
| Example 18 | Y3 | Exemplified Compound A1 | C60 | o | o |
| Example 19 | Y1 | Exemplified Compound A2 | C70 | o | o |
| Example 20 | Y2 | Exemplified Compound A2 | C60 | o | o |
| Example 21 | Y3 | Exemplified Compound A2 | C60 | o | o |
| Example 22 | Y3 | Exemplified Compound A2 | C70 | o | o |
| Example 23 | Y2 | Exemplified Compound A7 | C60 | o | o |
| Example 24 | Y3 | Exemplified Compound A7 | C60 | o | o |
| Example 25 | Y3 | Exemplified Compound A10 | C60 | o | o |
| Example 26 | Y3 | Exemplified Compound A23 | C60 | o | o |
| Example 27 | Y2 | Exemplified Compound AA2 | C60 | o | o |
| Example 28 | Y3 | Exemplified Compound AA2 | C60 | o | o |
| Example 29 | Y3 | Exemplified Compound AB3 | C60 | o | o |
| Example 30 | Y2 | Exemplified Compound AB5 | C60 | o | o |
| Example 31 | Y3 | Exemplified Compound B1 | C60 | o | o |
| Example 32 | Y3 | Exemplified Compound B4 | C60 | o | o |
| Example 33 | Y1 | Exemplified Compound C5 | C60 | o | o |
| Example 34 | Y2 | Exemplified Compound C5 | C60 | o | o |
| Example 35 | Y3 | Exemplified Compound C5 | C60 | o | o |
| Example 36 | Y2 | Exemplified Compound C12 | C60 | o | o |
| Example 37 | Y3 | Exemplified Compound C17 | C60 | o | o |
| Example 38 | Y2 | Exemplified Compound C21 | C60 | o | o |
| Example 39 | Y1 | Exemplified Compound CA2 | C60 | o | o |
| Example 40 | Y3 | Exemplified Compound CA2 | C60 | o | o |

TABLE 9-continued

| | Z1 | Z2 | Z3 | External quantum efficiency | Absorptivity |
|---|---|---|---|---|---|
| Example 41 | Y3 | Exemplified Compound A2 | DCV3T | o | o |
| Example 42 | Y3 | Exemplified Compound C5 | DCV3T | o | o |
| Comparative Example 2 | Y3 | Comparative Compound a-2 | C60 | x | x |
| Comparative Example 3 | Y3 | Comparative Compound a-2 | DCV3T | x | x |

Evaluation of Photoelectric Conversion Element (1) External Quantum Efficiency

A voltage of 5 V was applied to each of the resultant elements, and external quantum efficiency at that time was measured. The external quantum efficiency was calculated by measuring the density of a photocurrent flowing when the element was irradiated with monochromatic light having an intensity of 50 µW/cm$^2$, the light corresponding to each wavelength, under a state in which the voltage of 5 V was applied between the hole-collecting electrode 4 and the electron-collecting electrode 5. Here, the photocurrent density was determined by subtracting the density of a dark current at the time of light shielding from a current density at the time of the light irradiation. The monochromatic light used at the time of the measurement of the photocurrent density is obtained by monochromatizing white light output from a xenon lamp (apparatus name: XB-50101AA-A, manufactured by Ushio Inc.) with a monochromator (apparatus name: MC-10N, manufactured by Ritu Oyo Kougaku Co., Ltd.). The application of the voltage to the element and the current measurement were performed with a source meter (apparatus name: R6243, manufactured by Advantest Corporation). In addition, the light was caused to enter vertically to the element and from an upper electrode (electron-collecting electrode 5) side.

A relative value for external quantum efficiency at a wavelength of 550 nm when the external quantum efficiency of the photoelectric conversion element of Example 16 was defined as 1 was evaluated by the following criteria. The results are shown in Table 9.

o: A case in which the relative value for the external quantum efficiency is 0.85 or more x: A case in which the relative value for the external quantum efficiency is less than 0.8

(2) Light Absorptivity of Inside of Element

The light absorptivity of the inside of each of the elements was measured. Specifically, a transmittance and a reflectance at an angle of 5° when the element was irradiated with visible light were measured with an apparatus "SolidSpec-3700" manufactured by Shimadzu Corporation, and the light absorptivity of the inside of the element was calculated by using the following equation. The light was caused to enter vertically to the element and from an upper electrode (electron-collecting electrode 5) side.

Light absorptivity of inside of element=100−transmittance−reflectance (%)

A case in which a light absorptivity at a wavelength of 550 nm was 80% or more was evaluated as o, and a case in which the light absorptivity was less than 80% was evaluated as x. The results are shown in Table 9.

As can be seen from the foregoing results, the compound according to the embodiment of the present disclosure has a high molar extinction coefficient, a high element absorptivity, and high external quantum efficiency. This results from the fact that the light-absorbing material forming the photoelectric conversion element according to the embodiment of the present disclosure has high absorption sensitivity in the entirety of the visible light region. Meanwhile, each of the compounds used in Comparative Examples has a low element absorptivity and hence has low conversion efficiency.

As described above by way of Examples, when a photoelectric conversion layer containing the organic compound according to the embodiment of the present disclosure is used, photoelectric conversion can be efficiently performed in the entirety of the visible light region, and a photoelectric conversion element can be produced under a stable vapor deposition process.

According to the present disclosure, there can be provided an organic compound having light absorption in a wide range of the visible light region and having a high molar extinction coefficient.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-160492, filed Aug. 23, 2017, which is hereby incorporated by reference herein in its entirety.

What is claimed is:

1. An organic compound, which is represented by general formula [1]:

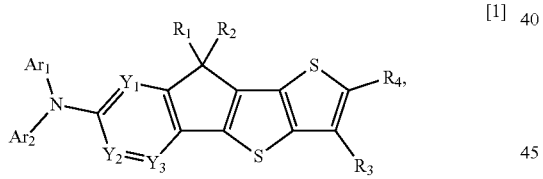

wherein, in the general formula [1], $Ar_1$ and $Ar_2$ are each an aryl group, the $Ar_1$ and the $Ar_2$ may each have a halogen atom, a cyano group, an alkyl group, an alkoxy group, an aryl group, or a heteroaryl group as a substituent, the alkyl group, the alkoxy group, the aryl group, or the heteroaryl group serving as the substituent may further have a halogen atom, a cyano group, an alkyl group, or an alkoxy group as a substituent, and the $Ar_1$ and the $Ar_2$ may be bonded to each other to form a ring, wherein $R_1$ and $R_2$ are each independently selected from the group consisting of a hydrogen atom, a halogen atom, a cyano group, an alkyl group, an aryl group having 6 to 18 carbon atoms, and a heteroaryl group having 3 to 17 carbon atoms, the alkyl group represented by any one of the $R_1$ and the $R_2$ may have a halogen atom as a substituent, the aryl group having 6 to 18 carbon atoms, and the heteroaryl group having 3 to 17 carbon atoms each represented by any one of the $R_1$ and the $R_2$ may each have a halogen atom, a cyano group, an alkyl group, or an alkoxy group as a substituent, and the $R_1$ and the $R_2$ may be bonded to each other to form a ring, wherein $R_3$ is selected from the group consisting of a hydrogen atom, a halogen atom, a cyano group, and an alkyl group, and the alkyl group represented by the $R_3$ may have a halogen atom as a substituent, wherein $Y_1$ to $Y_3$ are each independently selected from the group consisting of a methine group and a nitrogen atom, and when any one of the $Y_1$ to the $Y_3$ represents a methine group, the methine group may have a substituent and the substituent is each independently selected from the group consisting of a halogen atom, a cyano group, and an alkyl group, and the alkyl group serving as the substituent that the methine group has may further have a halogen atom as a substituent, and wherein $R_4$ represents a substituent selected from the group consisting of general formulae [1-1] and [1-2], and * in each of the following general formulae [1-1] and [1-2] represents a bonding position:

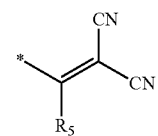

[1-1]

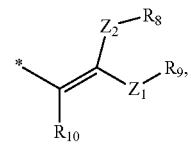

[1-2]

wherein, in the general formulae [1-1] and [1-2], $R_5$ and $R_8$ to $R_{10}$ are each independently selected from the group consisting of a hydrogen atom, a halogen atom, a cyano group, an amino group, an amide group, an alkyl group, an alkoxy group, an alkenyl group, an alkynyl group, an aryl group having 6 to 18 carbon atoms, and a heteroaryl group having 3 to 17 carbon atoms, and the $R_8$ and the $R_9$ are bonded to each other to form a ring, and wherein the amino group, the amide group, the alkyl group, the alkoxy group, the alkenyl group, the alkynyl group, the aryl group having 6 to 18 carbon atoms, or the heteroaryl group having 3 to 17 carbon atoms represented by any one of the $R_5$ and the $R_8$ to the $R_{10}$ may have a halogen atom, a cyano group, an alkyl group having 1 or more and 8 or less carbon atoms, an alkoxy group having 1 or more and 8 or less carbon atoms, an aryl group having 6 to 12 carbon atoms, or a heteroaryl group having 4 or more and 11 or less carbon atoms as a substituent, and wherein, in the general formula [1-2], $Z_1$ and $Z_2$ are each independently selected from groups represented by formulae [1-3] to [1-5], and * in each of the formulae [1-3] to [1-5] represents a bonding position

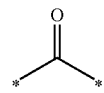

[1-3]

-continued

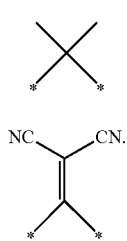

[1-4]

[1-5]

2. The organic compound according to claim 1, wherein the $R_3$ represents a hydrogen atom.

3. The organic compound according to claim 1, wherein the organic compound is represented by general formula [2]:

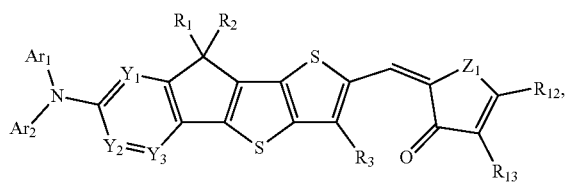

[2]

wherein, in the general formula [2], $R_{12}$ and $R_{13}$ are each independently selected from the group consisting of a hydrogen atom, a halogen atom, a cyano group, an amino group, an amide group, an alkyl group, an alkoxy group, an alkenyl group, an alkynyl group, an aryl group having 6 to 18 carbon atoms, and a heteroaryl group having 3 to 17 carbon atoms, the amino group, the amide group, the alkyl group, the alkoxy group, the alkenyl group, the alkynyl group, the aryl group having 6 to 18 carbon atoms, or the heteroaryl group having 3 to 17 carbon atoms represented by any one of the $R_{12}$ and the $R_{13}$ may have a halogen atom, a cyano group, an alkyl group having 1 to 8 carbon atoms, an alkoxy group having 1 to 8 carbon atoms, an aryl group having 6 to 12 carbon atoms, or a heteroaryl group having 4 to 11 carbon atoms as a substituent, and the $R_{12}$ and the $R_{13}$ are bonded to each other to form a ring.

4. The organic compound according to claim 3, wherein the organic compound is represented by general formula [3]:

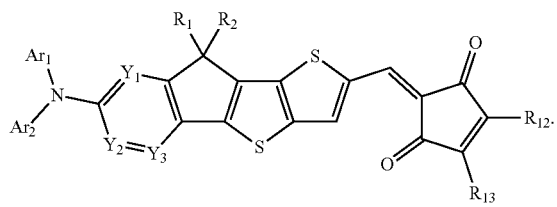

[3]

5. The organic compound according to claim 3, wherein the ring formed by the bonding of the $R_{12}$ and the $R_{13}$ to each other comprises one of a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

6. The organic compound according to claim 1, wherein the organic compound is represented by general formula [4]:

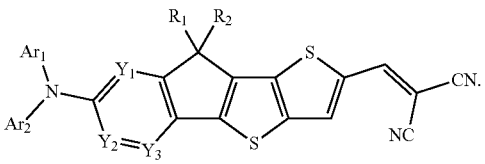

[4]

7. The organic compound according to claim 1, wherein all of the $Y_1$ to the $Y_3$ represent methine groups.

8. The organic compound according to claim 1, wherein at least one of the $Y_1$ to the $Y_3$ represents a nitrogen atom.

9. The organic compound according to claim 1, wherein the $Z_1$ and the $Z_2$ each represent a group represented by the formula [1-3].

10. An organic electronic element comprising:
a pair of electrodes; and
an organic compound layer arranged between the pair of electrodes,
wherein the organic compound layer contains the organic compound of claim 1.

11. A photoelectric conversion element comprising:
an anode;
a cathode; and
a first organic compound layer arranged between the anode and the cathode,
wherein the first organic compound layer contains the organic compound of claim 1.

12. The photoelectric conversion element according to claim 11, wherein the first organic compound layer comprises a photoelectric conversion layer and contains an organic n-type compound.

13. The photoelectric conversion element according to claim 12, wherein the organic n-type compound comprises one of a fullerene, a fullerene analog, and a fullerene derivative.

14. The photoelectric conversion element according to claim 11, further comprising a second organic compound layer arranged between the cathode and the first organic compound layer.

15. An imaging device comprising:
the photoelectric conversion element of claim 11;
a readout circuit connected to the photoelectric conversion element; and
a signal processing circuit connected to the readout circuit.

16. An imaging apparatus comprising:
the imaging device of claim 15; and
a casing configured to store the imaging device,
wherein the casing has a joining portion capable of being joined to an imaging optical system.

17. An imaging apparatus comprising:
an imaging optical system; and
an imaging device configured to receive light that has passed the imaging optical system,
wherein the imaging device comprises the imaging device of claim 15.

18. The imaging apparatus according to claim 17, further comprising a communicating portion configured to allow an image that has been picked up to be viewed from an outside.

19. The organic compound according to claim 1, wherein the $R_1$ and the $R_2$ are bonded to each other to form a ring.

20. The organic compound according to claim 1, wherein the $Ar_1$ and the $Ar_2$ do not have an alkyl group substituent.

21. The organic compound according to claim 1, wherein the $Ar_1$ and the $Ar_2$ are unsubstituted.

* * * * *